(12) United States Patent
Vanderhaeghen et al.

(10) Patent No.: US 8,633,025 B2
(45) Date of Patent: Jan. 21, 2014

(54) GENERATION OF NEURONAL CELLS FROM EMBRYONIC STEM CELLS

(75) Inventors: Pierre Vanderhaeghen, Brussels (BE); Nicolas Gaspard, Mont-sur-Marchienne (BE); Gilles Naeije, Brussels (BE); Jelle Van Den Ameele, Ghent (BE); Fabienne Devreker, Brussels (BE); Yvon Englert, Herne (BE)

(73) Assignee: Universite Libre de Bruxelles, Brussels (BE)

( * ) Notice: Subject to any disclaimer, the term of this patent is extended or adjusted under 35 U.S.C. 154(b) by 631 days.

(21) Appl. No.: 12/674,050

(22) PCT Filed: Aug. 1, 2008

(86) PCT No.: PCT/EP2008/060183
§ 371 (c)(1),
(2), (4) Date: Feb. 18, 2010

(87) PCT Pub. No.: WO2009/024448
PCT Pub. Date: Feb. 26, 2009

(65) Prior Publication Data
US 2010/0166720 A1   Jul. 1, 2010

(30) Foreign Application Priority Data
Aug. 20, 2007   (EP) .................................... 07114636

(51) Int. Cl.
*C12N 5/00*   (2006.01)

(52) U.S. Cl.
USPC ............ 435/377; 435/375; 435/366; 435/325

(58) Field of Classification Search
None
See application file for complete search history.

(56) References Cited

U.S. PATENT DOCUMENTS

| | | | | |
|---|---|---|---|---|
| 7,527,971 | B2 * | 5/2009 | Musick | 435/325 |
| 2002/0137095 | A1 | 9/2002 | Mikoshiba et al. | |
| 2004/0092012 | A1 * | 5/2004 | Okano et al. | 435/366 |
| 2006/0093586 | A1 * | 5/2006 | Musick | 424/93.7 |

FOREIGN PATENT DOCUMENTS

| | | |
|---|---|---|
| JP | 2003-111588 | 4/2003 |
| JP | 2002-17361 | 7/2003 |
| JP | 2004-535199 | 11/2004 |
| JP | 2005-522213 | 7/2005 |
| JP | 2007-529227 | 10/2007 |
| WO | WO 01/51616 | 7/2001 |
| WO | WO 03/006950 | 1/2003 |
| WO | WO 03/087296 | 10/2003 |
| WO | WO 2004/087870 | 10/2004 |
| WO | WO 2005/090558 | 9/2005 |
| WO | WO 2007/058982 | 5/2007 |

OTHER PUBLICATIONS

Tosh D et al. 2002. Conversion of pancreatic cells to hepatocytes. Biochem Soc Trans 30:51-55.*
Castro RF et al. 2002. Failure of bone marrow cells to transdifferentiate into neural cells in vivo. Science 297: 1299.*
Mezey E et al. and Castro RF et al. 2003. "Comment on Failure of bone marrow cells to transdifferentiate into neural cells invivo", "Response to Comment on Failure of bone marrow cells to trarlsdifferentiate into neural Cells in vivo." Science299:1184b,c.*
Roybon et al Stem Cells 24:1594-1604. 2006.*
Gulacsi, et al. "Sonic Hedgehog and Bone Morphogenetic Protein Regulate Interneuron Development from Dorsal Telencephalic Progenitors In Vitro," *The Journal of Neuroscience*, vol. 23, No. 30, pp. 9862-9872, Oct. 29, 2003.
Lai, et al. "Sonic Hedgehog Regulates Adult Neural Progenitor Proliferation in vitro and in vivo," *Nature Neuroscience*, vol. 6, No. 1, pp. 21-27, Jan. 1, 2003.
Palma, et al. "Sonic Hedgehog Controls Stem Cell Behavior in the Postnatal and Adult Brain," *Development*, vol. 132, No. 2, pp. 335-344, Jan. 2005.
Sasaki, et al. "The Role of Sonic Hedgehog in Dendritic Spine Formation," *Neuroscience Research*, Abstract (online), p. S88, Jul. 20, 2007.
Ying, et al. "Conversion of Embryonic Stem Cells into Neuroectodermal Precursors in Adherent Monoculture," *Nature Biotechnology*, vol. 21, No. 2, pp. 183-186, Feb. 1, 2003.
International Search Report dated Dec. 22, 2008 and issued to related international application PCT/EP2008/060183.
Fong, et al. "Trophism of Neural Progenitor Cells to Embryonic Stem Cells: Neural Induction and Transplantation in a Mouse Ischemic Stroke Model," *Journal of Neuroscience Research*, vol. 85, No. 9, pp. 1851-1862, Jul. 2007.
Development of Neurotoxic Assessment System of Drugs Using ES Cell-derived Nerve Cells, and Neurotoxicity-associated Gene/Protein Database Architecture, General Overview/shared study report, pp. 25-28, 2006.
Kohtz, et al. "N-terminal Fatty-acrylation of Sonic Hedgehog Enhances the Induction of Rodent Ventral Forebrain Neurons," *Development*, vol. 128, No. 12, pp. 2351-2363, 2001.

* cited by examiner

*Primary Examiner* — Blaine Lankford
(74) *Attorney, Agent, or Firm* — Knobbe, Martens, Olson & Bear LLP

(57) ABSTRACT

The invention relates to in vitro methods for differentiating mammalian pluripotent stem cells into cells displaying a neuronal phenotype, more particularly into cortical-type neurons including inter alia pyramidal neurons and cortical inhibitory interneurons. The invention further encompasses so-obtained neuronal cells and cell population, compositions comprising such, and further uses of said neuronal cells and cell population.

16 Claims, 18 Drawing Sheets

FIG 1
(A)
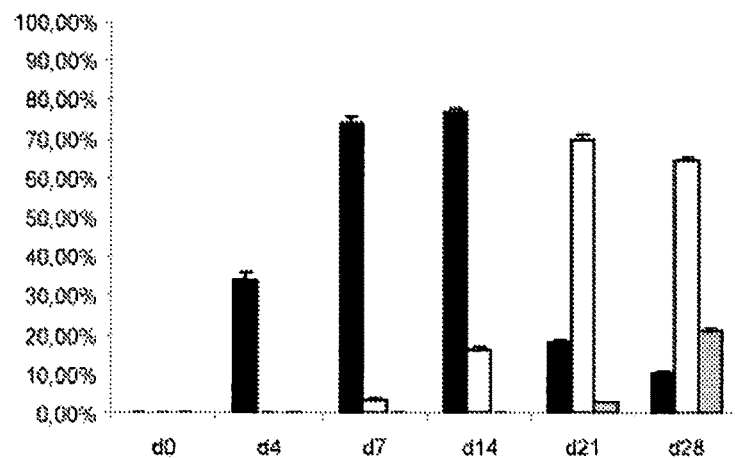
(B)
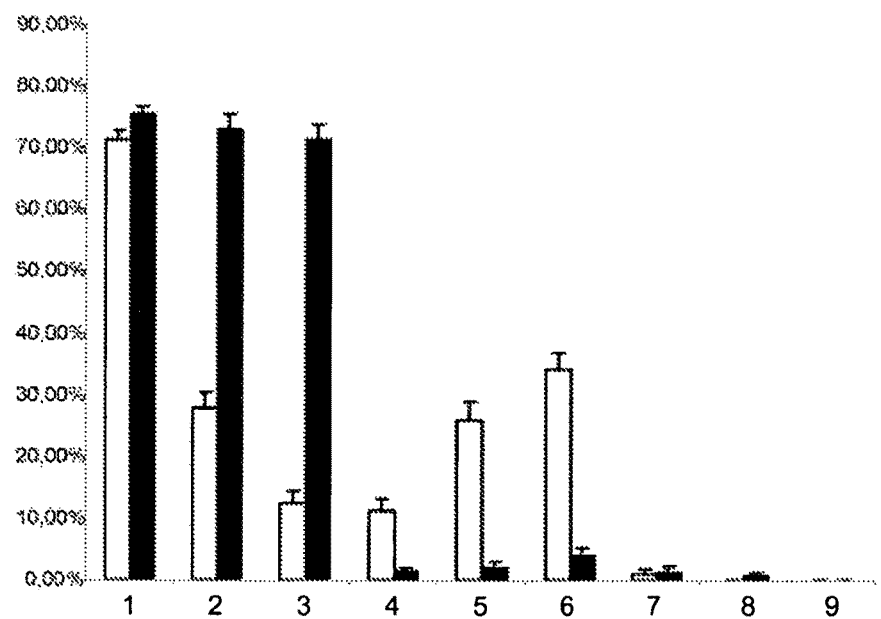

FIG 1 continued
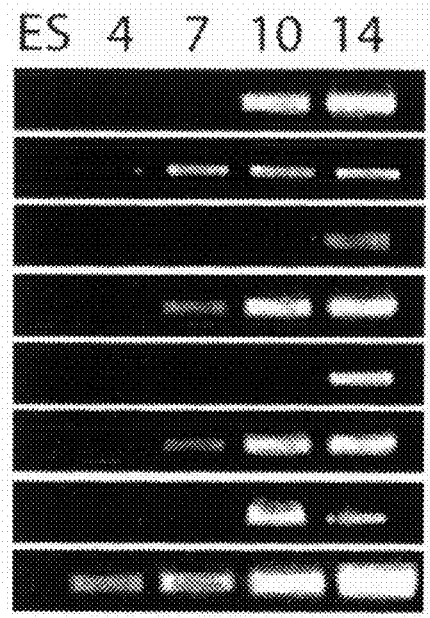
(C)
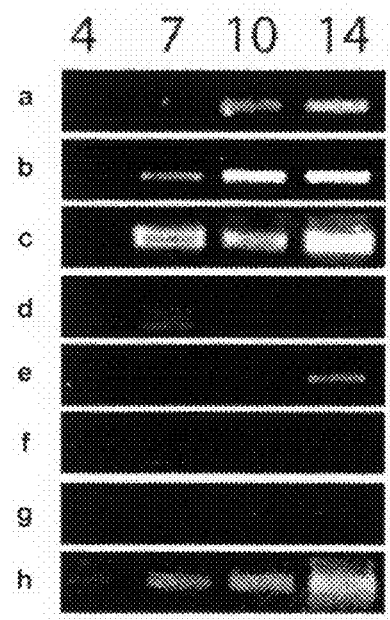
(D)
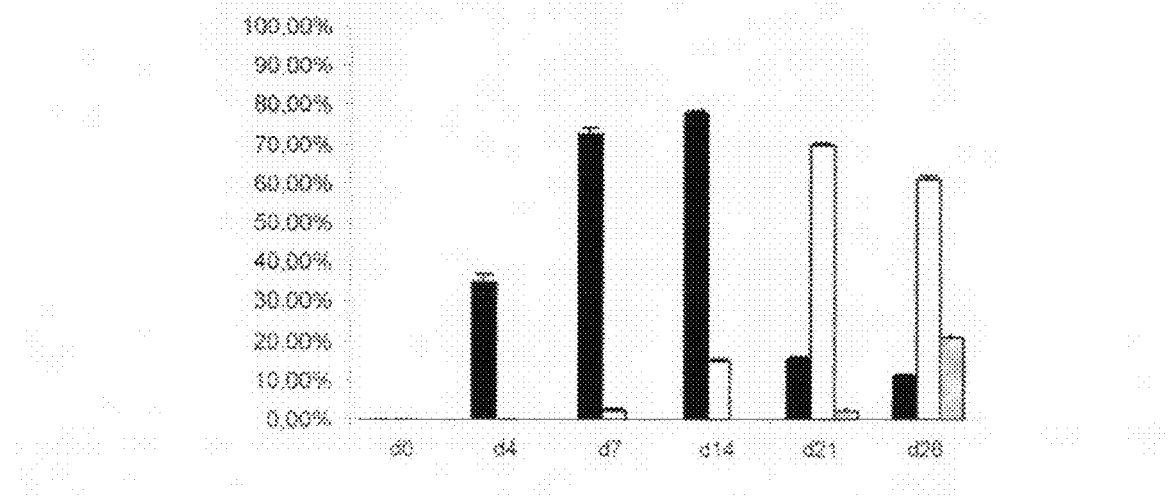
(E)

FIG 2
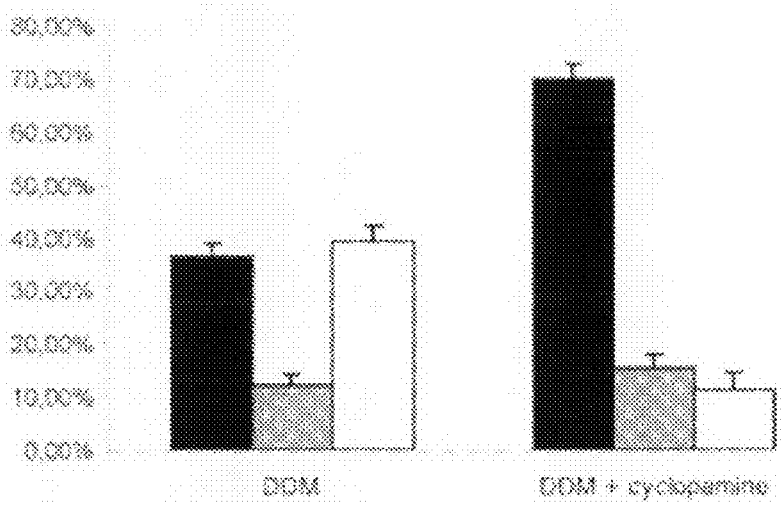
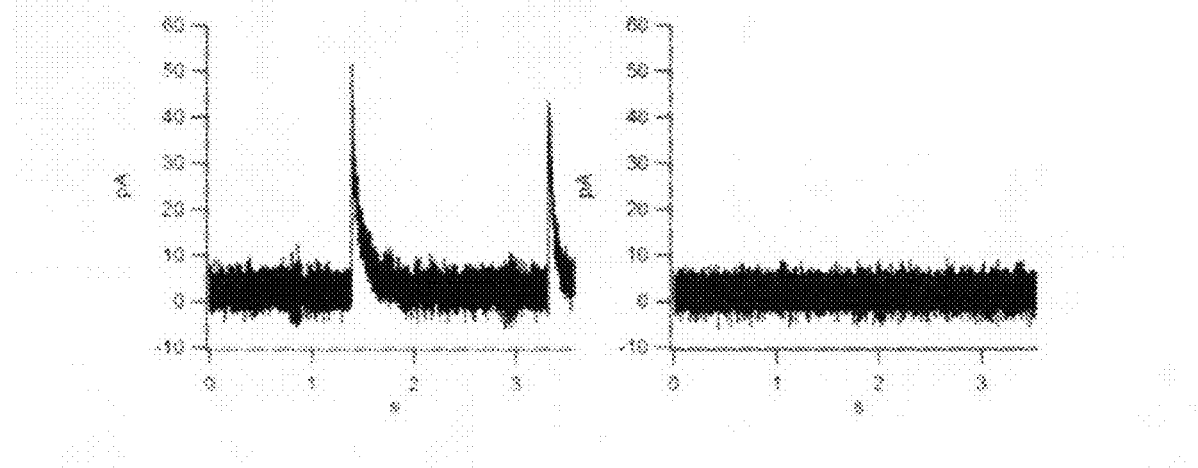

FIG 2
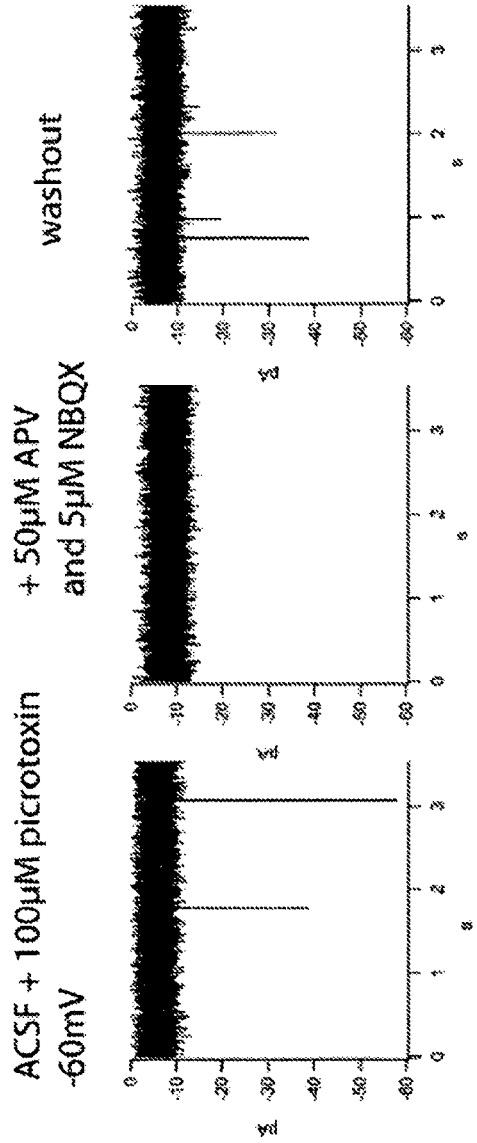
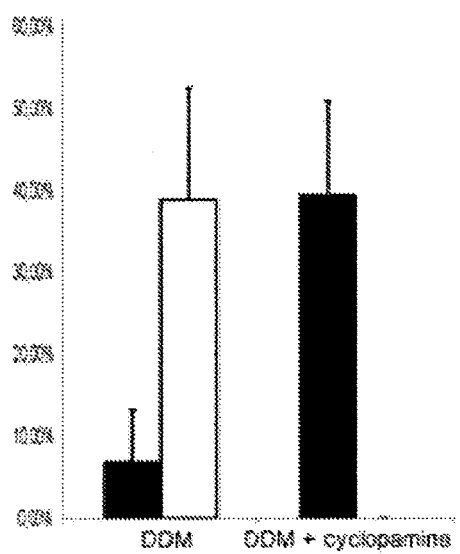

FIG 3
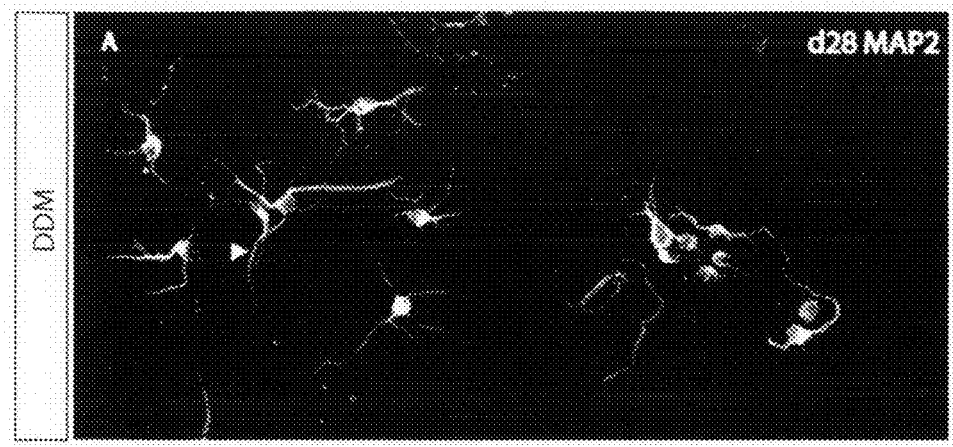
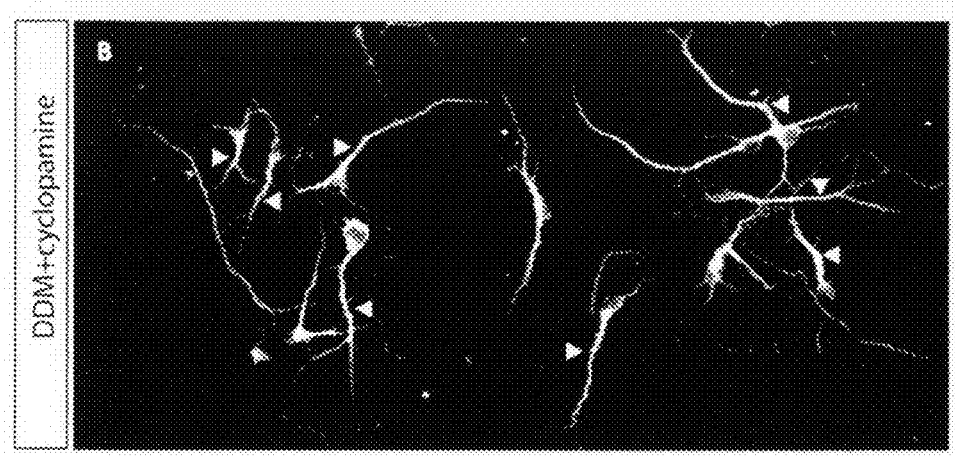
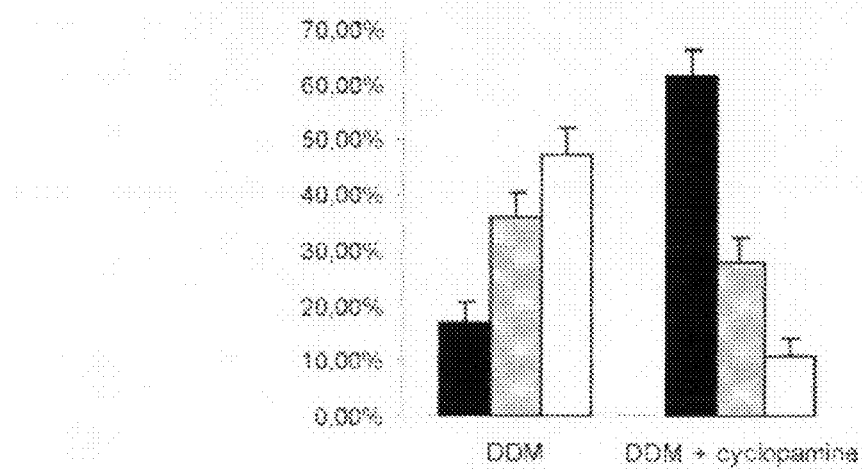

FIG 5

| Layers | | Markers | Birthdate |
|---|---|---|---|
| I | | Reelin, Calretinin, p73, Tbr1 | E10.5-11.5 |
| II-III | | Satb2, Cux1 | E13.5-16.5 |
| IV | | Satb2, Cux1 | E13.5-15.5 |
| V | | CTIP2, Otx1, ER81, Tbr1 | E12.5-14.5 |
| VI | | Tbr1, Otx1, CTIP2, Tle4, FoxP2 | E11.5-14.5 |
| Subplate (VIb) | | Tbr1, calretinin, Reelin | E10.5-13.5 |

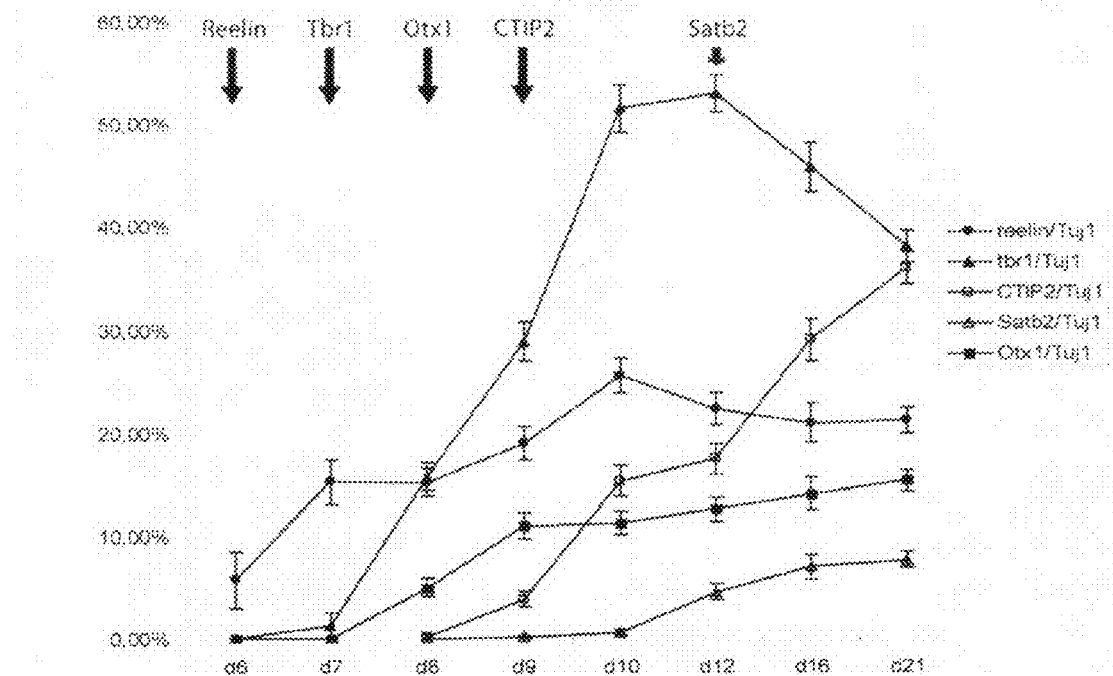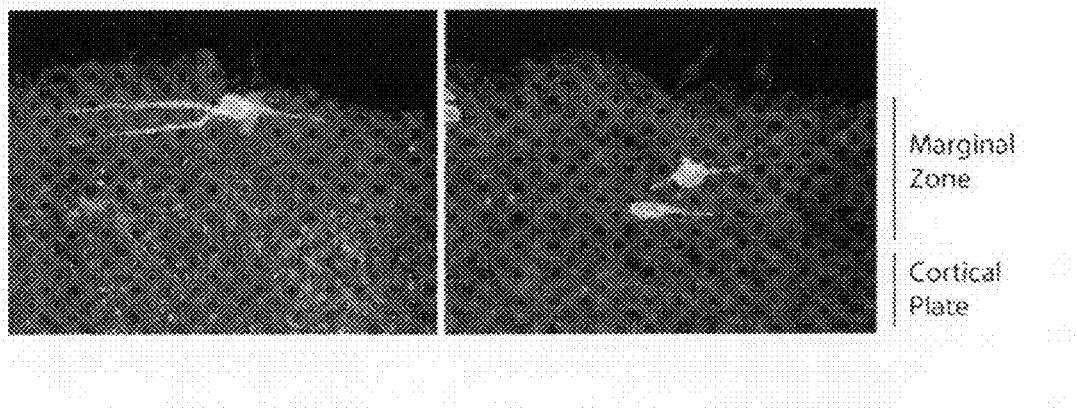
FIG 6

FIG 9
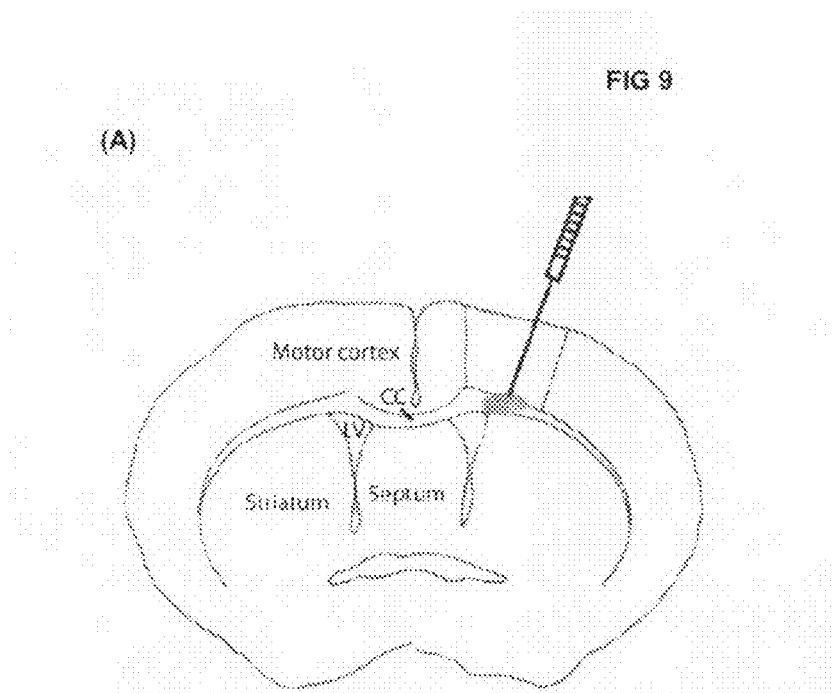
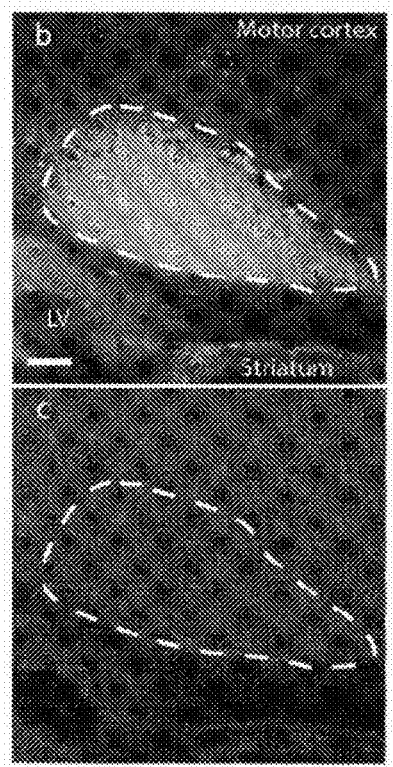

FIG 9 continued
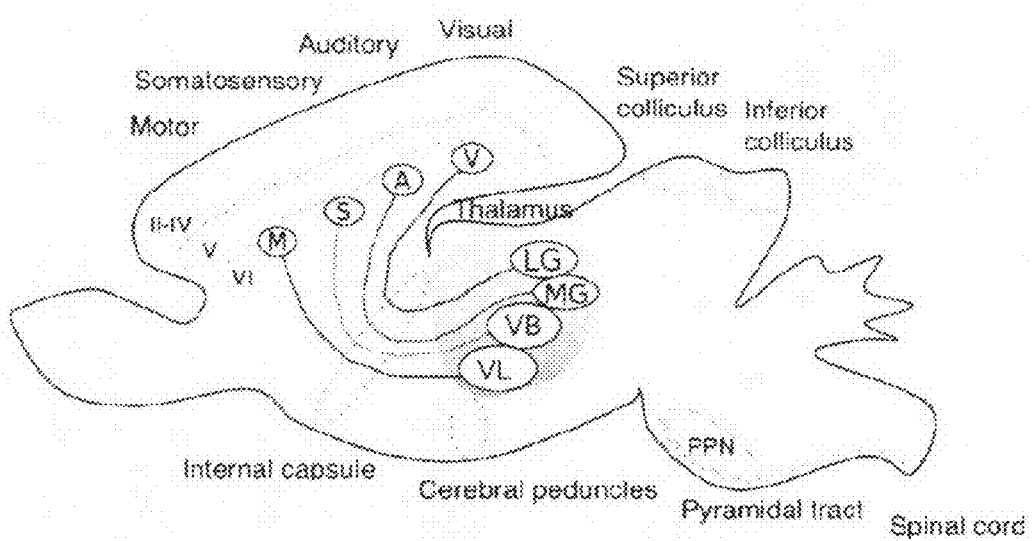
(E)
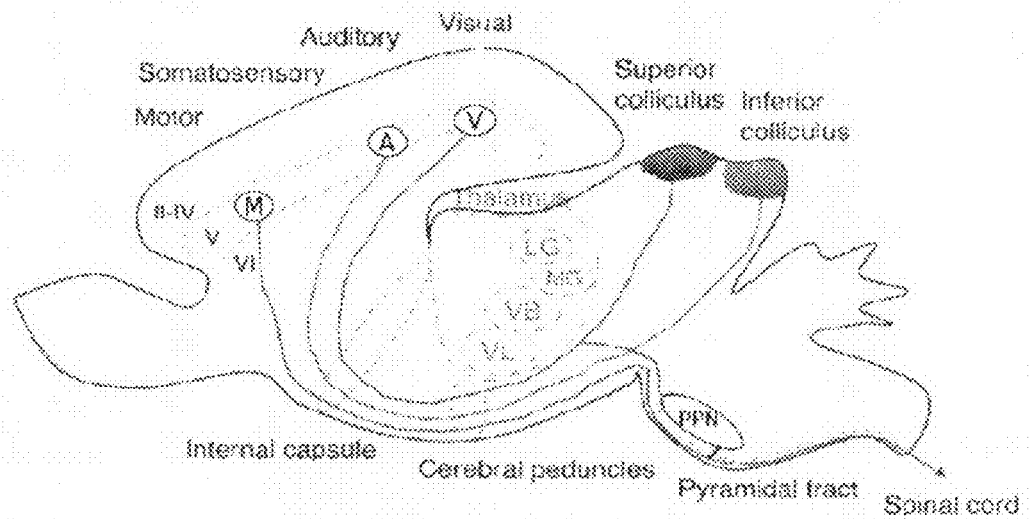
(F)

FIGURE 12
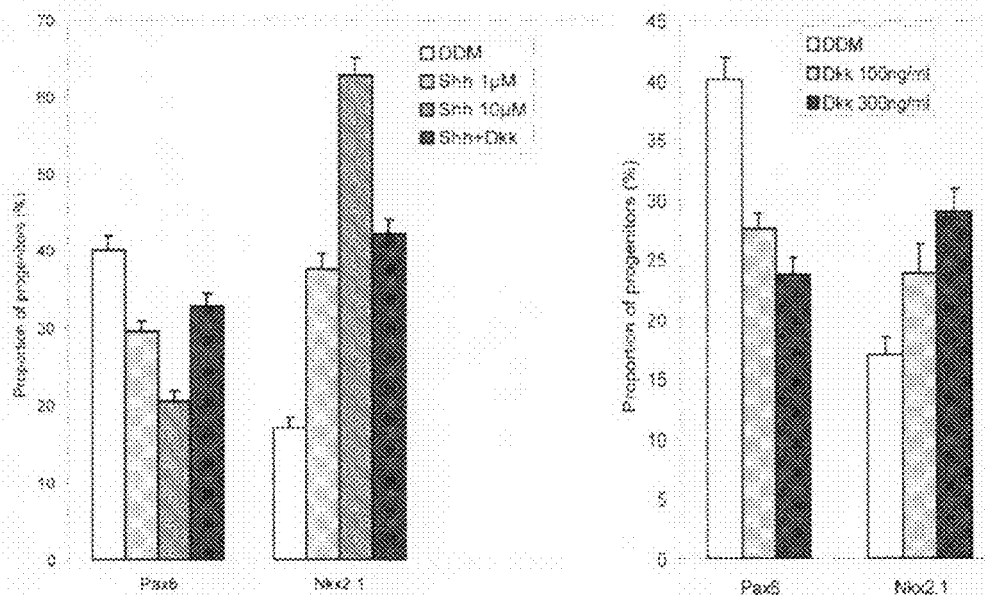
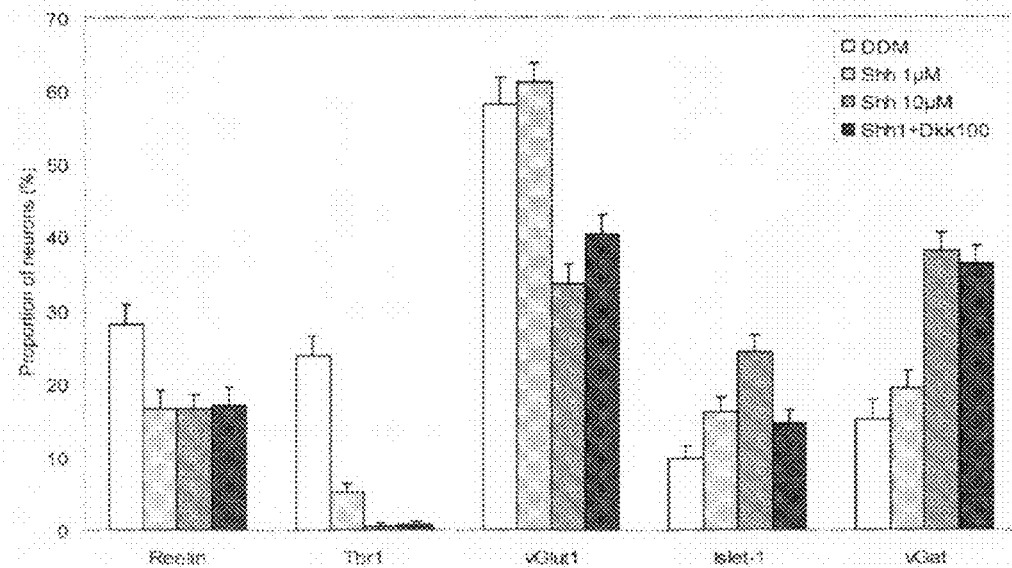

GENERATION OF NEURONAL CELLS FROM EMBRYONIC STEM CELLS

CROSS-REFERENCE TO RELATED APPLICATIONS

This application is the U.S. National Phase under 35 U.S.C. §371 of International Application PCT/EP2008/060183, filed Aug. 1, 2008, which claims priority to EP Application No. 07114636.9, filed Aug. 20, 2007.

FIELD OF THE INVENTION

The invention relates to in vitro methods for differentiating mammalian pluripotent stem cells into cells displaying a neuronal phenotype, more particularly into cortical-type neurons including inter alia pyramidal neurons and cortical inhibitory interneurons. The invention further encompasses so-obtained neuronal cells and cell populations, compositions comprising such, and further uses of said neuronal cells and cell populations.

BACKGROUND OF THE INVENTION

Readily accessible in vitro neuronal cells and populations of required identity are crucial in a number of applications, e.g., in the study of the normal physiological behaviour of the respective neuronal types, in the study of the aetiology of neurological or neuropsychiatric disorders, in neuron-replacement therapies of neurological diseases, or in various cell-based assays of pharmacological, toxicological or other agents, etc.

In particular, cultured cortical and striatal neurons would aid in deciphering the normal development, structure and physiology of the cerebral cortex and basal ganglia, as well as allow to generate representative models of, and cell screening platforms for, widespread cortical afflictions, including Alzheimer's disease, Huntington's disease, stroke or epilepsy. However, to date robust and simple methods are not available to derive cortical neurons readily and consistently from mature or embryonic brain tissue, nor from other cell sources.

Hence, there exists a need in the art to provide straightforward methods that can reproducibly generate in vitro neuronal populations representative of the cerebral cortex or the striatum. Preferably, said methods may depart from a comparably well-characterised and accessible cell source. The resultant in vitro neuronal cultures may comprise, and preferably be significantly enriched in, any one or both of the basic cortical neuronal types including pyramidal neurons and inhibitory interneurons. More particularly, said neuronal cultures may also display further levels of neuronal specialisation or differentiation within any of said basic cortical neuronal types, as evidenced by, for example, differences in morphology, marker expression, electro-physiology, etc.

Ying et al. 2003 (Nat Biotechnol 21: 183-6) reported that in adherent monoculture of mouse embryonic stem (ES) cells (i.e., without the formation of embryoid bodies in suspension culture, and without co-culture of ES cells with non-ES cells), elimination of inductive signals for alternative cell fates sufficed for a bulk of the ES cells to develop into neural precursors. However, these authors did not address whether said neural precursors were able to generate cortical neuronal subtypes such as pyramidal cells or interneurons, or striatal neurons, or to emulate cortical cell type development, and thus also did not disclose any conditions to achieve such cortical differentiation.

SUMMARY OF THE INVENTION

The present invention addresses one or more of the above discussed needs in the art.

In particular, when adjusting the adherent ES cell monoculture method of Ying et al. 2003 (supra), the inventors surprisingly realised that a great majority of neural precursors obtained using their method expressed markers of anterior neuroectoderm (such as, e.g., the homeobox proteins OTX1, OTX2 and FoxG1), indicating that said neural progenitors had prospective forebrain identity. In addition, the inventors also found that a subset of these neural progenitors expressed markers of early dorsal forebrain primordium (such as, e.g., OTX1, PAX6, Emx1 and Emx2), while another subset expressed markers characteristic of the ventral part of early rostral-most forebrain (such as, e.g., GSH2, NKX2.1 or NKX2.2, and Dlx1 or Dlx2). Taken together, this surprisingly established that adherent monoculture of pluripotent stem cells in the absence of external inductive morphogen signals produces a population of neural precursors of prospective forebrain identity, encompassing ventral as well as dorsal phenotypes.

Extending on this realisation, the inventors further succeeded to manipulate the balance between the ventral and dorsal phenotype among said forebrain neural progenitors. In particular, the inventors found that antagonising sonic hedgehog (SHH) signalling dramatically increased the prevalence of the dorsal phenotype among the neural progenitors. Even more strikingly, when SHH was antagonised, the neural progenitors eventually differentiated into neurons displaying key landmarks of cortical pyramidal neurons in terms of neurotransmission phenotype, gene expression, morphology, electrophysiological behaviour, and ability to integrate into native cerebral cortical tissue. Moreover, the so-obtained pyramidal neurons included subpopulations reminiscent of the pyramidal cell subtypes found in the different cortical layers in vivo. Conversely, stimulation of SHH signalling and/or inhibition of Wnt signalling augmented the occurrence of ventral phenotype among the neural progenitors, and has driven differentiation toward GABAergic inhibitory interneurons of cortex and striatum, or striatal (medium spiny) projection neurons.

Hence, the inventors realised methods that allow to generate cell populations highly enriched or substantially homogeneous for defined types of neural progenitors or mature neurons, in vitro from pluripotent stem cells. The methods of the invention use an adherent monoculture of the pluripotent stem cells and suitable modulation of SHH and/or Wnt signalling.

Accordingly, in an aspect (referred to herein as aspect "A1") the invention provides a method for differentiating mammalian pluripotent stem (mPS) cells into neural progenitors of dorsal forebrain identity comprising the steps of: a) plating undifferentiated mPS cells onto a substrate which allows adherence of cells thereto; and b) culturing the mPS cells of a) which have adhered to said substrate in a medium permissive to differentiation of the mPS cells; characterised in that during at least part of said culturing step b) the cells are exposed to an antagonist of the sonic hedgehog (SHH) signalling pathway.

In an embodiment, the neural progenitors of dorsal forebrain identity are positive at least for nestin and for any one, preferably two or more, more preferably all of orthodenticle homeobox 1 (OTX1), paired box protein PAX6, empty spiracles homolog 1 (Emx1), empty spiracles homolog 2 (Emx2) and Forkhead box protein G1 (FoxG1).

In a further aspect (referred to herein as aspect "A2") the invention provides a method for differentiating mPS cells into cortical pyramidal neuron like cells comprising the steps of: a) plating undifferentiated mPS cells onto a substrate which allows adherence of cells thereto; and b) culturing the mPS cells of a) which have adhered to said substrate in a medium permissive to differentiation of the mPS cells; characterised in that during at least part of said culturing step b) the cells are exposed to an antagonist of the SHH signalling pathway.

In an embodiment, the cortical pyramidal neuron like cells are positive at least for β-tubulin III (TUJ1) and/or microtubule associated protein 2 (MAP2), and for any one or both of vesicular glutamate transporter VGluT1 and VGluT2. In a further embodiment, the cortical pyramidal neuron like cells display spontaneous glutamatergic excitatory post-synaptic currents (ePSC). In a further embodiment, the cortical pyramidal neuron like cells display a pyramidal index value (PMI) greater than 1.2 µm, and may even display PMI values greater than 1.8 µm, greater than 2.4 µm, greater than 3.0 µm, or even greater than 3.6 µm.

In a yet further aspect (referred to herein as aspect "A3") the invention provides a method for differentiating mPS cells into neural progenitors of ventral forebrain identity comprising the steps of: a) plating undifferentiated mPS cells onto a substrate which allows adherence of cells thereto; and b) culturing the mPS cells of a) which have adhered to said substrate in a medium permissive to differentiation of the mPS cells; characterised in that during at least part of said culturing step b) the cells are exposed to an agonist of the SHH signalling pathway and/or to an antagonist of the Wnt signalling pathway. Preferably, the cells may be so exposed to both an agonist of the SHH pathway and an antagonist of the Wnt pathway, whereby particularly successful differentiation can be achieved.

In an embodiment, the neural progenitors of ventral forebrain identity are positive at least for nestin and for any one, preferably two or more or all of homeobox protein GSH2, homeodomain transcription factors NKX2.1 and NKX2.2, and homeobox proteins Dlx1 and Dlx2.

In another aspect (referred to herein as aspect "A4") the invention provides a method for differentiating mPS cells into cortical or striatal inhibitory interneuron or striatal projection (medium spiny) like cells comprising the steps of: a) plating undifferentiated mPS cells onto a substrate which allows adherence of cells thereto; and b) culturing the mPS cells of a) which have adhered to said substrate in a medium permissive to differentiation of the mPS cells; characterised in that during at least part of said culturing step b) the cells are exposed to an agonist of the SHH signalling pathway and/or to an antagonist of the Wnt signalling pathway. Preferably, the cells may be so exposed to both an agonist of the SHH pathway and an antagonist of the Wnt pathway, whereby particularly successful differentiation can be achieved.

In an embodiment, the cortical inhibitory interneuron like cells are positive at least for β-tubulin III (TUJ1) and/or MAP2, and for vesicular GABA transporter VGAT. In a further embodiment, the cortical inhibitory interneuron like cells display spontaneous GABAergic inhibitory post-synaptic currents (iPSC). In a yet further embodiment, the cortical inhibitory interneuron like cells display PMI values smaller than and up to 1.2 µm, and may even display PMI values smaller than 0.6 µm.

The method steps of the above aspects A1 and A2 thus allow mPS cells to proceed via the formation of neural progenitors of dorsal forebrain identity towards mature cortical pyramidal neuron like cells. On the other hand, the method steps of the above aspects A3 and A4 direct mPS cells through neural progenitors of ventral forebrain identity to mature cortical or striatal inhibitory interneuron or striatal projection (medium spiny) like cells. Consequently, while the desired cell types may arise substantially throughout the culturing step b) of the respective methods, the neural progenitors will mostly emerge earlier in the differentiation process and the mature neuron like cells will mainly arise later in the differentiation process.

Accordingly, in methods of any of the above aspects A1 or A3, the duration of the culturing step b) may preferably be between 3 days and 21 days, more preferably between 4 days and 18 days, even more preferably between 7 days and 16 days or between 7 days and 14 days, and yet more preferably between 10 days and 14 days, such as to maximise the proportion of the respective desired neural precursors in the acquired cell cultures. Conversely, in methods of any of the above aspects A2 or A4, the duration of the culturing step b) may preferably be at least 16 days, more preferably at least 18 days, and even to more preferably at least 21 days or at least 24 days, such as, for example, between 18 days and 40 days, more preferably between 21 days and 35 days, and even more preferably between 21 days and 30 days, e.g., about 21 days, about 23 days, about 25 days, about 28 days or about 30 days. This can maximise the proportion of the respective mature neuron like cells in the acquired cell cultures. The start of the culturing step b), in other words the time point corresponding to zero days (t=0 days), is deemed throughout this specification to be the moment when the mPS cells are first exposed to the medium permissive to their differentiation.

As noted, the methods of the invention employ differentiation conditions in which external inductive morphogen signals are largely absent. In particular, the medium wherein mPS cells are cultured in step b) of the above aspects may preferably lack any components that may otherwise induce caudalisation of neural progenitors. For example, in an embodiment the medium may lack any one, preferably any two or more, and most preferably all of the following: animal (e.g., mammalian) serum or plasma; retinoic acid (RA); any members of the fibroblast growth factor (FGF) family of proteins; and any members of the Wnt family of proteins. It shall be appreciated that the medium may entirely lack such factors or may comprise trace amounts thereof below concentrations at which they would exhibit an effect on the mPS cells.

As can be understood, methods of the above aspects may commonly achieve cell populations enriched or substantially homogeneous for the desired neural progenitors or mature neuron like cells. When needed, such cell populations may be collected or harvested and said neural progenitors or mature neuron like cells may be further enriched or isolated there from on the basis of their distinctive characteristics (such as, for example, their marker expression as defined above) using methods generally known in the art (e.g., FACS, clonal culture).

In addition, neural progenitors or mature neuron like cells generated by methods of the invention may encompass subgroups having distinctive characteristics. The methods of the invention may further enrich or isolate cells of such subgroups from the general population of the desired cells.

For example, the inventors have unexpectedly found that cortical pyramidal neuron like cells produced according to the invention may comprise subgroups of cells displaying markers attributable to neurons from different cortical layers, such as reelin (characteristic for Cajal-Retzius neurons); TBR1 (T-box brain 1; characteristic for Cajal-Retzius and layer VI neurons); CTIP2 (Chicken ovalbumin upstream promoter-transcription factor (COUP-TF)-interacting protein 2)

and OTX1 (both characteristic for layer V and less for layer VI neurons); or SATB2 (SATB homeobox 2; characteristic for layer II, III and IV neurons); or CUX1 (cut-like homeobox 1; characteristic for layer II, III and IV neurons); or comprising a combination of said markers, such as, for example, comprising the marker combination reelin, TBR1, calretinin and p73 (characteristic for Cajal-Retzius neurons), or the marker combination reelin and CTIP2, or the marker combination Tbr1 and CTIP2, or the marker combination Cux1 and SATB2, and others. Accordingly, the methods of aspect A2 may further comprise enriching or isolating from the obtained cortical pyramidal neuron like cells a subpopulation of cells positive for one or more markers chosen from: reelin; TBR1; CTIP2; OTX1; SATB2; CUX1; or cells comprising the marker combination reelin, TBR1, calretinin and p73; or comprising the marker combination reelin and CTIP2; or comprising the marker combination Tbr1 and CTIP2; or comprising the marker combination Cux1 and SATB2.

The inventors further realised that in the populations of cortical pyramidal neuron like cells produced according to the invention the various subtypes of cortical neurons tend to appear sequentially in a reproducible fashion, as evidenced in the examples. Hence, in embodiments the duration of the culture step b) of the methods of aspect A2 can be suitably modulated to achieve neuronal populations having desired proportions of the cortical neuron types.

For example, in an embodiment, the duration of the culturing step b) in methods of aspect A2 may be between 6 and 20 days, preferably between 8 and 18 days, more preferably between 9 and 16 days, even more preferably between 1.0 and 14 days, most preferably between 10 and 12 days, to achieve a population of cortical pyramidal neuron like cells particularly enriched in cells comprising expression of reelin and/or Tbr1.

In another embodiment, the duration of the culturing step b) in methods of aspect A2 may be between 6 and 20 days, preferably between 8 and 18 days, more preferably between 9 and 16 days, even more preferably between 10 and 14 days, most preferably between 12 and 14 days, to achieve a population of cortical pyramidal neuron like cells particularly enriched in cells comprising expression of CTIP2.

In a further embodiment, the duration of the culturing step b) in methods of aspect A2 may be between 8 and 20 days, preferably between 10 and 18 days, more preferably between 12 and 16 days, even more preferably between 14 and 16 days, to achieve a population of cortical pyramidal neuron like cells particularly enriched in cells comprising expression of CUX1 and/or SATB2.

Further, extensive in vivo experiments revealed that the cortical pyramidal neuron like cells produced according to the invention may predominantly display identity of neurons belonging to the occipital or visual cortex. Thus, in an embodiment, the cortical pyramidal neuron like cells may further be positive for the CoupTF1 and/or CoupTF2 transcription factors characteristic for embryonic occipital or visual cortex. Accordingly, the present methods allow for obtaining neurons of occipital or visual cortex identity.

The methods of the invention thus allow for the first time to generate, using simple and robust conditions, considerably large, enriched populations of anterior forebrain neural progenitors and mature cortical pyramidal, or cortical/striatal inhibitory interneuron or projection (medium spiny) neuronal cells. Such cells may be employed in various applications, such as in pharmacological, toxicological or genetic screening assays; in cellular models of normal brain development and function as well as of neurological or neuropsychiatric diseases; in neuron-replacement therapies of such diseases; etc.

Accordingly, in further aspects the invention provides neural progenitors and mature neuron like cells, as well as cell cultures and populations comprising such, obtainable or directly obtained using the methods of the invention, in particular using the methods of any of above aspects A1 to A4.

The invention also provides methods for introducing, such as for example injecting or implanting, neural progenitors or mature neuron like cells, or cell cultures and populations comprising such, into a non-human experimental animal, and also provides the so-modified animal.

The methods of the invention are also suitable for in vitro carrying out and analysis of progression of neuronal differentiation, particularly differentiation towards the neuronal fates detailed herein, as well as for screening assays for modulators of said differentiation.

In related aspects, the invention provides compositions, including pharmaceutical formulations, comprising the neural progenitors or mature neuron like cells of the invention, or cell populations comprising such.

In other aspects, the invention provides prophylactic and therapeutic uses, or non-medical uses, of the neural progenitors or mature neuron like cells of the invention, or cell populations comprising such.

These and further aspects and preferred embodiments of the invention are described in the following sections and in the appended claims.

BRIEF DESCRIPTION OF FIGURES

FIG. 1 illustrates differentiation of ES cells into cortical progenitors:

(A), (E) Sequential generation of neural progenitors (expressing Nestin, black histograms), neurons (expressing β-tubulin III, white histograms) and astroglial cells (expressing GFAP, grey histograms), following differentiation in DDM (A) or DDM+cyclo (E) conditions. X-axis denotes days of differentiation; Y axis denotes proportion of cells expressing the given marker among all cells visualised by Hoechst staining.

(B) Proportions of Nestin positive neural progenitors expressing specific neural regionalization markers following 14 days of differentiation in DDM (white histograms) or DDM+cyclo (black histograms), showing a conversion from ventral to dorsal forebrain identity in DDM+cyclo. Data are represented as mean+/−S.E.M. X axis denotes the marker tested—1: Otx1+2; 2: Pax6; 3: Otx1; 4: Gsh2; 5: Nkx2.1; 6: Nkx2.2; 7: En1; 8: Math 1; 9: HoxB1. Y-axis denotes the proportion of Nestin positive cells expressing the given marker.

(C), (D) RT-PCR of specific marker genes of the telencephalon (a. FoxG1), dorsal forebrain (b. Emx2, c. Emx1) and ventral forebrain (d. Dlx1, e. Dlx5, f. Nkx2.1, g. Lhx6), and SHH (h) from day 4-14 cultures of cells in DDM (C) or DDM+cyclo (D).

FIG. 2 illustrates generation of functional cortical neurons from ES cells in DDM+cyclo:

(A) Proportion of VGluT1 (black histograms), VGluT2 (grey histograms), and VGAT (white histograms) expression among Tuj1 positive neurons after 28 days in culture, following DDM or DDM+cyclo differentiation, showing a conversion to glutamatergic neuronal fate in DDM+cyclo. Y axis denotes the proportion of Tuj1 positive neurons expressing the respective markers.

(B), (C) Recorded iPSCs (B) and ePSCs (C) from neurons after 28 days following differentiation in DDM, which show selective inhibition by picrotoxin ($GABA_A$ inhibitor) and APV/NBQX (NMDA and AMPA receptors inhibitors).

(D) Proportion of iPSCs (white histograms) and ePSCs (black histograms) recorded among neurons in each condition, showing a much higher prevalence of ePSCs and a much lower occurrence of iPSCs in DDM+cyclo.

Figure 3:
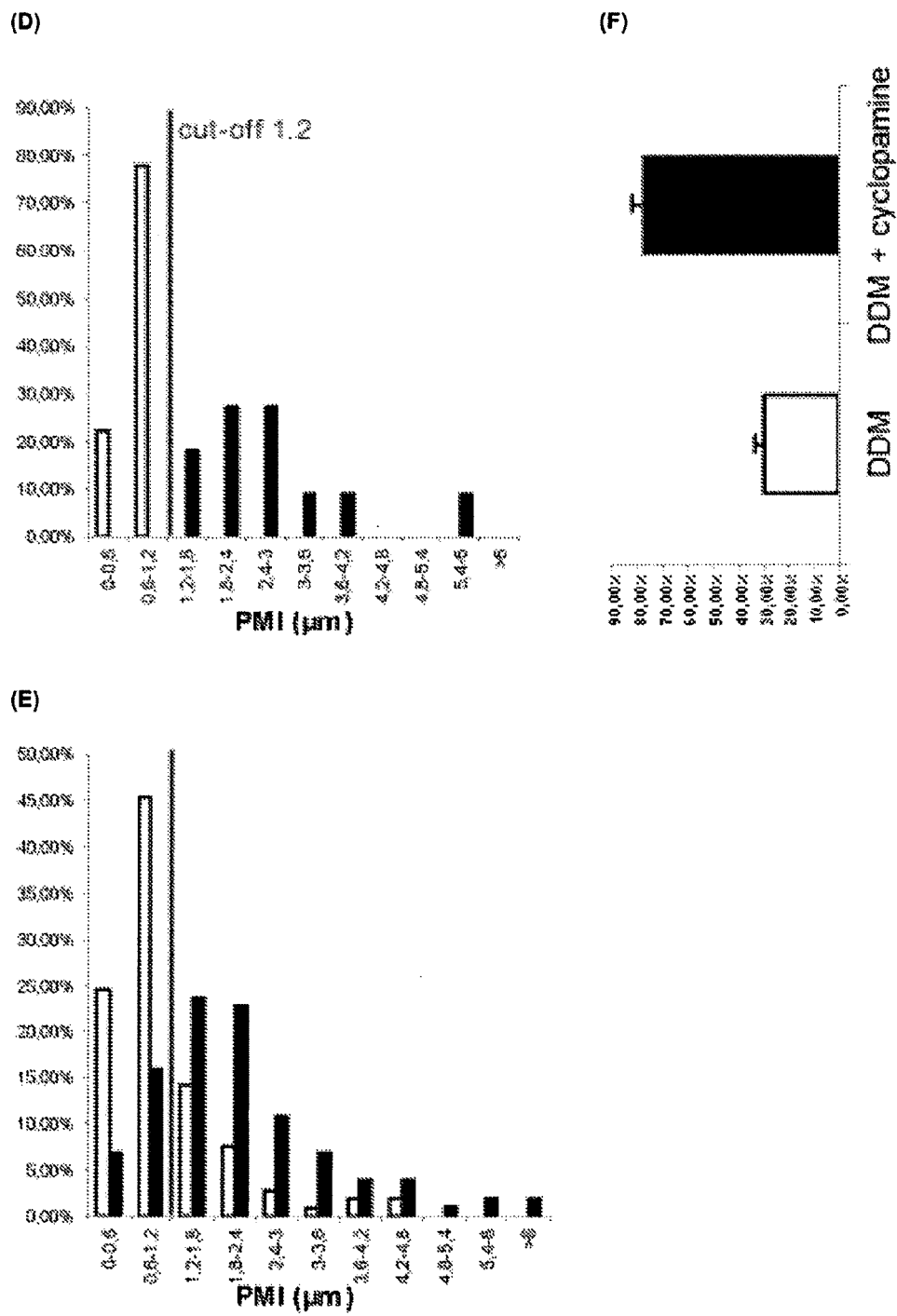

FIG. 3 illustrates generation of pyramidal neurons from ES cells in DDM+cyclo.

(A), (B) Typical morphology observed for MAP2+ mature neurons cultured for 28 days, following differentiation in DDM (A) or DDM+cyclo (B). Arrowheads point to large, 'apical-like', dendrites that are characteristic of pyramidal neurons.

(C) Semi-quantitative visual scoring of neurons displaying pyramidal (black histograms), bipolar (grey histograms) or multipolar (white histograms) morphology. Data are represented as mean+/−S.E.M. Y axis denotes proportion of MAP-2 positive neurons displaying the respective morphologies.

(D) PMI distribution among native cortical neurons (dissociated at postnatal day 2) cultured for 1 day in vitro, and stained for glutamatergic (VGluT; 1black bars) and GABAergic markers (GABA; white bars). A cut-off value of 1.2 enables to discriminate efficiently between the two populations, with glutamatergic neurons displaying higher values and GABAergic neurons displaying lower values. Y-axis denotes proportion of cells having the respective PMI values.

Figure 4:
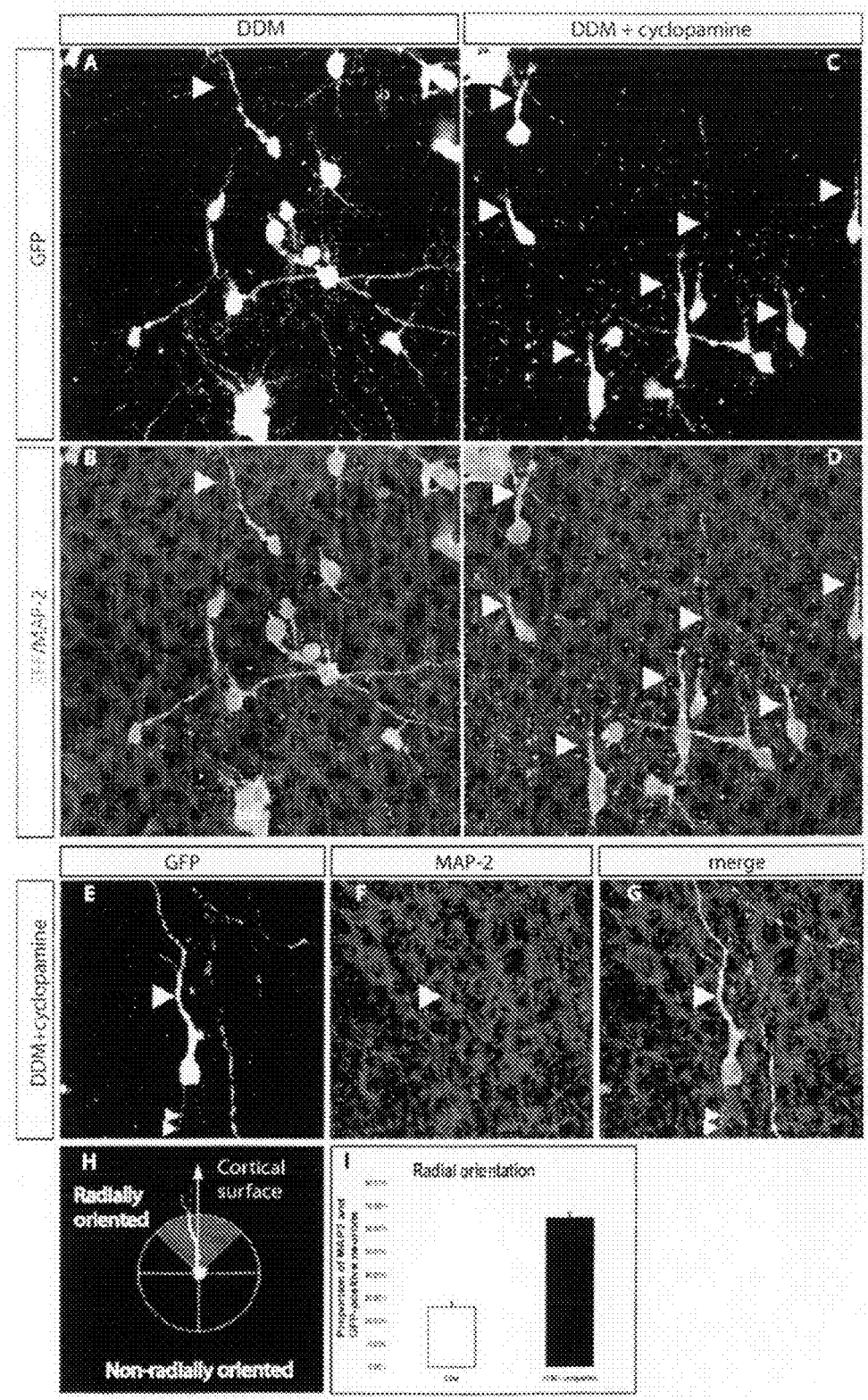

(E) PMI distribution of neurons derived from ES cells in DDM (white bars) or DDM+cyclo (black bars) conditions. Note the shift of the distribution towards higher PMIs in DDM+cyclo conditions. Y-axis denotes proportion of cells having the respective PMI values (F) Proportion of neurons displaying a PMI above the cut off of 1.2 after DDM (white bar) or DDM+cyclo (black bar) conditions, showing a conversion to a pyramidal morphology in DDM+cyclo. Y-axis denotes proportion of MAP2 positive neurons having the above cut-off PMI value FIG. 4 illustrates that neurons derived from ES cells in DDM+cyclo behave like cortical neurons when grafted in postnatal cortex.

Orientation pattern of neurons derived from eGFP+ES cells in DDM (A,B) or DDM+cyclo (C-G) conditions, differentiated for 28 days, and cultured for 3 days on top of postnatal cortical slices. GFP in (B,D,G) gives the more intense signal than the background MAP2 staining. Apical surface of the cortical slices are up. Dendrites that are located apically and oriented radially (marked by arrowheads) are much more prevalent in the DDM+cyclo condition. Basal axon extending radially is marked by small arrowheads in (E-G). (H,I) Quantification of the proportion of neurons displaying radial orientation (defined as a angle of orientation of less than 45° compared to the radius of the cortex) for neurons derived in DDM (white bar) or DDM+cyclo (black bar) conditions. Data are represented as mean+/−S.E.M.

FIG. 5 schematically illustrates the various cortical markers used herein, their endogenous layer-specific pattern, and their timing of generation in vivo (adapted from Hevner et al. 2003. Dev Neurosci 25: 139-151; and von Economo C & Koskinas G 1925. The Cytoarchitectonics Of The Adult Human Cortex. Julius Springer Verlag, Vienna).

FIG. 6 illustrates that the temporal pattern of generation of the different subtypes of cortical neurons from ES cells differentiated in DDM+cyclo is similar to the in vivo situation.

(A) Evolution in time of the proportion of Tuj1+ neurons expressing layer-specific markers of distinct subtypes of cortical neurons following DDM+cyclo differentiation. Arrows indicate the first day of appearance of each marker in neurons during the course of differentiation. Note the distinct waves of neuronal generation, from an early wave of generation of reelin+/Tbr1+Cajal-Retzius neurons, to reelin-/Tbr1+ presumptive layer VI neurons, to CITP2+ or Ox1+ presumptive layer V neurons, to Satb2+ presumptive layer II/III/IV neurons. Data are represented as mean+/−S.E.M. (N=3 experiments). X-axis denotes days of differentiation. Y-axis denotes proportion of neurons positive for the respective markers.

(B) Some neurons derived from ES cells in DDM+cyclo conditions behave like Cajal-Retzius neurons when grafted in the marginal zone of the postnatal cortex. GFP is more intense than the background MAP2 staining. Apical surface of the cortical slices are up.

Figure 7:
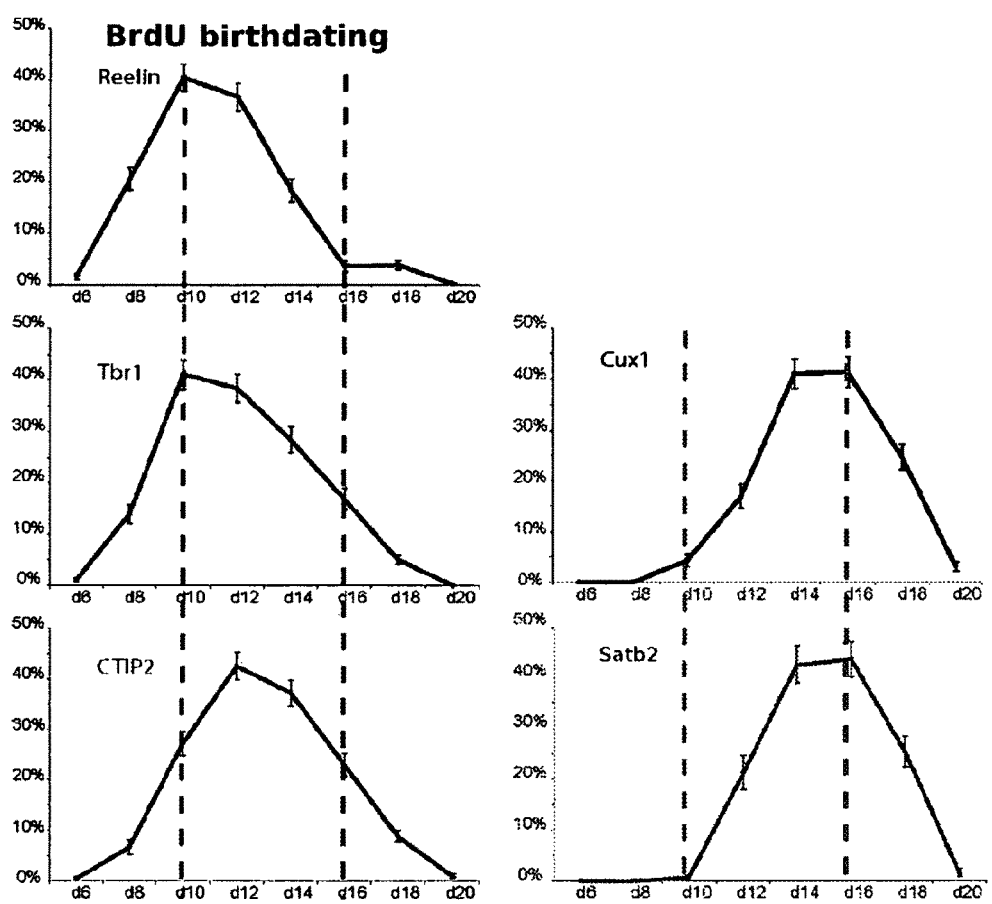

FIG. 7 illustrates birthdating analysis. Cultures were pulse labelled with BrdU for 24 hours at various time points (X axis), cultures were stopped at day 21, and the proportion of BrdU fully labelled nuclei was quantified among Tuj1+ neurons expressing each specific marker (reelin, Tbr1, CTIP2, Cux1, or Satb2). Note the gradual temporal shift of onset and peak of neurogenesis for each neuronal population. Data are represented as mean+/−S.E.M. (N=3 experiments). X-axis denotes days of BrdU pulse. Y-axis denotes proportion of BrdU-labelled neurons.

Figure 8:
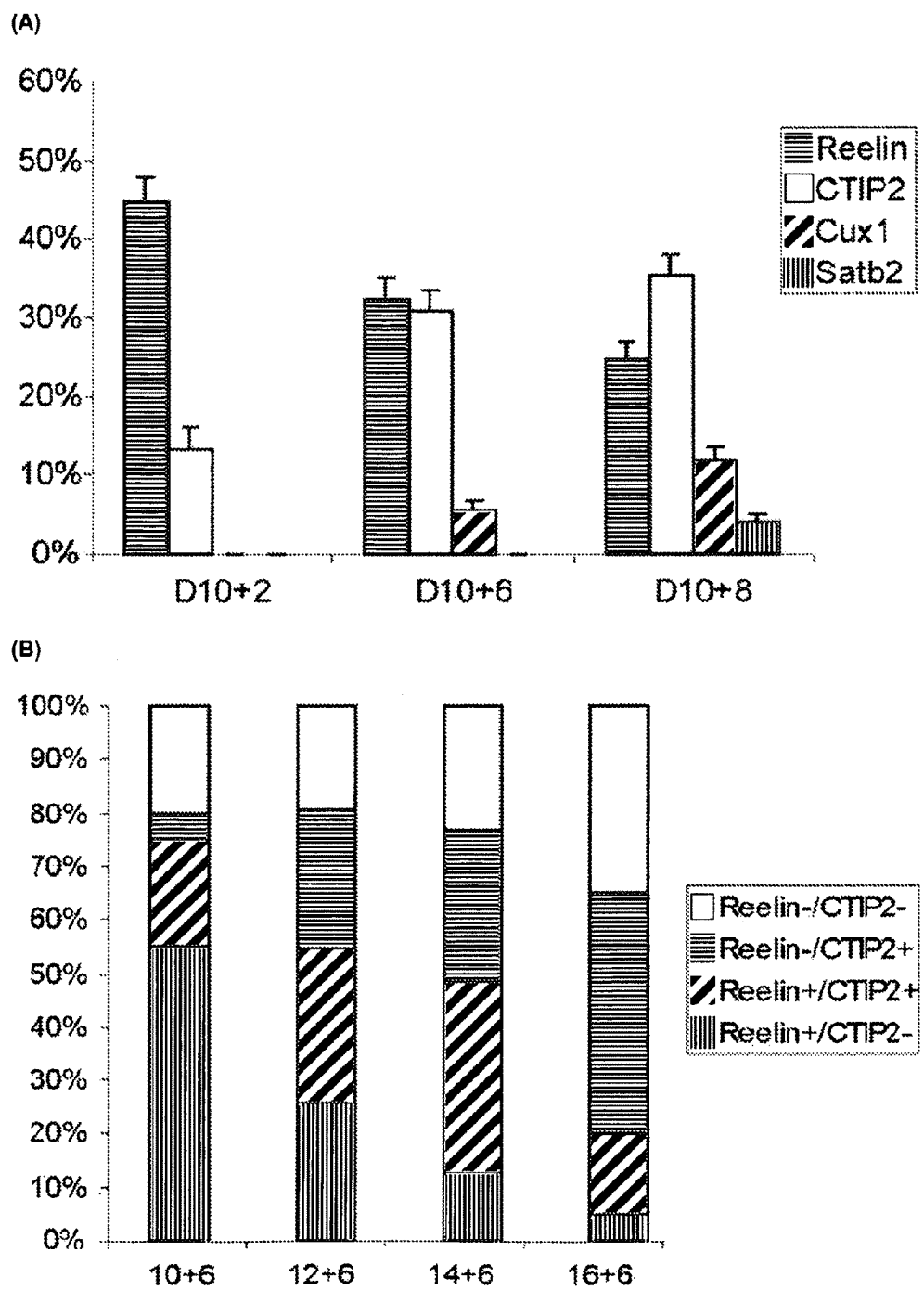

FIG. 8(A) illustrates clonal analysis revealing that the temporal pattern of neurogenesis from ES cells to cortical neurons is encoded within single lineages of neural progenitors. Neural progenitors generated from ES cells were dissociated after 10 days of differentiation, followed by culture at clonal density for 2, 6, or 8 days. The proportion of Tuj1+ neurons expressing reelin, CTIP2, Cux1 and Satb2 was then quantified. Data are represented as mean+/−S.E.M. (N=3 experiments). X-axis denotes days of differentiation. Y-axis denotes proportion of neurons positive for the respective markers.

FIG. 8(B) illustrates clonal analysis revealing the shift in competence of individual neural progenitors. Neural progenitors from ES cells were dissociated at distinct time points (days 10, 12, 14, and 16 of differentiation), and then cultured for 6 days at clonal density, revealing a shift in competence from clones of early progenitors generating mainly reelin+ neurons, to clones of later progenitors generating mainly CTIP2+ neurons. Values represent the mean number of clones containing at least one marked neuron. X-axis denotes days of differentiation. Y-axis denotes proportion of clones with the respective marker expression.

Figure 9:
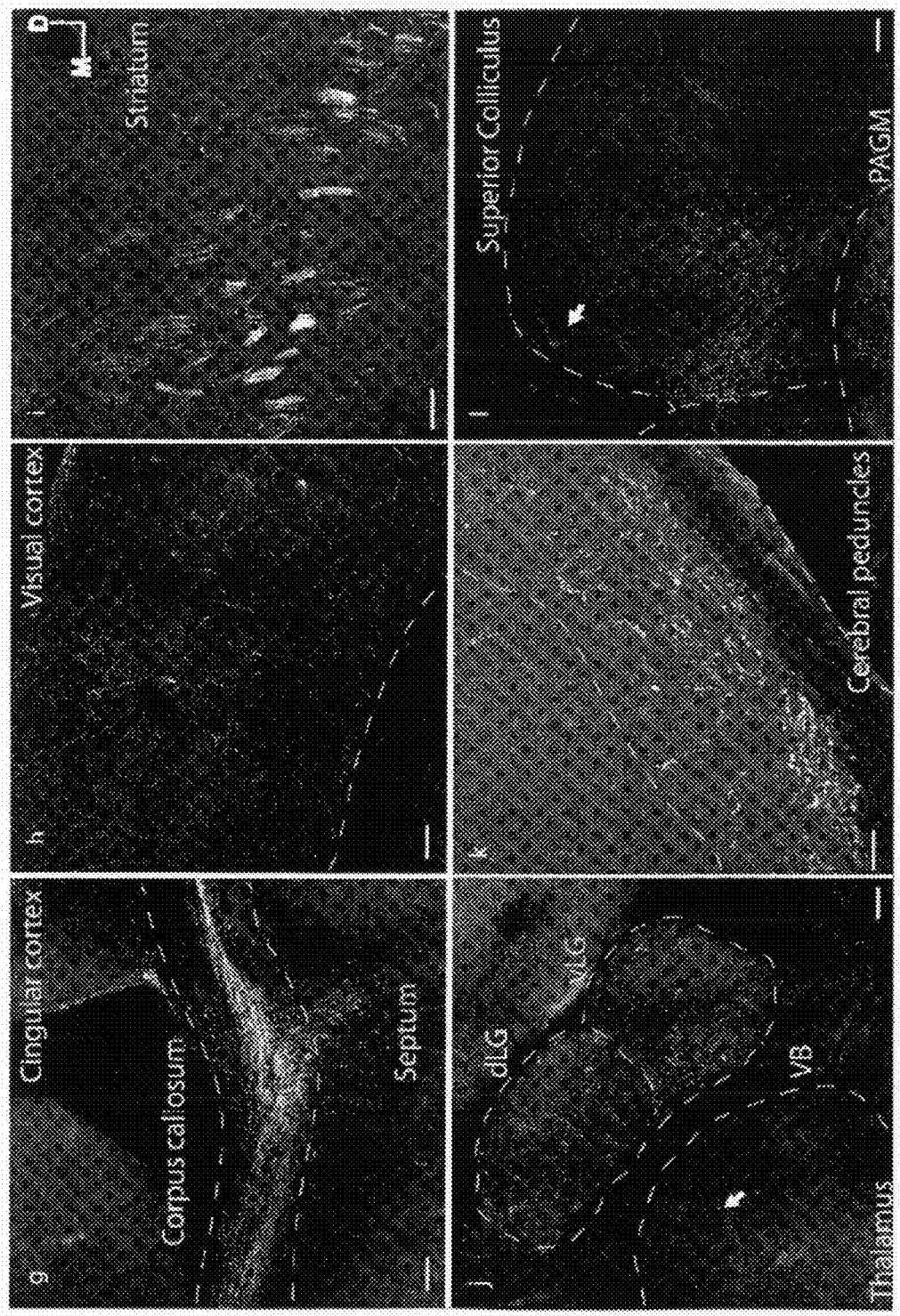
Figure 10:
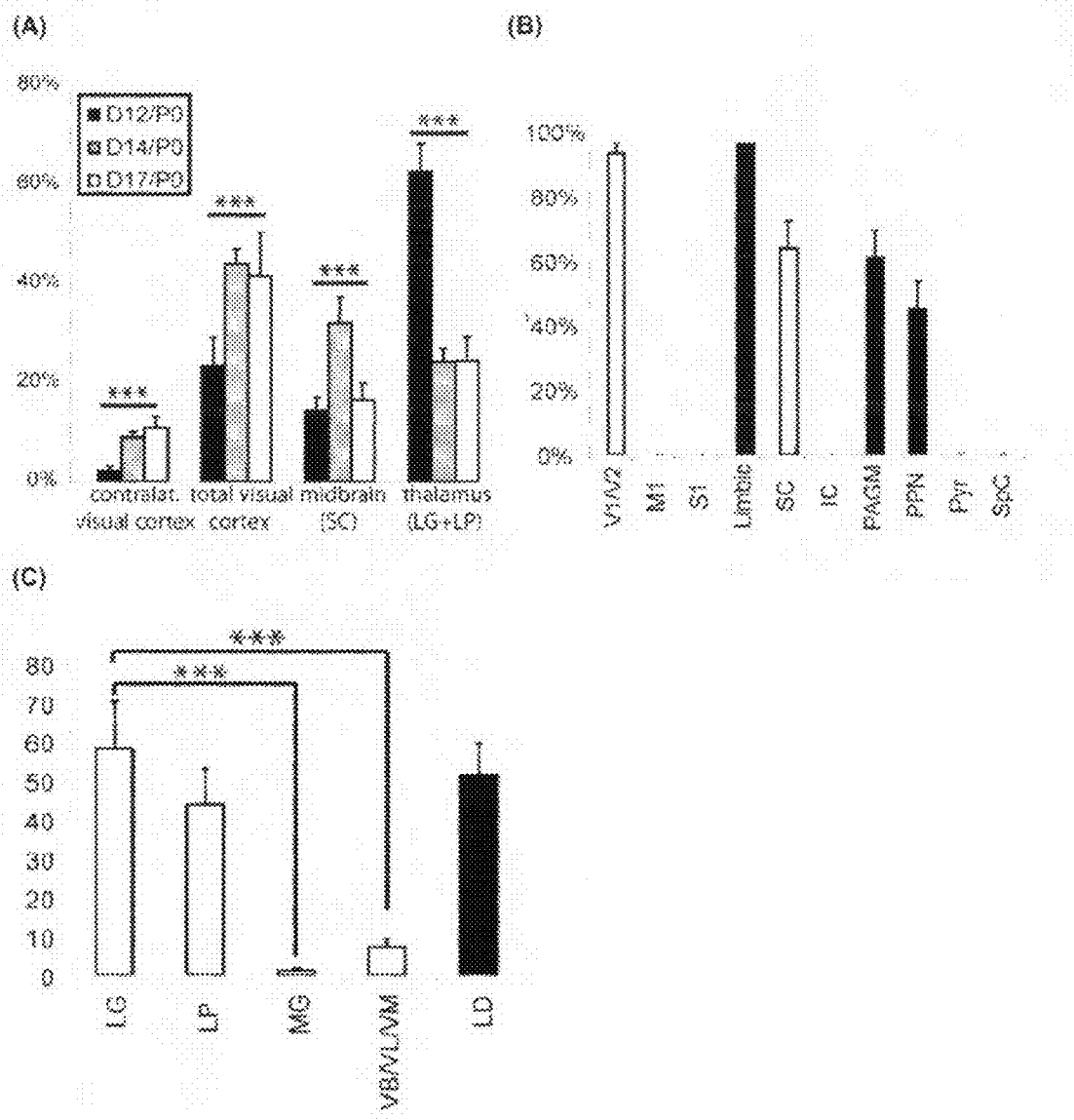
Figure 11:
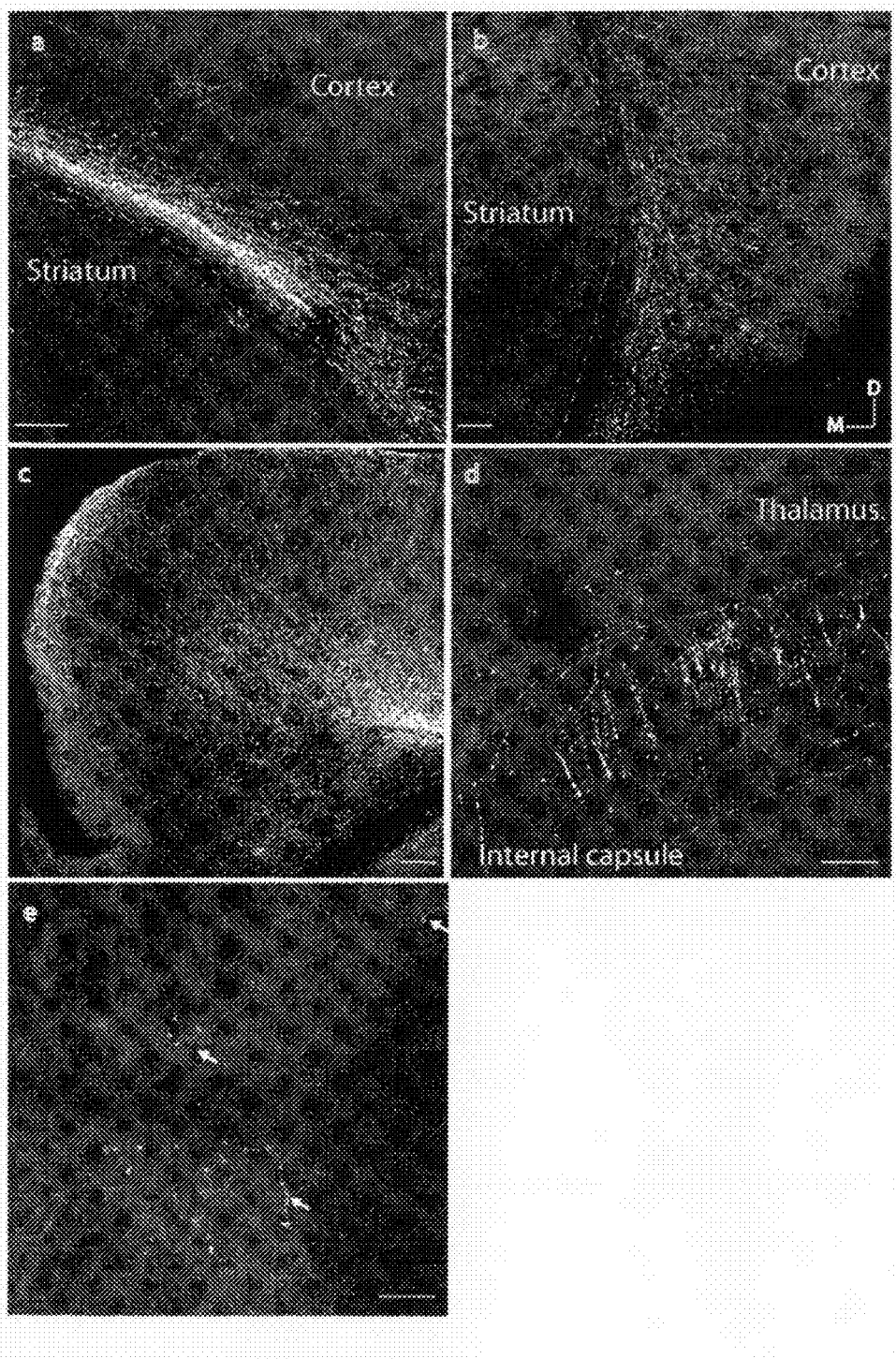

FIGS. 9-11 illustrate ES cells expressing GFP under the Tau promoter that were differentiated in vitro for 12-17 days, and then grafted into the frontal cortex of neonatal mice:

FIG. 9 (*a*) Schematic representation of the grafting protocol. ES-derived neurons and progenitors were injected under the motor cortex. (b, c) Representative case of a graft located in the motor cortex next to the striatum and lateral ventricle (LV), surrounded by some scattered neurons. Most of the cells are GFP-positive (b) and MAP-2-positive (c). (d) Representative case of single GFP-positive neurons found inside the cortex. Note the typical pyramidal morphology and radial orientation.

FIG. 9 (*e, f*) illustrates schematic representation of the layer- and area-specific endogenous patterns of connectivity of layer VI (e) and layer V (f) neurons, from motor (M), somatosensory (S), auditory (A), and visual (V) areas. (e) Layer VI neurons in all areas project mainly to the thalamic nuclei but show area-dependent intrathalamic specificity of connectivity: motor to the ventrolateral (VL) nucleus, somatosensory to the ventrobasal (VB) nucleus, auditory to the medial geniculate (MG) nucleus and visual to the lateral geniculate (LG) nucleus (other visual targets LD/LP are not shown). (f) Layer V neurons in all areas project to more caudal structures and also show area-dependent specificity of connectivity: motor to the caudal pediculopontine nuclei (PPN) and the spinal cord, auditory to the inferior colliculus, and visual to the superior colliculus and the rostral PPN.

FIG. 9 (g-l) Patterns of projections of the grafted neurons as determined by GFP staining 1 month after grafting. Projections were found in the corpus callosum (g), the visual cortex (h), the internal capsule, the striatum (i), the thalamus (j), with fibres located almost exclusively in dLG and vLG but very few in the VB (arrow in j), the cerebral peduncles (k) and finally the superior colliculus, including its most superfical part (arrow) (l).

Scale bars in FIG. 9: (d): 20 µm; (b, c, i, k): 50 µm; FIG. 9 (g, h, j, l): 100 µm. Dorsal is up and medial is left in all panels.

FIG. 10 (A) illustrates quantification of the proportion of fibres found in layer-specific targets, emanating from grafted cells differentiated for different time periods (12, 14, 17 days) in vitro. Increasing the time of differentiation yields more cortico-cortical fibers and cortico-tectal fibers but less cortico-thalamic fibers (*** is p<0.001 for comparison of the 3 time points for each target, N=30). Y-axis denotes proportion of axonal projections.

FIG. 10 (B, C) illustrates quantification of the area-specificity of the projections of the grafted neurons. (B) Quantification of the proportion of grafted animals (N=30) displaying GFP+ fibres in different cortical areas and subcortical targets: visual (V1), motor (M1), somatosensory (S1) and limbic cortices, midbrain/hindbrain: superior and inferior colliculi (SC and IC), pediculopontine nuclei (PPN), periaqueductal grey matter (PAGM), pyramidal tracts (Pyr) and spinal cord (SpC). Y-axis denotes proportion of animals displaying axonal growth. (C) Quantification of the number of fibres found in selective thalamic nuclei: lateral geniculate (LG), medial geniculate (MG), ventrobasal, ventrolateral and ventromedial (VBNUVM), laterodorsal (LD), lateroposterior (LP), anterior group (Ant), mediodorsal group (MD). Values are shown as means+/−S.E.M. (N=30 animals). Targets of the visual cortex are represented inter alia by V1/V2, SC, LG and LP, targets of motor/somatosensory/auditory areas are represented inter alia by MG, VB/VL/VM; diffuse/limbic targets are labelled in black. Values are displayed as means±SEM of counted fibres (N=28 animals; *** is p<0.001). Y-axis denotes mean number of axons.

FIG. 11 illustrates that ES cell derived neurons display layer-specific and area-specific patterns of neuronal projections when grafted in vivo. ES cells expressing GFP under the Tau promoter were differentiated in vitro for 12-17 days, then grafted into the frontal cortex of neonatal mice. Patterns of projections were determined by GFP staining 1 month later. Pictures show projections through the external capsule (a), to the limbic cortex: perirhinal cortex (b) and retrosplenial cortex (c), the internal capsule underlying the thalamus (d) and the pediculopontine nuclei (e). Scale bars represent 100 µm (a-c) or 50 µm (d,e). Dorsal is up and medial is left in all figures.

Figure 12:
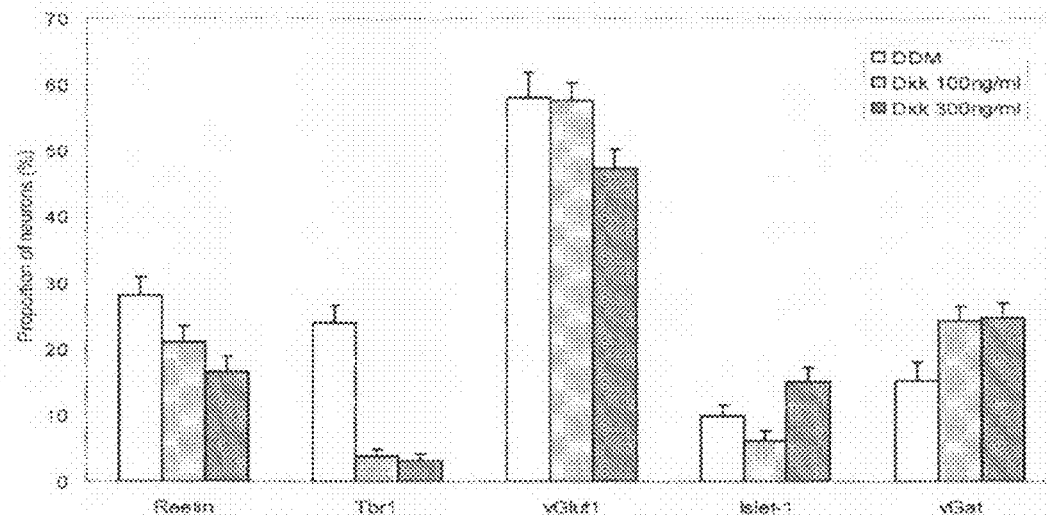

FIG. 12 illustrates that neural progenitors and neurons of ventral telencephalic identity (including cortical interneurons, striatal interneurons, striatal projections neurons) can be generated from ES cells following DDM+Shh (at 1-10 µM) or DDM+DDK Wnt inhibitor (at 100-300 ng/ml), or a combination of both (at 1 µM/100 ng/ml respectively). (A) Proportion of Nestin positive neural progenitors expressing specific neural regionalization markers following 14 days of differentiation in DDM or DDM+Shh or DDM+DKK. (B), (C) Proportion of VgluT1, VgluT2 and vGAT, and reelin, Tbr1, Isl1 among Tuj1 positive neurons after 21 days of differentiation in DDM alone or DDM+Shh or DDM+DKK, or DDM+Shh/DKK.

DETAILED DESCRIPTION OF THE INVENTION

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps.

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

All documents cited in the present specification are hereby incorporated by reference in their entirety. In particular, the teachings of all documents herein specifically referred to are incorporated by reference.

The discussion of the background to the invention herein is included to explain the context of the present invention. This is not to be taken as an admission that any of the material referred to was published, known, or part of the common general knowledge in any country as of the priority date of any of the claims.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention. When specific terms are defined in connection with a particular aspect or embodiment, such connotation is meant to apply throughout this specification, i.e., also in the context of other aspects or embodiments, unless otherwise defined.

For general methods relating to the invention, reference is made inter alia to well-known textbooks, including, e.g., "Molecular Cloning: A Laboratory Manual, 2nd Ed." (Sambrook et al., 1989), Animal Cell Culture (R. I. Freshney, ed., 1987), the series Methods in Enzymology (Academic Press), Gene Transfer Vectors for Mammalian Cells (J. M. Miller & M. P. Calos, eds., 1987); "Current Protocols in Molecular Biology and Short Protocols in Molecular Biology, 3rd Ed." (F. M. Ausubel et al., eds., 1987 & 1995); Recombinant DNA Methodology II (R. Wu ed., Academic Press 1995).

General techniques in cell culture and media uses are outlined inter alia in Large Scale Mammalian Cell Culture (Hu et al. 1997. Curr Opin Biotechnol 8: 148); Serum-free Media (K. Kitano. 1991. Biotechnology 17: 73); or Large Scale Mammalian Cell Culture (Curr Opin Biotechnol 2: 375, 1991), incorporated by reference herein.

For further elaboration of general techniques useful in the practice of this invention, the practitioner can refer to standard textbooks and reviews in cell biology, tissue culture, and embryology. Included are inter alia "Teratocarcinomas and embryonic stem cells: A practical approach" (E. J. Robertson, ed., IRL Press Ltd. 1987); "Guide to Techniques in Mouse Development" (P. M. Wasserman et al. eds., Academic Press 1993); "Embryonic Stem Cells: Methods and Protocols" (Kursad Turksen, ed., Humana Press, Totowa N.J., 2001); "Embryonic Stem Cell Differentiation in Vitro" (M. V. Wiles, Meth. Enzymol. 225: 900, 1993); "Properties and uses of Embryonic Stem Cells: Prospects for Application to Human Biology and Gene Therapy" (P. D. Rathjen et al., al., 1993). Differentiation of stem cells is reviewed, e.g., in Robertson. 1997. Meth Cell Biol 75: 173; Roach and McNeish. 2002. Methods Mol Biol 185: 1-16; and Pedersen. 1998. Reprod Fertil Dev 10: 31, incorporated by reference herein.

As noted, methods of the invention can generate neural progenitors or mature neuron like cells departing from undifferentiated mammalian pluripotent stem (mPS) cells.

The terms "progenitor" or "precursor" refer generally to an unspecialised or relatively less specialised and proliferation-competent cell which can under appropriate conditions give rise to at least one relatively more specialised cell type, such as inter alia to relatively more specialised progenitor cells or eventually to terminally differentiated cells, i.e., fully specialised cells that may be post-mitotic.

The term "neural progenitor" or "neural precursor" refers to a progenitor cell that can under appropriate conditions give rise exclusively or predominantly to one or more cell types of the neural system, such as to neurons and/or glia.

The term "stem cell" refers to a progenitor as defined herein further capable of self-renewal, i.e., which can under appropriate conditions proliferate without differentiation. The term encompasses stem cells capable of substantially unlimited self-renewal, i.e., wherein at least a portion of the stem cell's progeny substantially retains the unspecialised or relatively less specialised phenotype, the differentiation potential, and the proliferation capacity of the mother stem cell; as well as stem cells which display limited self-renewal, i.e., wherein the capacity of the stem cell's progeny for further proliferation and/or differentiation is demonstrably reduced compared to the mother cell.

As used herein, the qualifier "pluripotent" denotes a stem cell capable of giving rise to cell types originating from all three germ layers of an organism, i.e., mesoderm, endoderm, and ectoderm, and potentially capable of giving rise to any and all cell types of an organism, although not able of growing into the whole organism.

A progenitor or stem cell is said to "give rise" to another, relatively more specialised cell when, for example, the progenitor or stem cell differentiates to become said other cell without previously undergoing cell division, or if said other cell is produced after one or more rounds of cell division and/or differentiation of the progenitor or stem cell.

The term "mammalian pluripotent stem cell" or "mPS" cell generally refers to a pluripotent stem cell of mammalian origin. The term "mammal" refers to any animal classified as such, including, but not limited to, humans, domestic and farm animals, zoo animals, sport animals, pet animals, companion animals and experimental animals, such as, for example, mice, rats, hamsters, rabbits, dogs, cats, guinea pigs, cattle, cows, sheep, horses, pigs and primates, e.g., monkeys and apes.

In an embodiment, the mPS cells may be derived from a non-human mammal. For example, in an embodiment the mPS cells may be derived from a laboratory animal, preferably from mouse, rat, hamster or rabbit, more preferably mouse. In another preferred embodiment, the mPS cells may be derived from pig. In yet another preferred embodiment, the mPS cells may be derived from primate, such as from non-human primate. In yet another preferred embodiment, the mPS cells may be derived from human.

Prototype mPS cell is a pluripotent stem cell derived from any kind of mammalian embryonic tissue, e.g., embryonic, foetal or pre-foetal tissue, the cell being capable under appropriate conditions of producing progeny of different cell types that are derivatives of all three germinal layers, i.e., endoderm, mesoderm, and ectoderm, according to a standard art-accepted test, such as inter alia the ability to form a teratoma in SCID mice, or the ability to form identifiable cells of all three germ layers in tissue culture.

Included in the definition of mPS cells are thus embryonic stem cells of various types, exemplified without limitation by murine embryonic stem cells, e.g., as described by Evans & Kaufman 1981 (Nature 292: 154-6) and Martin 1981 (PNAS 78: 7634-8); rat pluripotent stem cells, e.g., as described by Iannaccone et al. 1994 (Dev Biol 163: 288-292); hamster embryonic stem cells, e.g., as described by Doetschman et al. 1988 (Dev Biol 127: 224-227); rabbit embryonic stem cells, e.g., as described by Graves et al. 1993 (Mol Reprod Dev 36: 424-433); porcine pluripotent stem cells, e.g., as described by Notarianni et al. 1991 (J Reprod Fertil Suppl 43: 255-60) and Wheeler 1994 (Reprod Fertil Dev 6: 563-8); sheep embryonic stem cells, e.g., as described by Notarianni et al. 1991 (supra); bovine embryonic stem cells, e.g., as described by Roach et al. 2006 (Methods Enzymol 418: 21-37); human embryonic stem (hES) cells, e.g., as described by Thomson et al. 1998 (Science 282: 1145-1147); human embryonic germ (hEG) cells, e.g., as described by Shamblott et al. 1998 (PNAS 95: 13726); embryonic stem cells from other primates such as Rhesus stem cells, e.g., as described by Thomson et al., 1995 (PNAS 92:7844-7848) or marmoset stem cells, e.g., as described by Thomson et al. 1996 (Biol Reprod 55: 254-259).

Other types of mPS cells are also included in the term as are any cells of mammalian origin capable of producing progeny that includes derivatives of all three germinal layers, regardless of whether they were derived from embryonic tissue, foetal tissue or other sources. mPS cells are not derived from a malignant source. A cell or cell line is from a "non-malignant source" if it was established from primary tissue that is not cancerous, nor altered with a known oncogene. It may be desirable, but not always necessary, that the mPS maintain a normal karyotype throughout prolonged culture under appropriate conditions. It may also be desirable, but not always necessary, that the mPS maintain substantially indefinite self-renewal potential under appropriate in vitro conditions.

As noted, prototype "human ES cells" are described by Thomson et al. 1998 (supra) and in U.S. Pat. No. 6,200,806. The scope of the term covers pluripotent stem cells that are derived from a human embryo at the blastocyst stage, or before substantial differentiation of the cells into the three germ layers. ES cells, in particular hES cells, are typically derived from the inner cell mass of blastocysts or from whole blastocysts. Derivation of hES cell lines from the morula stage has been documented and ES cells so obtained can also be used in the invention (Strelchenko et al. 2004. Reproductive BioMedicine Online 9: 623-629). As noted, prototype "human EG cells" are described by Shamblott et al. 1998 (supra). Such cells may be derived, e.g., from gonadal ridges and mesenteries containing primordial germ cells from foetuses. In humans, the foetuses may be typically 5-11 weeks post-fertilisation.

Those skilled in the art will appreciate that, except where explicitly required otherwise, the term mPS cells may include primary tissue cells and established lines that bear phenotypic characteristics of the respective cells, and derivatives of such primary cells or cell lines that still have the capacity of producing progeny of each of the three germ layers.

Exemplary but non-limiting established lines of human ES cells include lines which are listed in the NIH Human Embryonic Stem Cell Registry (http://stemcells.nih.gov/research/registry), and sub-lines thereof, such as, lines hESBGN-01, hESBGN-02, hESBGN-03 and hESBGN-04 from Bresagen Inc. (Athens, Ga.), lines Sahlgrenska 1 and Sahlgrenska 2 from Cellartis AB (Goteborg, Sweden), lines HES-1, HES-2, HES-3, HES-4, HES-5 and HES-6 from ES Cell International (Singapore), line Miz-hES1 from MizMedi Hospital (Seoul, Korea), lines I 3, I 3.2, I 3.3, I 4, I 6, I 6.2, J 3 and J 3.2 from Technion—Israel Institute of Technology (Haifa, Israel), lines HSF-1 and HSF-6 from University of California (San Francisco, Calif.), lines H1, H7, H9, H13, H14 of Wisconsin Alumni Research Foundation/WiCell Research Institute (Madison, Wis.), lines CHA-hES-1 and CHA-hES-2 from Cell & Gene Therapy Research Institute/Pochon CHA University College of Medicine (Seoul, Korea), lines H1, H7, H9, H13, H14, H9.1 and H9.2 from Geron Corporation (Menlo Park, Calif.), lines Sahlgrenska 4 to Sahlgrenska 19 from GOteborg University (Göteborg, Sweden), lines MB01, MB02, MB03 from Maria Biotech Co. Ltd. (Seoul, Korea), lines FCNCBS1, FCNCBS2 and FCNCBS3 from National Centre for Biological Sciences (Bangalore, India), and lines RLS ES 05, RLS ES 07, RLS ES 10, RLS ES 13, RLS ES 15, RLS ES 20 and RLS ES 21 of Reliance Life Sciences (Mumbai, India). Other exemplary established hES cell lines include those deposited at the UK Stem Cell Bank (http://www.ukstemcellbank.org.uk/), and sub-lines thereof, e.g., line WT3 from King's College London (London, UK) and line hES-NCL1 from University of Newcastle (Newcastle, UK) (Strojkovic et al. 2004. Stem Cells 22: 790-7). Further exemplary ES cell lines include lines FC018, AS034, AS034.1, AS038, SA111, SA121, SA142, SA167, SA181, SA191, SA196, SA203 and SA204, and sub-lines thereof, from Cellartis AB (Göteborg, Sweden).

Further within the term mammalian pluripotent stem cells are such mPS cells obtainable by manipulation, such as inter alia genetic and/or growth factor mediated manipulation, of non-pluripotent mammalian cells, such as somatic and particularly adult somatic mammalian cells, including the use of induced pluripotent stem (iPS) cells, as taught inter alia by Yamanaka et al. 2006 (Cell 126: 663-676) and Yamanaka et al. 2007 (Cell 131: to 861-872).

A skilled person will appreciate that further cell lines having characteristics of mammalian, esp. mouse or human, pluripotent cells, esp. ES cells or EG cells, may be established in the future, and these may too be suitable in the present invention. A skilled person can also use techniques known in the art to verify that any established or yet to be established mPS cell lines, or sub-lines thereof, show desirable cell characteristics, such as expansion in vitro in undifferentiated state, preferably normal karyotype and ability of pluripotent differentiation.

mPS cells or cell lines or cultures thereof are described as "undifferentiated" when a substantial proportion (for example, at least 60%, preferably at least 70%, even more preferably at least 80%, still more preferably at least 90% and up to 100%) of cells in the stem cell population display characteristics (e.g., morphological features or markers) of undifferentiated mPS cells, clearly distinguishing them from cells undergoing differentiation. Undifferentiated mPS cells are generally easily recognised by those skilled in the art, and may appear in the two dimensions of a microscopic view with high nuclear/cytoplasmic ratios and prominent nucleoli. It is understood that colonies of undifferentiated cells within the population may often be surrounded by neighbouring cells that are more differentiated. Nevertheless, the undifferentiated colonies persist when the population is cultured or passaged under appropriate conditions known per se, and individual undifferentiated cells constitute a substantial proportion of the cell population. Undifferentiated mPS cells may express the stage-specific embryonic antigens (SSEA) 3 and 4, and markers detectable using antibodies designated Tra-1-60 and Tra-1-81 (Thomson et al. 1998, supra). Undifferentiated mPS cells may also typically express Oct-4 and TERT.

Within the present specification, the terms "differentiation", "differentiating" or derivatives thereof denote the process by which an unspecialised or relatively less specialised cell, such as, for example, mPS cell or progeny thereof, becomes relatively more specialised. In the context of cell ontogeny, the adjective "differentiated" is a relative term. Hence, a "differentiated cell" is a cell that has progressed further down a certain developmental pathway than the cell it is being compared with. The differentiated cell may, for example, be a terminally differentiated cell, i.e., a fully specialised cell capable of taking up specialised functions in various tissues or organs of an organism, which may but need not be post-mitotic; or the differentiated cell may itself be a progenitor cell within a particular differentiation lineage which can further proliferate and/or differentiate. A relatively more specialised cell may differ from an unspecialised or relatively less specialised cell in one or more demonstrable phenotypic characteristics, such as, for example, the presence, absence or level of expression of particular cellular components or products, e.g., RNA, proteins or other substances, activity of certain biochemical pathways, morphological appearance, proliferation capacity and/or kinetics, differentiation potential and/or response to differentiation signals, electrophysiological behaviour, etc., wherein such characteristics signify the progression of the relatively more specialised cell further along the said developmental pathway.

An initial step of the present methods, in particular step a) of above aspects A1 to A4, involves plating of undifferentiated mPS cells onto a substrate which allows adherence of cells thereto. Hence, the methods of the invention involve direct differentiation of mPS cells in an adherent culture rather than initially differentiating the cells through embryoid bodies (suspension culture).

The terms "plating", "seeding" or "inoculating" generally refer to introducing a cell population into an in vitro environment capable of promoting the survival and/or growth of the introduced cells. Typically, said environment may be provided in a system suitably delimited from the surroundings, such as in a culture vessel known per se, e.g., cell culture flask, well plate or dish. Said environment comprises at least a medium, typically a liquid medium, which supports the survival and/or growth of the cells. The medium may be fresh, i.e., not previously used for culturing of cells, or may comprise at least a portion conditioned by prior culturing of cells therein, e.g., culturing of the cells which are being plated or antecedents thereof, or culturing of cells unrelated to the cells being plated.

mPS cells grown without differentiation typically form colonies on an adherent substrate. To allow for plating of so-grown mPS cells, they may be detached from said substrate and at least partly dissociated from one another, so as to obtain a dispersion of mPS cells and/or clumps or clusters thereof usually in an isotonic buffer (e.g., PBS or Hanks balanced salt solution) or medium. Appropriate ways of detaching and dissociating adherent mPS cultures are generally known in the art and may include without limitation treatment with proteolytic enzymes, chelation of bivalent ions, mechanical disintegration, or combinations of any of the above.

Exemplary proteolytic enzymes encompass, e.g., trypsin, collagenase (e.g., collagenase type I, collagenase type II, collagenase type III, or collagenase type IV), elastase, Accutase™ (Innovative Cell Technologies), dispase, pronase, papain, plasmin or plasminogen (WO 1994/03586), which may be used in quantities and at conditions known per se in the art. Trypsin or collagenase may be preferred. Chelation of bivalent ions, primarily of $Ca^{2+}$ and $Mg^{2+}$, may be effected using chelators, such as, e.g., EDTA (ethylenediamine tetraacetic acid) or a di-sodium salt thereof, or EGTA (ethyleneglycerol tetraacetic acid) or a di-sodium salt thereof, using concentrations and conditions known per se. EDTA may be preferred. Exemplary mechanical dissociation of cells may involve repeated passing of cell colonies, clumps or clusters through a small bore pipette (e.g., a 1000 µl micropipette tip) to shear the cell associations. Mechanical cell dissociation may, when used in isolation, lead to cell damage and may thus be advantageously combined with a prior treatment with proteolytic enzymes and/or chelators. A suitable method of cell detachment and dissociation should preserve viability of the cells; preferably, a cell suspension obtained following detachment and dissociation may comprise at least 60% of viable cells, e.g., ≥70%, more preferably ≥80%, and most preferably ≥90% or up to 100% of viable cells.

The detachment and dissociation of mPS cells for subsequent plating can yield a cell suspension comprising individual mPS cells and/or clumps or clusters of mPS cells. For example, the conditions of detachment and dissociation may be such as to provide a cell suspension comprising at least 10%, e.g., at least 20%, at least 30%, at least 40%, preferably at least 50%, e.g., at least 60%, and more preferably at least 70%, e.g., at least 80%, at least 90% or up to 100% of mPS cells as individual cells. Clumps or clusters of mPS cells present in such cell suspension may contain on average, e.g., between >1 and 1000 cells, between 1 and 500 cells, between 1 and 100 cells, between 1 and 50 cells or between 1 and 20 cells, e.g., about 5 cells, about 10 cells or about 15 cells.

Preferably, the undifferentiated mPS cells may be plated at a comparably low density, such as between about $1 \times 10^1$ and about $1 \times 10^5$ cells/cm$^2$, more preferably between about $1 \times 10^2$ and about $5 \times 10^4$ cells/cm$^2$, even more preferably between about $1 \times 10^3$ and about $1 \times 10^4$ cells/cm$^2$, e.g., at about $1 \times 10^3$, about $2 \times 10^3$, about $3 \times 10^3$, about $4 \times 10^3$, about $5 \times 10^3$, about $6 \times 10^3$, about $7 \times 10^3$, about $8 \times 10^3$, or about $9 \times 10^3$ cells/cm$^2$.

As noted, the undifferentiated mPS cells are plated onto a substrate which allows adherence of cells thereto. Hence, the culture system whereto the mPS cells are plated may comprise a surface compatible with cell adhesion, whereby the so-plated mPS cells contact and attach to said substrate surface.

In general, a substrate which allows adherence of cells thereto may be any substantially hydrophilic substrate. In an embodiment, a suitable adherent substrate may be surface-treated (e.g., treated by atmospheric corona discharge, radio frequency vacuum plasma treatment, or DC glow discharge or plasma treatment, as known in the art) tissue culture plastic, which may typically display polar and/or hydrophilic chemical moieties, such as, e.g., amines, amides, carbonyls, carboxylates, esters, hydroxyls, sulfhydryls and the like. In an alternative embodiment, a suitable adherent substrate may be glass, optionally surface-treated to introduce functional groups such as listed above to increase the hydrophilicity. Further adherent substrates may be generated via surface-coating of, for example, tissue-culture plastic or glass, with hydrophilic substances. In an example, said coating may involve suitable poly-cations, such as, e.g., poly-ornithine or poly-lysine. In other examples, preferred coating may comprise one or more components of extracellular matrix, e.g., the ECM proteins fibrin, laminin, collagen (preferably collagen type 1), gelatine, glycosaminoglycans (e.g., heparin or heparan sulphate), fibronectin, vitronectin, elastin, tenascin, aggrecan, agrin, bone sialoprotein, cartilage matrix protein, fibrinogen, fibulin, mucins, entactin, osteopontin, plasminogen, restrictin, serglycin, SPARC/osteonectin, versican, thrombospondin 1, or cell adhesion molecules including cadherins, connexins, selectins, by themselves or in various combinations.

A particularly preferred example of adherent substrate surface for plating undifferentiated mPS cells according to the invention comprises or consists of gelatine. The term "gelatine" as used herein refers to a heterogeneous mixture of water-soluble proteins of high average molecular weight derived from the collagen-containing parts of animals, such as skin, bone and ossein by hydrolytic action, usually either acid hydrolysis or alkaline hydrolysis. The term "gelatine" also encompasses suitable chemical derivatives thereof such as acetylated gelatine or cross-linked gelatine. Protocols for surface treatment of tissue culture surfaces with gelatine are known in the art. By means of illustration and not limitation, culture vessels may be treated for 2 hours or longer, e.g., for 24 hours, with 0.02%-1% (w/v), typically with about 0.1% (w/v) gelatine in, e.g., distilled and preferably sterilised water.

Typically, after plating of the undifferentiated mPS cells, the cell suspension is left in contact with the adherent surface to allow for adhesion of mPS cells from the plated cell population to said substrate.

In embodiments, the mPS cell suspension may be contacted with the adherent surface for at least about 0.5 h, e.g., for about ≥1 h, preferably for about ≥2 h, for about ≥4 h, more preferably for about ≥8 h, e.g., for about ≥12 h, even more preferably for about ≥16 h, e.g., for about ≥20 h, and most preferably for about 24 h or more, e.g., for at least about 28, 32, 36, 40, 44 or 48 h. In further preferred embodiments, the mPS cell suspension may be contacted with the adherent surface for between about 2 h and about 48 h, e.g., for about 12 h, about 24 h, about 36 h or for about 48 h. Although longer contacting times (before removal of the non-adherent matter) are possible, they are in general not necessary.

After mPS cells are allowed to attach to the adherent substrate, non-adherent matter is typically removed from the culture system. Non-adherent matter may comprise, for example, cells that have not attached to the adherent substrate, non-viable or dead cells, cell debris, etc. Non-adherent matter may be suitably removed by exchanging medium within the culture system, optionally including one or more washes of the attached cells with suitable medium or isotonic buffer. Hereby, cells from the undifferentiated mPS suspension which have adhered to the substrate surface are selected for further culturing.

A further step of the present methods, in particular step b) of above aspects A1 to A4, involves culturing the mPS cells which have attached to the adherent substrate in a medium permissive to differentiation of the mPS cells. The term "culturing" commonly refers to maintaining and/or growing of cells.

The term "medium permissive to differentiation of mPS cells" means that the medium does not contain components, in sufficient quantity, which would suppress mPS differentiation or would cause maintenance and/or proliferation of mPS in undifferentiated or substantially undifferentiated state. By means of illustration, such components absent from the medium may include leukaemia inhibitory factor (LIF), basic fibroblast growth factor (b-FGF), and/or embryonic fibroblast feeders or conditioned medium of such feeders, depending on the particular mPS cell type.

In embodiments, the medium may comprise basal medium formulations generally known in the art. Suitable basal media formulations include, without limitation, Minimum Essential Medium (MEM), alpha modified Minimum Essential Medium (alpha-MEM), Basal Medium Essential (BME), Dulbecco's Modified Eagle's Medium (DMEM), F-12 Nutrient Mixture (Ham; see, e.g., Ham 1965. PNAS 53: 288), Neurobasal medium (NM; see, e.g., Brewer et al., 1993. J Neurosci Res 35: 567-76), and the like, which are commercially available (e.g., Invitrogen, Carlsbad, Calif.). Compositions of basal media such as above are known per se and contain ingredients necessary for mammalian cell development. For example, such ingredients may include inorganic salts (preferably at least salts containing Na, K, Mg, Ca, Cl, P, and possibly Cu, Fe, Se and Zn), physiological buffers (e.g., HEPES, bicarbonate or phosphate buffers), amino acids, vitamins, and sources of carbon (e.g. glucose, or pyruvate, e.g., sodium pyruvate), and may optionally also comprise reducing agents (e.g., glutathione), nucleotides, nucleosides and/or nucleic acid bases, ribose, deoxyribose, etc. In addition, the media may be further supplemented with one or more compounds of interest, including without limitation additional L-glutamine, non-essential amino acids, β-mercaptoethanol, protein factors such as insulin, transferrin or bovine serum albumin, antibiotic and/or antimycotic components, such as, e.g., penicillin, streptomycin and/or amphotericin, or other components.

The present methods achieve differentiation of mPS cells into neural progenitors or mature neuron like cells. Media optimised by the inventors thus particularly support survival and/or growth of both mPS cells and the resulting neural cells, in particular neurons.

Accordingly, in a preferred embodiment, basal medium employed in differentiating the mPS cells may be chosen from DMEM, F12 or Neurobasal medium (NM), or any mixture thereof, more preferably from DMEM or F12 or a mixture thereof. In a particularly preferred embodiment, basal medium employed to differentiate the mPS cells is DMEM/F12 mixture, more preferably 1:1, vol/vol.

In a preferred embodiment, a suitable basal medium may comprise further components supporting neural cell survival, more preferably by any one, even more preferably any two or more, and most preferably all components chosen from: insulin, transferrin, progesterone, putrescine and selenite. Preferably, the medium comprises insulin, which as realised by the inventors may particularly facilitate the desired differentiation of mPS cells.

Such components may be preferably present as follows: insulin—usually at final concentration between about 0.1 µM and about 5.0 µM, preferably between about 0.5 µM and about 1.5 µM, more preferably between about 0.8 µM and about 1.0 µM, such as at about 0.85 µM, about 0.9 µM or about 0.95 µM, e.g., at 0.861 µM; transferrin—usually at final concentration between about 1 µM and about 100 µM, preferably between about 2 µM and about 50 µM, more preferably between about 5 µM and about 20 µM, such as at about 10 µM; progesterone—usually at final concentration between about 1 nM and 100 nM, preferably between about 5 nM and about 50 nM, more preferably between about 10 nM and about 30 nM, such as at about 20 nM; putrescine—usually at final concentration between about 10 µM and 1 mM, preferably between about 50 µM and about 500 µM, more preferably between about 50 µM and about 200 µM, even more preferably between about 80 µM and about 120 µM, such as at about 90 µM, about 100 µM or about 110 µM, e.g., 100.1 µM; selenite—usually at final concentration between about 3 nM and about 300 nM, preferably between about 10 nM and about 100 nM, more preferably between about 20 nM and about 50 nM, such as at about 30 nM or about 40 nM, e.g., 30.1 nM.

In a further preferred embodiment, suitable basal medium may be comprise further components supporting neural cell survival, more preferably by any one, even more preferably any two or more, and most preferably all components chosen from: L-glutamine, MEM-nonessential amino acids, sodium pyruvate, beta-mercaptoethanol and Bovine Serum Albumine (preferably Fraction V). Such components may be preferably present as follows: L-glutamine—usually at final concentration between about 0.5 mM and about 10 mM, preferably between about 1 mM and about 5 mM, more preferably about 2 mM; MEM-nonessential amino acids—usually at final concentration of 1×; sodium pyruvate—usually at final concentration between about 0.1 mM and about 10 mM, preferably between about 0.5 mM and about 5 mM, more preferably between about 0.8 mM and about 1.2 mM, such as at about 1 mM; beta-mercaptoethanol—usually at final concentration between about 10 µM and about 1 mM, preferably between about 50 µM and about 500 µM, more preferably between about 80 µM and about 120 µM, such as at about 100 µM or about 110 µM; BSA—usually at final concentration between about 50 µg/ml and about 5 mg/ml, preferably between about 100 µg/ml and about 1 mg/ml, more preferably between about 250 µg/ml and about 750 µg/ml, such as at about 500 µg/ml.

Hence, a suitable basal medium, such as preferably DMEM/F12, may further comprise any one, preferably any two or more, and more preferably all components chosen from: insulin, transferrin, progesterone, putrescine, selenite, L-glutamine, MEM-nonessential amino acids, sodium pyruvate, beta-mercaptoethanol and BSA. Preferably, said medium comprises insulin.

Further components are known to promote neuronal survival and may be supplied to the present media during the induction of neuronal differentiation of mPS cells or after said differentiation has commenced or at least partly progressed (e.g., preferably at between t=10 days and t=14 days; wherein t=0 days is deemed throughout this specification to be the moment when the mPS cells are first exposed to a medium permissive to their differentiation). Such components may include without limitation one or more of D-biotin, catalase, L-carnitine, corticosterone, ethanolamine, D-galactose, glutathione (reduced), linoleic acid, linolenic acid, superoxide dismutase, T3-albumin complex, DL-tocopherol or DL-tocopherol acetate; such as, e.g., components of the B27 supplement (see Brewer 1997. J Neurosci Methods 71: 143-55).

In a particularly successful embodiment, mPS cells are first differentiated in DMEM/F12 medium supplemented with at least insulin and preferably also with any one or preferably all of transferrin, progesterone, putrescine, selenite, L-glutamine, MEM-nonessential amino acids, sodium pyruvate, beta-mercaptoethanol and BSA, for up to t=20 days, preferably for up to t=16 days, and more preferably for up to between t=7 days and t=14 days, even more preferably for up to between t=7 days and t=14 days, where after the medium is changed (optionally upon passaging of the cells) for a rich medium capable of supporting neuronal survival, such as, preferably N2B27 medium.

As noted, methods of the present aspects involve exposing the mPS cells during at least part of culturing in differentiation-permissive conditions (in step b) to either an antagonist of the SHH signalling pathway; or to an SHH agonist and/or an antagonist of the Wnt signalling pathway.

As used herein, "sonic hedgehog antagonist" refers to any natural or synthetic substance that decreases, inhibits or abolishes the activity of SHH-signalling pathway, either directly by affecting a protein in the SHH signalling pathway; preferably involving SHH or its receptors Patched (Ptc), Smoothened (Smo) and/or Gli, or by affecting downstream mediators of SHH signalling.

Without limitation, SHH pathway antagonists may take the form of a chemical or biological substance, a pharmaceutical agent or drug, a specific binding agent such as a neutralising or antagonistic antibody, a nucleic acid molecule or oligonucleotide, or a dominant negative fragment or variant of an SHH pathway protein, e.g., SHH or receptor thereof. For example, SHH pathway antagonist may be a small organic molecule inhibitor, preferably having size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da.

In an embodiment, SHH pathway may be antagonised by reducing the expression of a protein involved therein, preferably of SHH or of its receptor, in particular Ptc, Smo and/or Gli, more preferably Smo, in mPS cells'. This may encompass any extent of reduction of expression, such as, e.g., by ≥10%, e.g., ≥20%, more preferably ≥30%, e.g., ≥40%, yet more preferably ≥50%, e.g., ≥60%, still more preferably ≥70%, e.g., ≥80%, and most preferably by ≥90%, e.g., ≥95% or even about 100%, relative to the basal expression level of the respective protein in the mPS cells; as determined using quantification methods known per se, such as, e.g., ELISA, RIA, immuno-precipitation, Western blotting, etc. Decreasing the expression level of a desired gene product may be achieved by methods known in the art, such as, e.g., by transfecting (e.g., by electroporation, lipofection, etc.) or transducing (e.g., using a viral vector), the cell with an antisense agent, such as, e.g., antisense DNA or RNA oligonucleotide, a construct encoding for an antisense transcript, or an RNAi agent, such as siRNA, shRNA or vectors encoding such, etc.

In an embodiment, SHH pathway may be antagonised by reducing the activity of a protein involved therein, e.g., of SHH or of its receptors such as Ptc, Smo and/or Gli, or by reducing the binding between SHH and its cognate receptor(s). Inhibition of SHH signalling may be suitably determined and/or quantitated by measuring the expression of Patched (Ptc) gene (e.g., by RTPCR or any other transcript detection method), a primary target of SHH signalling (Erickson et al. 1996. Cell 87: 661-73).

In exemplary embodiments, an antagonist of SHH pathway may be chosen from the group comprising or consisting of: natural products such as the plant alkaloid cyclopamine (Incardona et al. 1998. Development 125: 3553-3562), cyclopamine analogues (such as, e.g., disclosed in US 2006/074030), the pyridyl SHH inhibitors disclosed in WO 2006/028958, anti-SHH antibodies such s 5E1 (Erickson et al. 1996. Cell 87: 661-73), and small molecule inhibitors such as Cur61414 (Williams et al. 2003. PNAS 100: 4616-4621).

In a particularly preferred embodiment, the SHH antagonist is cyclopamine or a functional derivative thereof.

As used herein, "sonic hedgehog agonist" refers to any natural or synthetic substance that increases or stimulates the SHH-signaling pathway.

Without limitation, SHH pathway agonists may take the form of a chemical or biological substance, a pharmaceutical agent or drug, a specific ligand of SHH receptor, a nucleic acid molecule or oligonucleotide, etc. For example, SHH pathway agonist may be a small organic molecule inhibitor, preferably having size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da. Activation of SHH signaling may be suitably determined and/or quantitated by measuring the expression of Patched (Ptc) gene (e.g., by RTPCR or any other transcript detection method), a primary target of SHH signaling (Erickson et al. 1996. Cell 87: 661-73).

In an embodiment, SHH pathway may be stimulated by increasing the expression of a protein involved therein, e.g., of SHH or of its receptor such as Ptc, Smo and/or Gli, preferably Smo, by example constitutively active forms thereof (Xie et al. 1998. Nature 391: 90-92), in mPS cells. An increase in the expression level of a protein in a cell may be achieved by methods known in the art, such as, e.g., by transfecting (e.g., by electroporation, lipofection, etc.) or transducing (e.g., using a viral vector), the cell with a recombinant nucleic acid which encodes said protein under the control of a promoter effecting suitable expression level in said cell.

In a particularly preferred embodiment, SHH pathway agonist is SHH or a functional fragment or derivative thereof, e.g., in vitro produced or synthetic SHH or fragment or derivative. Said SHH may be preferably of mammalian origin, even more preferably of same origin as the mPS cells used.

In another preferred embodiment, SHH pathway agonist is a peptidomimetic of SHH.

In another embodiment, SHH pathway agonist is a synthetic non-peptidyl small molecule such as Hh-Ag (Frank-Kamenetsky, et al. 2002. J Biol 1: 10).

As used herein, "Wnt antagonist" refers to any natural or synthetic substance that decreases, inhibits or abolishes the activity of Wnt-signalling pathway, either directly by affecting a protein in a Wnt signalling pathway or indirectly by affecting downstream mediators of Wnt signalling. Inhibition of Wnt signalling may be suitably determined and/or quantitated by measuring the expression of TCF gene (e.g., by RT-PCR or any other transcript detection method), a primary output of Wnt signalling (Nature 1997, vol. 385(6619): 829-33).

Without limitation, Wnt pathway antagonists may take the form of a chemical or biological substance, a pharmaceutical agent or drug, a specific binding agent such as a neutralising or antagonistic antibody, a nucleic acid molecule or oligonucleotide, or a dominant negative fragment or variant of Wnt or receptor thereof. For example, Wnt pathway antagonist may be a small organic molecule inhibitor, preferably having size up to about 5000 Da, e.g., up to about 4000, preferably up to 3000 Da, more preferably up to 2000 Da, even more preferably up to about 1000 Da, e.g., up to about 900, 800, 700, 600 or up to about 500 Da.

In an embodiment, Wnt pathway may be antagonised by reducing the expression of a protein involved therein in mPS cells. This may encompass any extent of reduction of expression, such as, e.g., by ≥10%, e.g., ≥20%, more preferably ≥30%, e.g., ≥40%, yet more preferably ≥50%, e.g., ≥60%, still more preferably ≥70%, e.g., ≥80%, and most preferably by ≥90%, e.g., ≥95% or even about 100%, relative to the basal expression level of the respective protein in the mPS cells; as determined using quantification methods known per se, such as, e.g., ELISA, RIA, immuno-precipitation, Western blotting, etc.

In exemplary embodiments, an antagonist of Wnt pathway may be chosen from the group comprising or consisting of:

DKK polypeptides (Glinka et al. 1998. Nature 391: 357-62; Niehrs 1999. Trends Genet. 15: 314-9), crescent polypeptides (Marvin et al. 2001. Genes & Dev 15: 316-327), cerberus polypeptides (U.S. Pat. No. 6,133,232), axin polypeptides (Zeng et al. 1997. Cell 90: 181-92; Itoh et al. 1998. Curr Biol 8: 591-4; Willert et al. 1999. Development 126: 4165-73), Frzb polypeptides (Cadigan et al. 1998. Cell 93: 767-77; U.S. Pat. No. 6,133,232; U.S. Pat. No. 6,485,972), glycogen synthase kinase (GSK) polypeptides (He et al. 1995 Nature 374: 617-22), T-cell factor (TCF) polypeptides (Molenaar at al. 1996. Cell 86: 391-9), dominant negative dishevelled polypeptides (Wallingford et al. 2000. Nature 405: 81-5), dominant negative N-cadherin polypeptides (U.S. Pat. No. 6,485,972), dominant negative beta-catenin polypeptides (U.S. Pat. No. 6,485,972), dominant negatives of downstream transcription factors (e.g., TCF, etc.), dominant negatives of Wnt polypeptides, agents that disrupt LRP-frizzled-wnt complexes, and agents that sequester Wnt (e.g., crescent and antibodies to Wnt). Wnt antagonists also encompass fragments, homologues, derivatives, allelic variants, and peptidomimetics of various polypeptides, including, but not limited to, DKK, crescent, cerberus, axin, Frzb, GSK, TCF, dominant negative dishevelled, dominant negative N-cadherin, and dominant negative beta-catenin polypeptides. Wnt antagonist polypeptides may be preferably of mammalian origin, even more preferably of same origin as the mPS cells used.

In a particularly preferred embodiment, Wnt pathway antagonist is DKK or a functional fragment or derivative thereof, e.g., in vitro produced or synthetic DKK or fragment or derivative.

In an embodiment, the mPS cells may be exposed to an antagonist of the SHH signalling pathway in combination with an inhibitor of BMP (bone morphogenetic protein) signalling pathway. In an embodiment, the mPS cells may be exposed to an SHH pathway agonist and/or an antagonist of the Wnt signalling pathway, in combination with an inhibitor of BMP signalling pathway, such as, without limitation, noggin, chordin, follistatin, Cerberus/DAN family of proteins, gremlin, sclerostin, or functional fragments or derivatives thereof, or peptidomimetics thereof. The inclusion of a BMP inhibitor further ensures the desired differentiation pathway of mPS cells.

Exposure of mPS cells in differentiation-permissive conditions to either an antagonist of the SHH signalling pathway or to an SHH agonist and/or an antagonist of the Wnt signalling pathway in aspects of the present invention may preferably commence between t=0 days and t=10 days, more preferably between t=0 days and t=7 days, even more preferably between t=0 days and t=5 days, and still more preferably between t=0 days and t=3 days, such as, e.g., at about t=0 days, t=1 day or t=2 days (wherein the time point of t=0 days is as defined above).

Said exposure may be maintained up until the differentiated neural progenitors or neuron like cells are harvested or collected (i.e., up to the end of the culturing step b), or said exposure may be limited in time, such as e.g., it may last to up to between t=25 days and t=28 days, or up to between t=21 days and t=25 days, or up to between t=16 days and t=21 days, or up to between t=10 days and t=16 days, or up to between t=10 days and t=14 days, or up to between t=7 days and t=10 days, such as, e.g., up to about t=8 days, t=9 days, t=10 days, t=11 days, t=12 days, t=13 days, or t=14 days, preferably up to about t=10 days. In particularly effective embodiments, said exposure may last between t=0 days and t=14 days, more preferably between t=0 days and t=12 days, yet more preferably between t=0 days and t=10 days, such as, e.g., between t=1 days and t=10 days, or between t=2 days and t=10 days.

As already noted, in methods of any of the above aspects A1 or A3, the overall duration of the culturing step b) may preferably be between 3 days and 21 days, more preferably between 4 days and 18 days, even more preferably between 7 days and 16 days or between 7 days and 14 days, and yet more preferably between 10 days and 14 days, e.g., about 10, 11, 12, 13 or 14 days, such as to maximise the proportion of the respective desired neural precursors in the acquired cell cultures. In methods of any of the above aspects A2 or A4, the duration of the culturing step b) may preferably be at least 16 days, more preferably at least 18 days, and even more preferably at least 21 days or at least 24 days, such as, for example, between 18 days and 40 days, more preferably between 21 days and 35 days, and even more preferably between 21 days and 30 days, e.g., about 21, 22, 23, 24, 25, 26, 27, 28, 29 or 30 days, such as to maximise the proportion of the respective mature neuron like cells in the acquired cell cultures.

As also noted, apart from the morphogens or morphogen inhibitors expressly employed in step b), other external inductive morphogen signals may be absent from the medium. In particular, the medium wherein mPS cells are cultured in step b) of above aspects A1 to A4 may lack any components that may otherwise induce caudalisation of neural progenitors. For example, in an embodiment the medium may lack any one, preferably any two or more, and most preferably all of the following: animal (e.g., mammalian) serum or plasma; retinoic acid (RA); any members of the fibroblast growth factor (FGF) family of proteins, and in particular FGF-1 through FGF-10; and any members of the Wnt family of proteins, such as WNT1 to WNT16.

The methods of the above explained aspects yield cell populations enriched for or substantially homogeneous for the desired types of neural precursors or of mature neuronal phenotypes. For example, an enriched or substantially homogeneous cell population obtained or obtainable according to the methods of the invention may comprise at least 40%, preferably at least 50%, more preferably at least 60% and even more preferably at least 70%, at least 80% or more of cells having a given desired phenotype. As can be appreciated, a given desired cell type may be further enriched or isolated from cell populations obtained or obtainable according to the above methods, thereby yielding substantially pure (e.g., ≥85% pure, preferably ≥90% pure, more preferably ≥95% pure or even ≥99% pure) preparations of said given desired cell type. Such enrichment or isolation may employ specific characteristics of the desired cell type, such as, e.g., one or more surface markers specific thereto, as known in the art (e.g., FACS, panning, immuno-magnetic cell separation, etc.).

Accordingly, in an aspect, the invention provides neural progenitors of dorsal forebrain identity or an enriched or substantially homogeneous population thereof directly obtained or obtainable according to the methods of aspect A1, as well as a substantially pure population of said neural progenitors obtained or obtainable by one or more downstream isolation processes.

In an aspect, the invention provides cortical pyramidal neuron like cells or an enriched or substantially homogeneous population thereof directly obtained or obtainable according to the methods of aspect A2, as well as a substantially pure population of said cortical pyramidal neuron like cells obtained or obtainable by one or more downstream isolation processes.

In an aspect, the invention provides neural progenitors of ventral forebrain identity or an enriched or substantially homogeneous population thereof directly obtained or obtainable according to the methods of aspect A3, as well as a substantially pure population of said neural progenitors obtained or obtainable by one or more downstream isolation processes.

In an aspect, the invention provides cortical inhibitory interneuron like cells or an enriched or substantially homogeneous population thereof directly obtained or obtainable according to the methods of aspect A4, as well as a substantially pure population of said cortical inhibitory interneuron like cells obtained or obtainable by one or more downstream isolation processes.

As noted in the Summary section, neural progenitors or neuron like cells obtainable according to the invention can be distinguished by expression of specific proteins such as surface markers. Said expression can be detected using any suitable immunological technique known in the art, such as immuno-cytochemistry or affinity adsorption, Western blot analysis, ELISA, etc., or by any suitable biochemical assay of enzyme activity, or by any suitable technique of measuring the quantity of the marker mRNA, e.g., Northern blot, semi-quantitative or quantitative RT-PCR, etc. Sequence data for markers listed in this disclosure are known and can be obtained from public databases such as GenBank.

Where a cell is said to be positive for a particular marker, this means that a skilled person will conclude the presence or evidence of a distinct signal for that marker when carrying out the appropriate measurement compared to suitable controls. Where the method allows for quantitative assessment of the marker, positive cells may on average generate a signal that is significantly different from the control, e.g., but without limitation, at least 1.5-fold higher than such signal generated by control cells, e.g., at least 2-fold, at least 4-fold, at least 10-fold, at least 20-fold, at least 30-fold, at least 40-fold, at least 50-fold higher or even higher.

As also noted in the Summary section, the invention as well foresees isolating sub-populations of neural cells or mature neuron like cells, e.g., of cortical pyramidal neuron like cells, from the cell populations obtainable according to aspects A1 to A4.

In a further aspect, the invention provides downstream derivatives from cells and populations obtained or obtainable as above, including without limitation: isolated nucleic acids (e.g., DNA, total RNA or mRNA), isolated or cloned DNA or cDNA, isolated proteins or antigens, isolated lipids, or isolated extracts (e.g., nuclear, mitochondrial, microsomal, etc.) from said cells or cell populations.

The invention also provides a composition, preferably a pharmaceutical composition, comprising neural precursor or mature neuron like cells and populations or subpopulations thereof obtained or obtainable according to the invention.

The pharmaceutical composition may contain further components ensuring the viability of the cells therein. In particular, the cells can be supplied in the form of a pharmaceutical composition, comprising an isotonic excipient prepared under sufficiently sterile conditions for human administration. For general principles in medicinal formulation, the reader is referred to Cell Therapy: Stem Cell Transplantation, Gene Therapy, and Cellular Immunotherapy, by G. Morstyn & W. Sheridan eds, Cambridge University Press, 1996. Choice of the cellular excipient and any accompanying elements of the composition will be adapted in accordance with the device used for administration. For example, the composition may comprise a suitable buffer system to suitable pH, e.g.; near neutral pH (e.g., phosphate or carbonate buffer system), and may comprise sufficient salt to ensure iso-osmotic conditions for the cells, i.e., preventing osmotic stress. For example, suitable solution for these purposes may be phosphate-buffered saline (PBS) as known in the art. Further, the composition may comprise a carrier protein, e.g., albumin, which may increase the viability of the cells. Preferably, to ensure exclusion of non-human animal material, the albumin may be of human origin (e.g., isolated from human material or produced recombinantly). Suitable concentrations of albumin are generally known.

Hence, pharmaceutical compositions according to the present invention, and for use in accordance with the present invention, may comprise, in addition to the neural progenitors or neuron like cells, a pharmaceutically acceptable excipient, carrier, buffer, preservative, stabiliser, anti-oxidant or other material well known to those skilled in the art. Such materials should be non-toxic and should not interfere with the activity of the cells. The precise nature of the carrier or other material will depend on the route of administration. The composition may include one or more of a neuro-protective molecules, a neuro-regenerative molecule, a retinoid, growth factor, astrocyte/glial cells, anti-apoptotic factor, or factor that regulates gene expression in the cells of the invention. Such substances may render the cells independent of its environment. The invention also encompasses methods of producing said pharmaceutical compositions by admixing the cells of the invention with one or more additional components as above.

Liquid pharmaceutical compositions generally include a liquid carrier such as water, petroleum, animal or vegetable oils, mineral oil or synthetic oil. Physiological saline solution, tissue or cell culture media, dextrose or other saccharide solution or glycols such as ethylene glycol, propylene glycol or polyethylene glycol may be included.

The composition may be in the form of a parenterally acceptable aqueous solution, which is pyrogen-free and has suitable pH, isotonicity and stability. Those of relevant skill in the art are well able to prepare suitable solutions using, for example, isotonic vehicles such as Sodium Chloride, Ringer's Injection, or Lactated Ringer's Injection. A composition may be prepared using artificial cerebrospinal fluid.

In a further aspect, the invention relates to an arrangement comprising a surgical instrument for administration of a composition at a site of tissue dysfunction or lesion and further comprising the pharmaceutical composition as defined above, wherein the arrangement is adapted for administration of the pharmaceutical composition at the site of tissue dysfunction or lesion. For example, a suitable surgical instrument may be capable of injecting a liquid composition comprising cells of the present invention at the site of neural dysfunction or lesion. Cells may be implanted into a patient by any technique known in the art (e.g. Freed et al. 1997. Cell Transplant 6: 201-202; Kordower et al. 1995. N Engl J Med 332: 1118-1124; Freed et al. 1992. N Engl J Med 327: 1549-1555).

Where administration of neural precursors or mature neuron like cells to a patient is contemplated, it may be preferable that the mPS cells, e.g., human ES or EG cells, subjected to the methods of the present invention, are selected such as to maximise the tissue compatibility between the patient and the administered cells, thereby reducing the chance of rejection of the administered cells by patient's immune system (graft vs. host rejection). For example, advantageously the mPS cells or cell lines may be typically selected which have either identical HLA haplotypes (including one or preferably more HLA-A, HLA-B, HLA-C, HLA-D, HLA-DR, HLA-DP and HLA-DQ; preferably one or preferably all HLA-A, HLA-B and HLA-C) to the patient, or which have the most HLA antigen alleles common to the patient and none or the least of HLA antigens to which the patient contains pre-existing anti-HLA antibodies.

Furthermore, the invention contemplates the neural precursor or mature neuron like cells and populations obtained or obtainable according to the invention for use in therapy, or their use for the manufacture of a medicament for the treatment of neurological or neuropsychiatric disease. The invention also contemplates the neural precursor or mature neuron like cells and populations obtained or obtainable according to the invention for use in the treatment of neurological or neuropsychiatric disease. Accordingly, the invention also provides a method for treating a neurological or neuropsychiatric disease in a patient in need of such treatment, comprising administering a therapeutically effective amount (i.e., an amount sufficient to elicit a desired local or systemic effect) of the neural precursor or mature neuron like cells and populations obtained or obtainable according to the invention to said patient. For instance, said isolated cells may be transplanted or injected to a patient. Neurological or neuropsychiatric diseases to be treated using the cells and cell populations of the invention may involve neuronal dysfunction and/or degeneration, damage or loss, in particular but not limited to cortical areas, and in particular affecting one or more types of cortical pyramidal neurons or cortical inhibitory interneurons. Such ailments may include, without limitation, Alzheimer's disease, Huntington's chorea, Parkinson's disease, dementia, HIV dementia, stroke, epilepsy, multiple sclerosis, traumatic brain injury, cerebral ischemia, cerebral haemorrhage, and the like.

In an embodiment, the neural precursors or mature neuron like cells and populations obtained or obtainable according to the invention may represent in vitro models for neuronal, neurological or neuropsychiatric diseases, particularly human diseases, e.g., ones listed in the previous paragraph. Said neural precursors or mature neuron like cells or populations may be derived from subjects having a neuronal disease of interest, or the cells or populations may be derived from healthy subjects and further manipulated to display a pathological phenotype of interest. For example, such manipulation may include contacting said cells or populations externally with an agent, e.g., a chemical or biological agent, known or suspected of causing a pathological phenotype of interest. Exemplary agents may include, without limitation, neurotoxins, agents modulating neurotransmission, metabolites, drugs, antisera, viral agents etc. In another example, such manipulation may include transiently or stably transforming the cells (e.g., by transfection or transduction as known in the art) with a recombinant construct encoding an RNA or protein agent known or suspected of causing a pathological phenotype of interest, or an agent (e.g., an RNAi agent or a dominant negative variant) that can suppress the expression of an endogenous gene known or suspected to contribute to a disease of interest. Exemplary agents to be expressed may include, without limitation, disease-causative proteins such as mutant huntingin, mutant presenilins or APP, etc.

In another aspect, the invention provides use of the neural precursor or mature neuron like cells and populations obtained or obtainable according to the invention, optionally and preferably wherein said cells or populations represent models for neuronal, neurological or neuropsychiatric diseases, particularly human diseases, in any variety of screening assays, particularly in vitro screening assays, such as, e.g., in assays of biological effects of candidate pharmacological substances and compositions; assays of cellular toxicity, genotoxicity or carcinogenicity of chemical or biological agents; assays allowing the study of normal neuronal function and of the aetiology of neurological or neuropsychiatric diseases, and the like.

Cell-based in vitro screening assays can be carried out as generally known in the art. For example, cells grown in a suitable assay format (e.g., in multi-well plates or on coverslips, etc.) are contacted with a candidate agent (e.g., a potential pharmacological agent) and the effect of said agent on one or more relevant readout parameters is determined and compared to a control. Relevant readout parameters may greatly vary depending on the type of assay and may include, without limitation, neuronal survival, occurrence of apoptosis or necrosis, altered morphology (e.g., number, length and/or arborisation of neural projections), elecrophysiological behavriour, gene expression, etc. Hence, in an embodiment the invention provides a screening assay to identify pharmacological agents for the treatment of a neuronal, neurological or neuropsychiatric disease phenotype, comprising contacting the neural precursor or mature neuron like cells and populations obtained or obtainable according to the invention which display said disease phenotype with a candidate pharmacological agent, and determining alleviation of said disease phenotype when said agent is administered. The invention also relates to so-identified pharmacological agents.

Accordingly, the invention also provides the use of neural progenitors or neuron like cells or populations comprising such, as described herein, for screening assays preferably in vitro screening assays, particularly pharmaceutical, genetic or toxicological screening assays. In an embodiment, said neural progenitors or neuron like cells or populations may represent (e.g., have been so manipulated, see above) a model for a neuronal, neurological or neuropsychiatric disease, preferably a human disease.

In the present invention, the mPS cells or cell lines or the neural progenitors or mature neuron like cells obtained there from, may be stably or transiently transfected or transformed with a nucleic acid of interest prior to further use, e.g., in therapy, screening or research. Nucleic acid sequences of interest may include, but are not limited to, e.g., those encoding gene products which enhance the survival, growth, differentiation and/or functioning of the neural progenitors or neuron like cells, such as without limitation neurotropic factors (e.g., NGF, BDNF or GDNF); anti-apoptotic molecules (e.g., Bcl2); axon regenerating, elongating or guiding molecules (e.g., ephrins), and the like.

EXAMPLES

Example 1

Neurogenesis from ES Cells Following a Default Pathway Generates Forebrain-Like Progenitors Experimental Procedures Unless otherwise specified, all chemicals were obtained from Sigma-Aldrich (Bornem, Belgium).

ES Cell Culture

Embryonic stem cells (E14Tg2a, obtained from Baygenomics, and E14Tg2a-GFP, a derivative thereof) were routinely propagated in GMEM (Invitrogen-Gibco) supplemented with 10% ES-certified fetal bovine serum (Invitrogen-Gibco), 1×MEM-nonessential amino acids (Invitrogen-Gibco), 2 mM glutamine (Invitrogen-Gibco), 1 mM sodium pyruvate (Invitrogen-Gibco), 55 µM beta-mercaptoethanol (Sigma) and $10^3$ U/ml leukemia inhibitory factor (LIF) (ESGRO) on gelatin-coated cell culture plastic dishes (0.1% gelatin; Sigma) or on mitotically-inactivated mouse embryonic fibroblasts (MEFs: Tau-GFP KI cell line).

Neural Differentiation

Similar results were obtained with several ES cell lines, including distinct derivatives of E14 and J1 cells. ES cells were trypsinised, dissociated and plated at a density of 5×10³ cells/cm² on gelatin-coated cell culture plastic dishes in ES medium. When needed, the cells were plated for 15-30 minutes on gelatin coated-dishes, to let the MEFS adhere and the supernatant containing ES cells only was recovered and subsequently replated on gelatin coated dishes. After adhesion, medium was changed to "Default Differentiation Medium" (DDM). DDM consists of DMEM/F12 (Invitrogen-Gibco) supplemented with 1×N2 supplement (100×N2 supplement consists of 8.61 µM insulin, 1 mM transferrin, 2 µM progesterone, 10.01 mM putrescine and 3.01 µM selenite; Invitrogen-Gibco), 2 mM glutamine (Invitrogen-Gibco), 1×MEM-nonessential amino acids (Invitrogen-Gibco), 1 mM sodium pyruvate (Invitrogen-Gibco), 110 µM beta-mercaptoethanol (Sigma) and 0.5 mg/ml Bovine Serum Albumine, Fraction V (Invitrogen-Gibco). Medium was changed every two days.

After 10 or 14 days of differentiation, at a time where most cells have been converted to neural identity, cells were trypsinised, dissociated and plated on polylysine (30 µg/ml in PBS for 2 h at 37° C.; Beckton-Dickinson) and laminin (3 µg/ml in PBS for 2 h at 37° C.; Becton-Dickinson) coated sterilised glass coverslips (Menkl) and allowed to grow for 4 or 7 to 14 days, respectively, in N2B27 medium, to allow improved survival of the neurons than in DDM alone. N2B27 medium consists of a 1:1 mixture of DMEM/F12 supplemented with 1×N2, 2 mM glutamine, 0.5 mg/ml BSA, fraction V and 110 µM beta-mercatoethanol and Neurobasal (Invitrogen-Gibco) supplemented with B27 (without vitamin A; Invitrogen-Gibco) and 2 mM glutamine. The B27 supplement (Invitrogen-Gibco) contains D-biotin, BSA (fatty acid-free, fraction V), catalase, L-carnitine HCl, corticosterone, ethanolamine HCl, D-galactose (anhydrous), glutathione (reduced), insulin (human, recombinant), linoleic acid, linolenic acid, progesterone, putrescine 2.HCl, sodium selenite, superoxide dismutase, T3-albumin complex, DL-tocopherol, DL-tocopherol acetate and transferrin (human, iron-poor) (Yao et al. 2006. PNAS 103: 6907-6912). Medium was changed every two days.

Microscopy

Pictures were taken using a Zeiss Axioplan microscope or a Zeiss LSM510 confocal microscope.

Immuno-Fluorescence and Quantification

Medium was removed and cells were rinsed with PBS then fixed for 30 min in 4% paraformaldehyde (PFA) in PBS, pH 7.4 at 4° C. PFA was removed and cells were rinsed three times with PBS. Blocking of unspecific antibody activity and permeabilization was done in PBS supplemented with 5% horse serum (Invitrogen-Gibco), 3% bovine serum albumin (Sigma) and 0.3% Triton X-100 (Sigma). Incubation with primary antibodies was done in PBS supplemented with 1% horse serum, 3% bovine serum albumin and 0.1% Triton X-100 overnight at 4° C. Cells were rinsed three times with PBS and incubated with secondary antibodies in PBS supplemented with 1% horse serum, 3% bovine serum albumin and 0.1% Triton X-100 for one hour at room temperature then rinsed again three times with PBS. For double or multiple immunostaining, the process was repeated. Nuclei were stained with bisbenzimide (Hoechst#33258; Sigma) and coverslips were mounted with glycergel (DAKO). For some antibodies, antigen retrieval was used before blocking: cells were boiled during 4×5 minutes in 10 mM citrate buffer (pH 6.0) and cooled down to room temperature during 20 minutes.

Primary antibodies used in the Examples were mouse monoclonal anti-beta-tubulin III (Tuj1, 1/1000; Covance), anti-microtubule associated protein 2 (MAP2, clone AP20, 1/500; Sigma), anti-reelin (clone G10, 1/300; from A. Goffinet), anti-Mash1 (1/500; Pharmingen), anti-p73 (ER-15, 1/150; Labvision/Neomarkers), anti-HNF4 (1/50, Abcam), anti-pan-cytokeratin (1/50, Sigma) and anti-rhodopsin (RET-P1, 1/100; Abcam), rabbit polyclonal anti-Pax6 (1/2500; Covance), anti-Otx1+2 (1/2000; Chemicon), anti-Nkx2.1 (1/5000; from R. Di Lauro), anti-Gsh2 (1/2000; from Y. Sasai), anti-Oct4 (1/500, Abcam), anti-caspase 3 (1/500, Promega), anti-Ki67 (1/200, Novocastra), anti-Tbr1 (1/20000; from R. Hevner and Chemicon), anti-Tbr2 (1/2500; from R. Hevner and Chemicon), anti-Nestin (long tail, 1/5000; Covance), anti-beta-tubulin III (1/2000; Covance), anti-GFAP (1/500; Sigma), anti-calretinin (1/10000; Swant), anti-VGluT1 (1/2000; Synaptic Systems), anti-VGluT2 (1/2500; Synaptic Systems), anti-VGAT (1/3000; Synaptic Systems), anti-tyrosine hydroxylase (1/500; Chemicon), anti-choline acetyltransferase (1/500; Chemicon), anti-GABA-A alpha-6 receptor (1/1000; Chemicon), anti-FoxP2 (1/1000; Abcam), anti-Satb2 (1/2000; from V. Tarabykin), anti-ER81 (1/1000; from S. Arber), anti-Cux1 (1/1000, Santa Cruz), anti-Tle4 (1/3000, from S. Stifani), anti-COUP-TFI and anti-COUP-TFII (1/1000, from M. Studer), and rat monoclonal anti-CTIP2 (1/1000; Abcam), and anti-PECAM (1/1000, Beckton-Dickinson), and chick anti-beta-tubulin III (1/300, Chemicon). The RAT-401 antibody (anti-Nestin; 1/5) developed by S. Hockfleld, the 74-5A5 antibody (anti-Nkx2.2; 1/20) developed by T. M. Jessell, the anti-Math1 (1/10) developed by J. Johnson, the Otx-5F5 (anti-Otx1; 1/10) developed by S. K. McConnell, the 4G11 antibody (anti-Engrailed-1; 1/50) developed by T. M. Jessell and S. Morton, and the MF-20 (anti-myosin; 1/20) developed by D. A. Fischman were obtained from the Developmental Studies Hybridoma Bank developed under the auspices of the NICHD and maintained by The University of Iowa, Department of Biological Sciences, Iowa City, Iowa 52242. Secondary antibodies were donkey anti-mouse, anti-rabbit, anti-rat, anti-goat or anti-chick coupled to Cyanin 3 or Cyanin 5 (1/1000, Jackson Immunoresearch) or to AlexaFluor 488 (1/1000, Molecular Probes).

For quantification of the proportion of cells expressing a specific marker (differentiation markers, region-specific markers, neurotransmitter transporter proteins or layer-specific markers), at least 300 cells from 3 independent experiments (at least 100 cells from each experiment) were counted for each time-point studied.

RT-PCR

For total RNA preparation, cells were trypsinised, dissociated, centrifuged and rinsed once in PBS before being flash-frozen in liquid nitrogen. RNA preparation was made using RNeasy RNA preparation minikit (Qiagen). Reverse transcription was done using Superscript II kit and protocol (Invitrogen). PCR primers used are summarized in Table 1.

TABLE 1

| Gene | Annealing temp. (° C.) | Amplicon size (bp) | Forward primer | Reverse primer |
| --- | --- | --- | --- | --- |
| emx1 | 58 | 622 | ccctcactctttcttcagcg (SEQ ID No. 1) | cagcccattctcttgtccctc (SEQ ID No. 15) |

TABLE 1-continued

| Gene | Annealing temp. (° C.) | Amplicon size (bp) | Forward primer | Reverse primer |
|---|---|---|---|---|
| emx2 | 59 | 522 | caccttctacccctggctca (SEQ ID No. 2) | ttctcggtggatgtgtgtgc (SEQ ID No. 16) |
| pax6 | 63 | 431 | aacctggctagcgaaaagcaa (SEQ ID No. 3) | ccatttggcccttcgattaga (SEQ ID No. 17) |
| ngn2 | 60 | 672 | acgcacgagaacgacaacacac (SEQ ID No. 4) | gatcttcgtgagcttggcatc c (SEQ ID No. 18) |
| mash1 | 59 | 563 | gaagcaggatggcagcagat (SEQ ID No. 5) | acagaagcaaagaccgtg gg (SEQ ID No. 19) |
| dlx1 | 59 | 722 | ccaaaagggaagcagaggag (SEQ ID No. 6) | cccagatgaggagttcggat (SEQ ID No. 20) |
| dlx5 | 57 | 567 | caccacccgtctcaggaatc (SEQ ID No. 7) | gttacacgccatagggtcgc (SEQ ID No. 21) |
| nkx2.1 | 66 | 352 | aacctgggcaacatgagcgagctg (SEQ ID No. 8) | atcttgacctgcgtgggtgtc agg (SEQ ID No. 22) |
| lhx6 | 55 | 727 | tagagcctccccatgtacgcc (SEQ ID No. 9) | tgctgcggtctatgctttt (SEQ ID No. 23) |
| lhx7 | 58 | 600 | gaacaagacacactggtggca (SEQ ID No. 10) | cccataccgtctgaagtaat cg (SEQ ID No. 24) |
| shh | 60 | 447 | gccagcggcagatatgaaggg (SEQ ID No. 11) | gtgcacggtggcggatcc (SEQ ID No. 25) |
| ptc1 | 62 | 603 | gctgtgcctgtggtcatcct (SEQ ID No. 12) | caagggaggctgatgtctgg (SEQ ID No. 26) |
| ptc2 | 60 | 572 | ctctggcactgggtctccga (SEQ ID No. 13) | ggggtcatcagggtccaga ca (SEQ ID No. 27) |
| foxG1 | 60 | 514 | tgaagaggaggtggagtgcc (SEQ ID No. 14) | gctgaacgaggacttggga a (SEQ ID No. 28) |

1 µl of RT was engaged in each PCR reaction, using Taq polymerase kit and protocol (Invitrogen-Gibco). RT-PCR were performed at least three times for each gene at each time-point studied.

Results

We cultured ES cells at low density and optimised their survival in minimal conditions using a chemically defined serum-free medium (DDM) that is devoid of serum or any known morphogen, but that allows the survival of ES cells and neural precursors inter alia and in particular by insulin.

ES cells underwent an efficient neurogenesis process: Nestin-positive neural progenitors constituted more than 70% of the total cell population after 7-14 days in DDM (FIG. 1A). Subsequently most neural progenitors differentiated into β-tubulin-III positive and MAP2 positive neurons that constituted more than 70% of the total cell population after 21-28 days of differentiation (FIG. 1A). Astroglial production appeared only after 21 days of differentiation (FIG. 1A), thus following a neuron-glia sequence highly reminiscent of the one described for cortical stem cells in culture (Qian et al. 2000. Neuron 28: 69-80). These data indicate that ES cells cultured in absence of any added morphogen spontaneously and efficiently differentiate into neural cells.

We next looked at the identity of the neural progenitors generated in these default conditions, using a battery of markers of regional identity of the neural tube. We found that after 14 days of differentiation, most (71.38+/−1.32%) Nestin-positive neural precursors expressed Otx1-2 TFs, early markers of the anterior neurectoderm (FIG. 1B(1), white column). A subset of these progenitors were found to express OW and Pax6 (12.50+/−1.85% and 27.93+/−2.47%, respectively; FIGS. 1B(3) and (2), white columns), which delineate parts of the dorsal forebrain primordium at early stages (Inoue et al. 2000. Dev Biol 219: 373-383; Walther & Gruss 1991. Development 113: 1435-1449), while a greater proportion among them expressed Gsh2, Nkx2.1 or Nkx2.2 (11.31+/−2.03%, 25.86+/−3.07% and 34.27+/−2.65%, respectively) (FIGS. 1B(4), (5) and (6), white columns), three markers that characterise the ventral part of the rostral-most forebrain at early stages (Puelles & Rubenstein 2003. Trends Neurosci 26: 469-476). In contrast only a minority (less than 1%) of neural progenitors expressed markers indicative of more caudal identity, such as Engrailed-1 (midbrain), Math1 (cerebellum) and HoxB1 (hindbrain) (FIGS. 1B(7), (8) and (9), white columns).

The forebrain-like identity of the majority of ES cell-derived neural progenitors was further confirmed by RT-PCR experiments, showing expression of foxg1, emx1-2, dlx1-5 and lhx6 TFs, all markers that are restricted to the developing forebrain in vivo (FIG. 1C).

Altogether, these results indicate that differentiation of ES cells in DDM leads to the efficient generation of a population of neural progenitors of prospective forebrain identity. Interestingly, this population seems to comprise cells corresponding mainly to an anterior and ventral forebrain phenotype, together with cells of a more dorsal identity.

Example 2

Antagonizing the SHH Pathway During Default Neurogenesis Converts Most Neural Progenitors to a Cortical Identity Experimental Procedures Experimental procedures were as described in Example 1. When foreseen during neural differentiation, cyclopamine (Calbiochem; dissolved in 100% ethanol) was added from day 2 to day 10 in the differentiation medium (DDM) at a final concentration of 1 μM. Ethanol was used as control.

Results

We hypothesised that the presence of a large proportion of neural progenitors expressing markers of the ventral forebrain in DDM cultures might be due to SHH activity. Consistent with this hypothesis we found that Shh is induced after two days of DDM culture (FIG. 1C(h)).

To test whether SHH signalling was indeed active in the system we attempted to block it during differentiation by using cyclopamine, a specific antagonist of the SHH pathway that binds to Smoothened receptor (Chen et al. 2002. Genes Dev 16: 2743-2748), during the neural induction and neural progenitor differentiation process, from day 2 to day 10 (referred to herein as DDM+cyclo conditions).

Importantly, cyclopamine did not change significantly the neuralization process per se, as demonstrated by the pattern expression of pan-neural markers at different time points, which was similar to what was observed without cyclopamine (FIG. 1E, compare to FIG. 1A without cyclopamine). Cyclopamine did not alter the anterior identity of the neural progenitors either, as demonstrated by the high percentage of Otx1-2 positive neural progenitors (75.57+/−1.21%; FIG. 1B(1), black column). However cyclopamine had a dramatic effect on the dorso-ventral patterning of neural progenitors, causing a massive shift from ventral to dorsal forebrain identity and converting the vast majority of neural progenitors to adopt a dorsal forebrain-like identity: upon addition of cyclopamine, the expression of Gsh2, Nkx2.1 and Nkx2.2 among neural progenitors was almost abolished (1.37+/−0.61%, 1.87+/−1.10%, and 4.05+/−1.10% of the Nestin-positive cells, respectively; $p<0.001$ for all three markers) (FIGS. 1B(4), (5) and (6), black columns), while the expression of Pax6 and Otx1 were greatly increased (73.03+/−2.44% and 71.21+/−2.52% of the Nestin-positive cells, respectively; $p<0.001$ for both markers) (FIG. 1B(2), (3), black columns).

RT-PCR experiments confirmed these observations, showing that blocking SHH signalling results in a potent induction of dorsal markers, in particular emx1 (FIG. 1D(c)), the most specific marker of the cortical primordium, and repression of all ventral markers examined (FIG. 1D).

Altogether, these results indicate that, following inhibition of SHH signalling in DDM cultures, ES cells can be converted to a largely homogeneous population of neural progenitors expressing markers corresponding to the presumptive cerebral cortex (Inoue et al., 2000, supra). Importantly we did not detect any obvious difference in proportion of neural progenitors, neurons, or glia generated in the DDM+cyclo conditions, all of which appeared following the same time line (FIG. 1A, E), while the pattern of proliferation of neural progenitors appeared unchanged, as assessed by short BrdU pulse labelling at days 10 and 14 (Day 10 DDM: 47.98+/−3.35%; Day 10 cyclo: 42.11+/−3.42%; Day 14 DDM: 31.61+/−2.07%; Day 14 cyclo: 28.57+/−2.00%; $p>0.05$ in both cases). It thus appears that the addition of cyclopamine did not have any major effect on proliferative or survival rates of the neural lineage, suggesting that the inhibition of SHH has a direct instructive effect on cell fate choice rather than a selective effect on particular populations of neural progenitors.

Example 3

Neurons Generated from ES Cells in DDM+Cyclo Display Molecular, Cellular, and Functional Properties Characterising Cortical Pyramidal Neurons Experimental Procedures Experimental procedures were as described in Examples 1 and 2.

Electrophysiology

Electrophysiological recordings were performed at room temperature (20-25° C.) in an external solution (ACSF) containing 120 mM NaCl, 26 mM NaHCO$_3$, 11 mM D-glucose, 2 mM KCl, 2 mM CaCl$_2$, 1.2 mM MgSO$_4$ and 1.2 mM KH$_2$PO$_4$ with an osmolarity of 290 mOsm. The recording chamber was constantly superfused at a flow rate of 1 ml/min. The recording patch pipettes were made of borosilicate GC100TF-10 capillary tubing (Clark Electrical Instruments, Reading, UK) pulled on a P-2000 micropipette puller (Sutter Instrument Co, Novato, Calif., USA) and presented resistances of 4-6 MΩ when filled with the patch pipette solution containing either 150 mM KCl, 10 mM 4-(2-hydroxyethyl)-1-piperazineethanesulfonic acid (HEPES), 4.6 mM MgCl$_2$, 4 mM Na$_2$ATP (adenosine triphosphate) and 0.4 mM Na$_3$GTP (guanosine triphosphate) or 110 mM CsF, 0.1 mM ethylene glycol bis(beta-aminoethyl ether)-N,N,N',N'-tetraacetic acid (EGTA), 0.035 mM CaCl$_2$, 1 mM MgCl$_2$, 10 mM D-glucose and 10 mM HEPES, this latter solution being used for the recording of spontaneous inhibitory postsynaptic currents (sIPSC). Both pipette solutions were adjusted to pH 7.3 and 300-330 mOsm/l. Whole-cell patch clamp recordings were carried out with an EPC10 amplifier (HEKA, Elektronik, Lambrecht/Pfalz, Germany) in voltage clamp mode. Signals were filtered at 4 kHz using the built-in filter of EPC10 and digitally sampled at 20 kHz except spontaneous postsynaptic currents signals that were filtered at 2.5 kHz and digitally sampled at 5 kHz. Voltage protocol generation, data acquisition and analysis were made with Pulse 8.65 (HEKA, Elektronik, Lambrecht/Pfalz, Germany). The presence of spontaneous excitatory postsynaptic currents (sEPSCs) was assessed by clamping neurons to −60 mV in the presence of 100 μM picrotoxin. The presence of spontaneous inhibitory postsynaptic currents (sIPSCs) was assessed by clamping neurons to ±20 mV in the presence of 1 μM TTX, 5 μM 2,3-dioxo-6-nitro-1,2,3,4-tetrahydrobenzo[f]quinoxaline-7-sulfonamide disodium salt (NBQX) and 50 μM D-(−)-2-amino-5-phosphonopentanoic acid (APV). To further check the nature of spontaneous postsynaptic currents, NBQX (5

μM) and APV (50 μM) were used to block AMPA and NMDA receptors respectively and picrotoxin (100 μM) was used to block GABA$_A$ receptors. Fifteen neurons were recorded for each type of PSC and for each condition (DDM or DDM+cyclo).

Morphology

For morphology study, we used the Pyramidal Morphology Index (PMI) described by Hand et al. 2005 (Neuron 48: 45-62). Pictures of at least 100 neurons stained for MAP2 were to taken randomly for each condition and from two different experiments and the quantification was done blindly in Adobe Photoshop Software using a 25 μm circle drawn on a superposed layer.

Results

We characterised the fate of the neurons being generated from the neural progenitors in DDM+cyclo conditions, in terms of molecular, cellular, and functional properties, and compared them with those of neurons generated in DDM conditions.

We found that most neurons derived from neural progenitors generated in DDM+cyclo expressed the vesicular glutamate transporters VGluT1, a marker of excitatory glutamatergic neurons of the cerebral cortex (70.04+/−2.98% of Tuj1-positive cells after 28 days of differentiation) or VGluT2 (15.46+/−2.52%), while only a minority of them (11.30+1-3.31% of Tuj1-positive neurons) expressed the vesicular GABA transporter VGAT, a marker of GABAergic inhibitory neurons (FIG. 2A).

This phenotype differed markedly from the one observed for neurons derived from progenitors obtained in DDM alone (FIG. 2A): in this case we observed a much greater proportion of GABAergic neurons (39.38+/−2.73%; p<0.001; z-test for proportions), and a much lower proportion of glutamatergic neurons (36.29+/−2.60% of VGluT1-expressing neurons and 12.29+/−1.75% of VGluT2-expressing neurons); p<0.001 and >0.05 respectively). In this experiment, we found no evidence for the presence of monoaminergic or cholinergic neurons in either DDM or DDM+cyclo conditions, and no markers of other specific neuronal fates such as rhodopsin or GABA-alpha6-receptor (photoreceptors and cerebellar granule cells, respectively) (not shown).

To determine whether the differential expression of neurotransmission molecular markers was correlated with specific functional properties, we performed patch-clamp recordings.

We first determined the maturation time window corresponding to the optimal electrical activity at around day 28. At that time, neurons showed normal and robust excitability, including spontaneous action potentials and synaptic currents, in both DDM and DDM+cyclo conditions (FIG. 2B—iPSCs, FIG. 2C—ePSCs). However, in DDM conditions we recorded a mixture of inhibitory and excitatory synaptic activity, as 38.46+/−13.49% and 6.67+/−6.44% of the neurons displayed spontaneous GABAergic inhibitory (iPSCs) and glutamatergic excitatory post-synaptic currents (ePSCs) respectively, while following DDM+cyclo conditions, most activity corresponded to glutamatergic excitatory synaptic activity, as 38.89+/−11.49% of the neurons displayed ePSCs, and no or little iPSCs could be recorded (FIG. 2D; p<0.05 for both ePSCs and iPSCs; Fisher exact t-test).

Thus, the differences observed for expression of neurotransmission markers between neurons derived from DDM vs. DDM+cyclo conditions correlated with similar functional differences in synaptic activity.

Cortical neurons can be also distinguished by their morphological properties: cortical excitatory neurons exhibit a pyramidal or unipolar morphology, characterised by the presence of one dendrite wider than the others, while GABA-ergic interneurons show multipolar morphologies.

Therefore we compared the morphology of the neurons generated in each condition, and observed an important qualitative shift in the morphology in each condition, with many more neurons in DDM+cyclo displaying a unipolar morphology with a prominent dendrite of pyramidal shape (FIG. 3 A, B). Semi-quantitative scoring of the morphology of ES cells-derived neurons revealed that the majority (61.39+/−4.84%) of neurons derived from ES cells in DDM+cyclo showed a unipolar morphology, while only a fraction of them (16.98+/−3.65%) showed such a morphology in DDM conditions (FIG. 3C, p<0.01, Chi-square test).

To analyse these data quantitatively we used a recently described pyramidal index (PMI), which corresponds to the ratio between the width of the largest dendrite and the number of neurites extending from the same neuron (Hand of al. 2005, supra). Using quantification of the PMI on neurons dissociated from early post-natal cortex and cultured for two days, we found that glutamatergic neurons displayed a much higher PMI score than GABAergic interneurons, and a cut-off value could be determined (1.2 μm) that enabled to objectively distinguish cortical excitatory and inhibitory neurons based on their dendritic morphology (FIG. 3D).

Most neurons derived from ES cells in DDM+cyclo displayed a significantly higher PMI than following DDM conditions (FIG. 3 E, F; p<0.001; Mann-Whitney test). The majority of neurons (77.23+/−4.17% of MAP2-positive neurons after 28 days of differentiation) derived in DDM+cyclo displayed a PMI superior to the cut-off value, thus corresponding to putative pyramidal neurons (FIG. 3F), while in DDM conditions, this proportion was only of 29.25+/−4.42% (p<0.001; z-test for proportions).

Altogether these data indicate that the bulk of neurons generated from ES cells in DDM+cyclo conditions display morphological and functional properties characterising pyramidal neurons, while neural progenitors produced in DDM produces a mixture of GABA-ergic interneurons and pyramidal neurons.

Example 4

Neurons Derived from ES Cells in DDM+Cyclo Behave Like Pyramidal Neurons in Cortical Grafts Experimental Procedures Experimental procedures were as described in Examples 1 to 3.

Overlay Assay

Postnatal day 2 (P2) mice brains were dissected in cold L15 buffer supplemented with glucose, embedded in 3% low-melting point agarose in L15, and sectioned (coronal) on a vibratome at 300 μm. Slices were cultured on a transparent porous membrane (1 μm pore size, Greiner) in a 35-mm well containing N2B27 medium. Neurons derived from GFP-expressing ES cells were dissociated after 21 days into a single-cell suspension by trypsinisation and mechanical trituration, washed and resuspended at $1 \times 10^6$ cells per milliliter before being plated onto cortical slices (50 μl of cell suspension per slice). Slices were cultured for 4 days after plating, then fixed with 4% PFA overnight at 4° C. and processed for immunofluorescence. PFA was removed and slices were rinsed three times with PBS. Blocking of unspecific antibody activity and permeabilisation was done in PBS supplemented with 3% BSA (Sigma) and 0.3% Triton X-100 (Sigma). Incubation with primary antibodies was done in PBS supplemented with 3% BSA and 0.3% Triton X-100 overnight at 4° C. Cells were rinsed three times with PBS and incubated with secondary antibodies in PBS supplemented with 5% horse serum (Invitrogen-Gibco), 3% BSA (Sigma) and 0.3% Triton X-100 (Sigma) overnight at 4° C. then rinsed again three times with PBS. For double immunostaining, the process was repeated. Nuclei were stained with bisbenzimide (Hoechst#33258; Sigma) and coverslips were mounted with glycergel (DAKO). Quantification of radial dendrite orientation was done blindly, according to Polleux et al. 2000 (Nature 404: 567-573) using Adobe Photoshop software. At least 300 cells on at least 9 different slices coming from 3 independent experiments were assessed (at least 100 cells from each experiment).

Results

Within the cortex, glutamatergic pyramidal neurons are polarized and oriented radially, with one large dendrite, the apical dendrite, pointing towards the cortical surface, and the axon pointing towards the ventricular surface. Most cortical inhibitory interneurons are by definition non-pyramidal in morphology and therefore their axon and dendrites growth is not constrained along the radial axis.

Using a slice overlay assay (Polleux & Ghosh 2002. Sci. STKE. 2002, L9), it has been previously shown that freshly dissociated neurons from embryonic cortex readily readopt this radial orientation upon grafting on top of cortical slices, in part by responding to semaphorin and Slit signaling (Whitford et al. 2002. Neuron 33, 47-61; Polleux et al., 2000. Nature 404, 567-573). Importantly, thalamic neurons or neurons derived from ventral telencephalon (including cortical interneurons) do not show such a radial orientation pattern of growth.

We adapted the slice overlay assay to test if neurons derived from eGFP-labelled ES cells following DDM+cyclo and DDM conditions can respond to extracellular cues polarizing dendritic outgrowth and thus orient radially like pyramidal neurons. Neurons were first generated in vitro from ES cells expressing constitutively eGFP, and after 21 days of differentiation, they were dissociated on top of mouse postnatal cortical slices. Four days after plating, eGFP+ neurons with a pyramidal morphology have integrated the cortex (FIG. 4). Strikingly, the majority (64.98+/−2.40%) of these neurons displayed a radial orientation with an apical dendrite pointing to the cortical pial surface (FIG. 4C,D,H,I). In some cases the axon emerging from the radially-oriented neurons was visible and usually pointed towards the ventricle (FIG. 4E-G). In contrast, when similar experiments were conducted with neurons generated from ES cells in DDM, only a minority (FIG. 4I; 26.05+/−2.32%; p<0.001) of these neurons adopted a radial orientation. In this case, neurons displayed either a tangential orientation, a multipolar morphology or did not extend visible dendrites (FIG. 4A,B,I).

These results show that neurons derived from ES cells in DDM+cyclo conditions, and subsequently confronted to cortical slices, exhibit a radial orientation behaviour that is highly specific of the terminal differentiation program followed by pyramidal neurons in vivo. This demonstrates that an important and specific property of pyramidal neurons in vitro, i.e. the ability of their dendrites to respond properly to extracellular cues patterning their outgrowth, thus enabling them to integrate appropriately in native cortical tissue.

Example 5

Generation of a Comprehensive Repertoire of Cortical Neurons Following a Precise Temporal Pattern Experimental Procedures Experimental procedures were as described in Examples 1 to 4.

BrdU Labelling

For long term pulse chase experiments, BrdU (Becton Dickinson) was added to the differentiation medium on the different days during 24 h at a final concentration of 10 µM. Cells were dissociated after 21 days of differentiation and plated on coated coverslips for an additional day. For short-term BrdU uptake experiments, BrdU was added to the differentiation medium during 1 hour prior to cell dissociation and replating.

For BrdU detection, medium was removed and cells were rinsed with PBS then fixed for 30 min in 4% paraformaldehyde (PFA) in PBS, pH 7.4 at 4° C. PFA was removed and cells were rinsed three times with PBS. BrdU was unmasked using an antigen retrieval method: cells were boiled during 4×5 minutes in 10 mM citrate buffer (pH 6.0) and cooled down to room temperature during 20 minutes. Immunostaining was performed as described above using mouse anti-BrdU (1/50, Becton Dickinson) or rat anti-BrdU (1/250, Abcam) antibodies. Multiple labelling was performed sequentially as described above.

Clonal Analyses

Protocol was adapted from a protocol for cortical progenitors clonal culture described by Qian et al. 2000 (Neuron 28: 69-80). Briefly, ES-derived neural progenitors at day 10, 12, 14 or 16 were trypsinized and thoroughly dissociated with a Pasteur pipette and subsequently with a 200 µl tip into a single-cell suspension. Dissociation was checked under a brightfield microscope and usually yields >99% single cells. Cells were plated on polylysin/laminin-coated coverslips at clonal density (3-5 cells/mm$^2$) into clonal medium supplemented with FGF2. Clonal medium was adapted from Qian et al. 2000, supra and consists in Neurobasal supplemented with 1×N2, 1×B27, 2 mM glutamine and 1× penicilline-streptomycine (Gibco). Half of the medium was changed every three days. FGF2 was added to the medium at concentrations (0.1 or 10 ng/ml) that have been shown to sustain clonal growth from single cortical progenitors and to allow the sequential generation of the different populations of cortical neurons from those progenitors (Qian et al. 2000, supra, and Shen et al. 2006. Nat Neurosci 9: 743-751).

Results

Pyramidal neurons can be subdivided into numerous subtypes, defined in vivo by a repertoire of molecular markers identifying distinct layer-specific neuronal populations (Hevner et al. 2003. Dev. Neurosci. 25: 139-151). We tested to which extent the neurons derived from ES cells in DDM+cyclo can generate in vitro the repertoire of neurons found in native cerebral cortex, whether such would be generated following a defined temporal pattern, similar to observed in vivo.

We studied the expression of the following layer-specific markers corresponding to the major subtypes of cortical neurons generated in vivo in the mouse, including: Tbr1 and reelin for preplate neurons and Cajal-Retzius cells; Tle4, Tbr1, CTIP2, Otx1, Er81, FoxP2 for deep (VNI) layer neurons; Satb2 and Cux1 for upper (II/III/IV) layer neurons and callosal projection neurons of layer V (see FIG. 5). For example, reelin appears at E9.5, and is a marker of Cajal-Retzius (C-R) neurons, the earliest generated cortical neurons (Ikeda & Terashima 1997. Dev Dyn 210: 157-172); Tbr1 appears at E10.5 and is expressed in Cajal-Retzius neurons, most layer VI neurons and a few layer V neurons (Bulfone et al. 1995. Neuron 15: 63-78); CTIP2 appears at E12.5 and is expressed mostly in layer V and a few layer VI neurons (Leid et al. 2004. Gene Expr Patterns 4: 733-739); Otx1 appears at E16 in the rat and is expressed in a subpopulation of layer V neurons (Frantz et al. 1994. J Neurosci 14: 5725-5740); Satb2 appears at E14.5 and is expressed in layer II/III/IV neurons (Britanova et al. 2005. Eur J Neurosci 21: 658-668).

of cortical identity at least at early stages of development. They also indicate that a comprehensive repertoire of distinct subtypes of cortical neurons corresponding to each cortical layer, including deep and upper cortical layers, is generated from ES cells in DDM+cyclo conditions. We also noted some interesting quantitative differences: in particular, in this experiment we observed a degree of over-representation of early neuronal subtypes and under-representation of upper layer neuronal subtypes (Table 2).

TABLE 2

Summary of the immunofluorescence data comparing the expression of layer-specific markers and their co-expression in ES cell-derived neurons and cortical neurons cultured ex vivo (this study) or as described in vivo (references).

|  | Laminar pattern of expression | ES cells-derived at day 21 (N = 3; n > 300; mean +/− SEM) | Ex vivo at P0 (N = 2; n > 200; mean +/− SEM) |
|---|---|---|---|
| Reelin-positive neurons | Cajal-Retzius cells | 20.20 +/− 1.26% | 4.70 +/− 1.00% |
| Tbr1-positive neurons among Reelin-positive neurons |  | 54.10 +/− 3.19% | 48.72 +/− 4.62% |
| CTIP2-positive neurons among Reelin-positive neurons |  | 27.00 +/− 3.14% | 14.07 +/− 2.99 |
| Cux1-positive neurons among Reelin-positive neurons |  | 0% | 0% |
| Satb2-positive neurons among Reelin-positive neurons |  | 0% | 0% |
| Tbr1-positive neurons | Cajal-Retzius cells, subplate, layers VI and V | 39.14 +/− 1.54% | 32.50 +/− 4.28% |
| CTIP2-positive neurons among Tbr1-positive neurons |  | 45.00 +/− 3.35% | Coexpression in layer VI and V (Molyneaux et al., Neuron 2005) |
| Tle4-positive neurons | Layers VI and V | 24.84 +/− 2.42% | 27.94 +/− 2.27% |
| FoxP2-positive neurons | Layer VI | 11.25 +/− 1.79% | ND |
| CTIP2-positive neurons | Layers VI and V | 36.01 +/− 1.52% | 29.66 +/− 2.55% |
| Tbr1-positive neurons among CTIP2-positive neurons |  | 54.10 +/− 3.19% | Coexpression in layer VI and V (Molyneaux et al., Neuron 2005) |
| Cux1-positive neurons among CTIP2-positive neurons |  | <1% | 0% |
| Satb2-positive neurons among CTIP2-positive neurons |  | <1% | 0% |
| Otx1-positive neurons | Layer V | 15.42 +/− 1.06% | 6.15 +/− 0.87% |
| ER81-positive neurons | Layer V | 5.05 +/− 0.66% | 3.30 +/− 0.86% |
| Cux1-positive neurons | Layers II-IV | 10.56 +/− 0.80% | 32.11 +/− 2.10% |
| Satb2-positive neurons | Layers II-IV | 7.60 +/− 0.78% | 37.50 +/− 4.32% |
| Tbr1-positive progenitors |  | 0% | 0% (Bulfone et al., Neuron 1995) |
| CTIP2-positive progenitors |  | 0% | 0% (Leid et al., Gene Expr Patterns 2004) |
| Satb2-positive progenitors |  | 0% | 0% (Britanova et al., Eur J Neurosci 2005) |
| Reelin-positive progenitors |  | 0% | 0% (D'Arcangelo et al., Nature 1995) |
| Pax6-positive neurons |  | <1% | <1% (Edlund et al., J Neurosci 2005) |

N = 3 independent experiments and n > 300 cells counted for the ES cell-derived neurons and progenitors at day 21 or 14, respectively. N = 2 independent experiments and n > 200 cells counted for acutely dissociated neurons at P0. Values are displayed as means +/− SEM of the proportion of labelled cells.

We first focused on days 16-21 of DDM+cyclo-treated cells, at the peak of generation of neurons. We found that each of these markers was expressed by a subset of the neurons: reelin (21.18+/−1.28% of all Tuj1+ neurons), Tbr1 (38.14+/−1.54%), CTIP2 (36.01+/−1.52%), Otx1 (15.42+/−1.06%), Satb2 (7.60+/−0.78%), and Cux1 (10.56+/−0.80%) (FIG. 6A, Table 2). These results further confirm the cortical identity of the neurons generated, as several of these markers are specific Next we examined the precise timing of onset of expression of these markers throughout the in vitro neurogenesis process, looking at time points from day 6 to day 21 of differentiation (FIG. 6 A).

The first detectable marker to appear in neurons was reelin, already detectable after 6 days of differentiation. The early appearance of reelin+ neurons raised the possibility that these could correspond to Cajal-Retzius neurons, as these neurons express reelin specifically and constitute the earliest generated neurons in the cortex. To confirm this hypothesis we performed combined stainings for other markers of Cajal-Retzius neurons, including p73, Tbr1, Tbr2 and calretinin, and found that the early reelin+ neurons co-expressed these markers as well. This strongly suggests that the earliest generated neurons from ES cells in DDM+cyclo conditions correspond indeed to Cajal-Rezius neurons in terms of molecular markers. In addition, these Tbr1/Calretinin/Reelin/p73+ neurons display a spontaneous migratory behaviour highly reminiscent of the in vitro behaviour of bona fide Cajal-Retzius neurons (data not shown). Moreover, examination of the overlay assays revealed the presence of eGFP+ neurons displaying an orientation and morphology reminiscent of Cajal-Retzius neurons in their native location in the superficial marginal zone of the cortex (FIG. 6B).

We next examined Tbr1, which is expressed in Cajal-Retzius neurons but also later in layer VI neurons. We found that it started to be expressed after 7 days of differentiation, thus one day later than reelin, consistent with the in vivo situation. Interestingly, after 8 days of differentiation, the proportion of Tbr1+ neurons increased much more than the proportion of reelin+ neurons (FIG. 6A), suggesting that at this time point the majority of Tbr1+ neurons that were generated did not express reelin, and therefore could correspond to layer VI-V neurons.

We then looked at CTIP2 and Otx1, which are mainly expressed in layer V neurons and a few layer VI neurons. Their onset of expression was consistently delayed from the onset of reelin and Tbr1 (FIG. 6A): Otx1 started to appear in a few neurons after only 8 days, while CTIP2 started to be only detectable after 9-10 days. This indicates that following DDM+cyclo conditions, like in vivo, markers of layer V neurons start to be expressed later than the markers of layer VI or Cajal-Retzius neurons.

Finally we looked at Satb2, which is expressed selectively in the latest generated cortical neurons of the most superficial cortical layers II/III/IV. Consistent with its in vivo timing of expression, it only appeared in neurons after 12 days of differentiation (FIG. 6A). Also Cux1 appeared in neurons after 12 days of differentiation.

Thus, neurons corresponding to distinct subtypes of cortical neurons are not generated simultaneously following DDM+cyclo conditions, but instead seem to appear sequentially and in a highly coordinated fashion, which is strikingly reminiscent of the sequence observed in the cerebral cortex in vivo. Altogether these data indicate that in default conditions of neural differentiation, ES cells display the intrinsic ability to generate a rather extensive repertoire of cortical neurons, and do so following a specification pathway that recapitulates the major milestones of normal in vivo cortical development.

Next we performed BrdU pulse chase experiments combined with staining of the neuronal markers, to determine the actual date of birth of each neuronal subtype in the ES system (FIG. 7). This analysis revealed that neurons expressing layer-specific markers are generated in sequential overlapping waves: first reelin and Tbr1+ neurons (peak at day 10-11), followed by CTIP2+ neurons (peaking at day 12-13), followed by Cux1+ and Satb2+ neurons (peaking at day 14-16) (FIG. 7). These data demonstrate that ES-derived neurons corresponding to distinct cortical subtypes appear following a coordinated sequence, as observed in vivo (Bayer & Altman 1991. Neocortical Development. Raven Press, New York; Hevner 2006. Mol Neurobiol 33: 33-50).

To explore the cellular mechanism involved we undertook cell lineage experiments based on clonal cell analyses (Shen et al. 2006. Nat Neurosci 9: 743-751). We first performed clonal dilutions of ES cell-derived neural progenitors at a fixed starting point (10 days of differentiation) and characterized the neuronal progeny following serial time points (2, 6, and 8 days) (FIG. 8A). At early stages (day 10+2), such clones of neural progenitors generated mostly reelin+ neurons and a few CTIP2+ neurons. With time the proportion of reelin+ neurons decreased substantially, while the proportion of CTIP2+ neurons increased. Satb2+ and Cux1+ neurons appeared later in the clones, with a maximum reached after 10+8 days in vitro.

Next we dissociated neural cultures from ES cells at different time points (from day 10 to day 16) and looked at their progeny after 6 days in vitro (FIG. 8B). Consistently with the previous data, we observed that clones obtained from early progenitors (dissociated at day 10) generated mostly reelin+ and some CTIP2+ neurons after 6 days, while clones obtained from later progenitors (dissociated at day 12, 14, 16), contained fewer and fewer reelin+ neurons, but many more CTIP2+ neurons. These experiments indicate that the competence of single neural progenitors changes with time, as they gradually lose the ability to generate early cell types. These experiments also enabled to detect a substantial proportion of clones containing different types of neurons, such as reelin and CTIP2 single labelled neurons (with a maximum at day 14+6), and reelin and Satb2 single labelled neurons (not shown).

Altogether these results provide direct evidence that the ES cell intrinsic pathway is encoded within lineages of individual progenitors, and leads to the generation of multipotent cortical progenitors that change in competence over time, as suggested with genuine cortical stem cells (Shen et al. 2006, supra; Noctor et al. 2004. Nat Neurosci 7: 136-144).

Example 6

ES-Derived Neurons Display a Wide Range of Layer-Specific but Selective Area-Specific Patterns of Axonal Projections Experimental Procedures
In Vivo Grafting Experiments In vivo grafting of ES cell-derived cortical neurons was performed as described previously for genuine embryonic cortical neurons, with the following modifications. Cells were trypsinized and thoroughly dissociated with a Pasteur pipette then centrifuged at 1200 rpm for 3 minutes. Supernatant was carefully discarded and the pellet was resuspended in ice cold PBS at a final density of $50 \times 10^3$ with a 200 µl tip and placed on ice.

P0-P1 mouse pups were anesthesized on ice. A small incision was performed through the skin and the skull 1 mm rostrally and laterally to the bregma, just above the motor area. A small cortical lesion was made with the tip of a 25-gauge needle and 1 µl of the cell suspension was injected with a Hamilton syringe in the rostral side of the lesion. After 3-4 weeks, the recipient animals were anesthesized with ketamine and xylazine and perfused with ice cold 4% PFA. Brains were harvested and 100 µm sections were obtained with a vibratome. Immunostaining was performed as described above using a rabbit anti-green fluorescent protein (1/3000, Molecular Probes).

All sections from each grafted animal (N=30 animals) were systematically reviewed after immunostaining. The location of the graft was noted and the presence of GFP+ axons was systematically checked in all of the following structures: the cortex, including the archi- and paleocortices, the corpus callosum, the external and internal capsules, the cingulum, the septum, the striatum, the thalamus (primary and associative nuclei), the cerebral peduncles, the superior and inferior colliculi, the midbrain and hindbrain nuclei, including the periaqueductal grey matter and the pediculopontine nuclei, and the pyramidal tracts down to the cervical spinal cord. Axonal fibers in each thalamic nucleus (LG, LP, LD, MG, VB, VL, VM), in visual areas and superior colliculus were manually scored in the grafted animals showing axonal growth to the thalamus (N=28 grafted animals). Scoring was done under conventional microscopy (Zeiss Axioplan) in each section where the thalamus was present, and the sum of the fibers scored in each section for each nucleus was considered the total number of fibers per nucleus. For the comparison of the projections from grafts emanating from cells differentiated at different time points (days 12, 14, 17 in vitro), the number of fibers in each analyzed structure (ipsi- and contralateral visual areas, thalamic LGN, midbrain superior colliculus) was normalized to the total number of fibers counted among all 4 structures in the same brain, thus providing the proportion of fibers innervating each structure, depending on the timing of in vitro differentiation. The pattern of projections of the different populations emanating from different time points was compared using the Chi-square test.

Results

The ultimate definition of neuronal identity relies on connectivity. In the cortex, pyramidal neurons display layer-specific and area-specific patterns of projections (FIG. 9 E, F). For instance layer VI neurons send their main projections to the thalamus, while most projections to other parts of the brain, including midbrain, hindbrain, and spinal cord emerge from layer V neurons. Neurons from layer V and layer II/III contribute to most of intracortical projections, including callosal projections to the contralateral cerebral hemisphere (Hevner et al. 2003, supra).

To test this prominent aspect of cortical neuronal specification, we undertook in vivo grafting experiments in neonatal mice: in this system, neural progenitors and neurons from embryonic cortex grafted into neonatal cortex connect faithfully with the rest of the host brain (O'Leary et al., 2007. Neuron 56: 252-269; Gaillard et al. 1998. Adv Anat Embryol Cell Biol 148: 1-86).

These experiments were performed using a Tau-GFP knock-in ES cell line (Wernig et al., 2002. J Neurosci Res 69: 918-924) that enables to identify selectively neurons and their axonal projections with great precision. ES cells were first allowed to differentiate as taught herein into neural progenitors and neurons for 12-17 days, then dissociated and grafted into the frontal cortex of P0-P1 mouse pups. Animals were then allowed to develop further and sacrificed after 1 month to analyze the differentiation and patterns of projections of the grafted cells (FIGS. 9-11). In all cases (N=30), the graft was localized either in the white matter underneath the motor and somatosensory cortex, or more superficially in the cortex gray matter itself, while in a few cases some grafted neurons were also found in structures neighbouring the ventricular system (FIGS. 9-11).

Analysis of the cellular composition of the grafts revealed that the vast majority of the cells in the graft (>90%) consisted of Tau-GFP+ and MAP2+ neurons, with only a few (<5%) Nestin+ and GFAP+ cells, as well as some PECAM+ vascular-like structures, probably reflecting neovascularization of the graft by the host (Table 3).

TABLE 3

Summary of the immunofluorescence data on the cellular composition of the grafts and the identity of the grafted neurons following grafting in neonatal cortex.

| Marker | Abundance | Notes |
| --- | --- | --- |
| GFP (Tau) | >90% | |
| MAP-2 | >90% | |
| Nestin | <5% | May originate from the host |
| GFAP | <5% | May originate from the host |
| Oct4 | Absent | ES cells marker |
| Pan-cyto-keratin | Absent | Epithelial marker |
| MF20 | Absent | Muscle marker |
| HNF-4 | Absent | Pre-hepatic endoderm marker |
| PECAM | <5% | Vascular endothelium marker; likely to reflect vascularization of the graft by the host |
| Activated caspase-3 | <1% | |
| Ki67 | <1% | |
| GAD67 | <1% | GABAergic neurons |
| ChAT | <1% | Cholinergic neurons |
| TH | Absent | Dopaminergic neurons |
| Rhodopsin | 0% | Photoreceptors |
| GABA-A receptor | 0% | Cerebellar granule cells |
| | | Laminar specificity at late postnatal ages and in adulthood |
| CTIP2 | 47 +/− 2% | Most neurons in layers VI and V |
| Tbr1 | 14 +/− 3% | A subpopulation of neurons in layer VI and V |
| Tle4 | 23 +/− 3% | Most neurons in layer VI and a subpopulation of neurons in layer V |
| FoxP2 | 12 +/− 2% | A subpopulation of neurons in layer VI and V |
| Cux1 | 11 +/− 2% | Upper layers and a subpopulation of neurons in layer V |

N = 11 animals.

Very few (<1%) Ki67+ proliferating cells were found within the graft, and no markers of endodermal, mesodermal, epidermal or ES cell lineages could be detected, suggesting that no teratoma formation had occurred, at least one month after grafting. Survival of the neurons was very high at one month with very few (<1%) cells labelled for activated caspase 3. Among the grafted neurons, we found that the same cortical neuron markers were present as in the in vitro situation, including FoxP2, Tle4, Tbr1, CTIP2, Cux1, Satb2, and COUPTF1/2.

The morphology of the grafted neurons was also assessed, focusing on single neurons surrounding the graft. In line with what was found in vitro, the vast majority (89+/−3.13%) of these neurons were unipolar with a PMI pyramidal index comparable to genuine pyramidal cortical neurons (FIG. 9d). Collectively these data lead to the important conclusion that the vast majority of the grafted cells indeed correspond to fully differentiated cortical pyramidal neurons, as in the in vitro situation.

We next examined the GFP+ pattern of projections of the grafted neurons. In most of the grafted animals, we found significant projections throughout the external capsule and corpus callosum, up to the ipsilateral and contralateral cortex, thus corresponding to cortico-cortical projections (FIG. 9 e,f, FIG. 11 a-c, Table 4)

TABLE 4

Semi-quantitative scoring of the axonal projections of ES-derived neurons in several cortical and sub-cortical structures following grafting in neonatal cortex.

| Age of grafted cells/host | D 12/P0 | | | | | | | | | | | D 14/P0 | | | | |
|---|---|---|---|---|---|---|---|---|---|---|---|---|---|---|---|---|
| Animals | 1 | 2 | 3 | 4 | 5 | 6 | 7 | 8 | 9 | 10 | 11 | 1 | 2 | 3 | 4 | 5 |
| Cortex | | | | | | | | | | | | | | | | |
| Visual il | ++ | + | + | ++ | ++ | ++ | − | ++ | ++ | ++ | ++ | +++ | +++ | − | +++ | ++ |
| Visual cl | − | − | − | − | + | − | − | − | − | − | − | ++ | ++ | − | ++ | + |
| Somatosensory cl | − | − | − | − | − | − | − | − | − | − | − | − | − | − | − | − |
| Auditory cl | − | − | − | − | − | − | − | − | − | − | − | − | − | − | − | − |
| Motor cl | − | − | − | − | − | − | − | − | − | − | − | − | − | − | − | − |
| Limbic cl | ++ | + | ++ | + | ++ | ++ | ++ | +++ | ++ | ++ | +++ | +++ | +++ | + | +++ | ++ |
| Thalamic nuclei | | | | | | | | | | | | | | | | |
| Anterior | − | − | − | − | − | − | − | ++ | ++ | ++ | + | ++ | ++ | − | ++ | ++ |
| Lateral geniculate | +++ | ++ | ++ | ++ | +++ | ++ | − | ++ | ++ | ++ | ++ | ++ | ++ | − | ++ | ++ |
| Lateral posterior | +++ | ++ | + | ++ | ++ | ++ | ++ | ++ | ++ | ++ | ++ | ++ | ++ | − | + | ++ |
| Latero-dorsal | +++ | ++ | ++ | ++ | ++ | ++ | ++ | ++ | ++ | ++ | ++ | ++ | ++ | + | ++ | ++ |
| Medio-dorsal | ++ | ++ | + | − | ++ | − | − | ++ | − | − | − | ++ | ++ | − | ++ | ++ |
| Ventrobasal/Ventral-lateral and Ventral-medial | ++ | ++ | − | − | + | − | − | − | − | + | − | + | ++ | − | + | ++ |
| Medial geniculate | + | − | − | − | + | − | − | + | − | − | − | − | − | − | + | − |
| Midbrain | | | | | | | | | | | | | | | | |
| Superior colliculus | +++ | ++ | + | − | ++ | − | − | ++ | ++ | ++ | − | +++ | +++ | − | +++ | ++ |
| Inferior colliculus | − | − | − | − | − | − | − | − | − | − | − | − | − | − | − | − |
| Periaqueductal grey matter | − | + | + | − | ++ | − | − | ++ | − | + | − | ++ | ++ | − | ++ | + |
| Hindbrain | | | | | | | | | | | | | | | | |
| Pediculopontine nuclei | + | + | − | − | − | − | − | − | + | − | − | ++ | ++ | − | ++ | + |
| Pyramidal tracts | − | − | − | − | − | − | − | − | − | − | − | − | − | − | − | − |
| Spinal Cord | − | − | − | − | − | − | − | − | − | − | − | − | − | − | − | − |

| Age of grafted cells/host | D 14/P0 | | | | | | D 17/P0 | | | | | | | |
|---|---|---|---|---|---|---|---|---|---|---|---|---|---|---|
| Animals | 6 | 7 | 8 | 9 | 10 | 11 | 1 | 2 | 3 | 4 | 5 | 6 | 7 | 8 |
| Cortex | | | | | | | | | | | | | | |
| Visual il | ++ | ++ | ++ | ++ | +++ | +++ | ++ | ++ | +++ | ++ | +++ | ++ | ++ | ++ |
| Visual cl | + | + | ++ | ++ | +++ | ++ | ++ | ++ | +++ | ++ | ++ | ++ | ++ | − |
| Somatosensory cl | − | − | − | − | − | − | − | − | − | − | − | − | − | − |
| Auditory cl | − | − | − | − | − | − | − | − | − | − | − | − | − | − |
| Motor cl | − | − | − | − | − | − | − | − | − | − | − | − | − | − |
| Limbic cl | ++ | ++ | +++ | ++ | +++ | +++ | +++ | ++ | +++ | +++ | +++ | ++ | ++ | +++ |
| Thalamic nuclei | | | | | | | | | | | | | | |
| Anterior | − | − | − | − | +++ | ++ | − | − | − | ++ | − | − | + | − |
| Lateral geniculate | − | ++ | ++ | + | ++ | ++ | ++ | − | ++ | ++ | + | + | − | − |
| Lateral posterior | − | + | ++ | + | ++ | − | ++ | − | ++ | ++ | ++ | ++ | − | − |
| Latero-dorsal | − | ++ | ++ | + | ++ | ++ | ++ | − | ++ | ++ | ++ | ++ | − | − |
| Medio-dorsal | − | + | + | − | ++ | + | + | − | + | ++ | + | + | − | − |
| Ventrobasal/Ventral-lateral and Ventral-medial | − | − | − | − | ++ | − | + | − | − | − | ++ | + | − | − |
| Medial geniculate | − | − | − | − | + | − | − | − | + | − | + | − | − | − |
| Midbrain | | | | | | | | | | | | | | |
| Superior colliculus | − | − | ++ | ++ | +++ | − | ++ | − | ++ | ++ | ++ | ++ | − | − |
| Inferior colliculus | − | − | − | − | − | − | − | − | − | − | − | − | − | − |
| Periaqueductal grey matter | − | − | + | − | ++ | ++ | + | − | ++ | + | − | − | − | − |
| Hindbrain | | | | | | | | | | | | | | |
| Pediculopontine nuclei | − | − | ++ | − | ++ | ++ | + | − | ++ | + | + | − | − | − |
| Pyramidal tracts | − | − | − | − | − | − | − | − | − | − | − | − | − | − |
| Spinal Cord | − | − | − | − | − | − | − | − | − | − | − | − | − | − |

Scoring used: (−) means no axon, (+) 1-10 axons, (++) 11-100 axons and (+++) more than 100 axons. N = 30 animals.

Projections corresponding to cortical efferents were then examined in the rest of the brain. GFP+ fibres were found in the striatum, internal capsule, thalamus, cerebral peduncles, midbrain, all the way down to pontine nuclei in the hindbrain (FIG. 9 g-l, FIG. 11, Table 4). Overall this pattern strikingly resembles the pattern of cortico-efferents, thus providing further evidence that most neurons generated from ES cells have a cortical identity. These results also demonstrate that the pattern of projections is generated by a diverse repertoire of cortical neurons, including projections to the thalamus (layer VI), the midbrain and hindbrain (layer V), and ipsilateral and contralateral areas of the cerebral cortex (layers II/III and V).

These findings prompted us to test whether the grafting of ES-derived neural progenitors and neurons differentiated after different periods of time (12, 14 and 17 days respectively), and thus possibly enriched for specific laminar fates, could generate different layer-specific patterns of projections in vivo. This analysis revealed that, although each considered population sent projections to all cortical targets, the proportion of projections found in thalamic, midbrain, and cortical targets, was different depending on the timing of differentiation. Grafts emanating from cells differentiated for shorter time points (12 days) displayed a higher proportion of projections to the thalamus than grafts emanating from cells differentiated for longer time points (days 14-17). Conversely, grafts emanating from later time points (14-17 days) displayed a higher proportion of projections to the cortex than the grafts from earlier time points (12 days), while the proportion of projections to the midbrain followed an intermediate temporal pattern (FIG. 10A; p<0.001 Chi-square test). These data thus strikingly indicate that the temporal pattern of layer-specific differentiation observed in vitro is correlated with a similar temporal pattern of layer-specific projections.

In addition to layer-specific patterns, cortical neurons display area-specific connectivity, so that each cortical area projects to selective targets in the rest of the brain (Paxinos, 1995. The Rat Nervous System. Academic Press, San Diego (1995). (FIG. 9 e, f).

To examine this crucial aspect of cortical connectivity, we performed a more detailed analysis of the patterns of projections of ES-derived grafted neurons. Surprisingly, in this experiment, we found that grafted neurons projecting to the cortex, thalamus and midbrain/hindbrain did not innervate these structures in a diffuse way, but in a precise manner, corresponding to visual and limbic occipital cortex (FIG. 9-11, Table 4). In the cortex, GFP+ axons could be seen in most (>90%) grafted animals in the visual areas, as well as in the limbic cortex, but no projections to motor or somatosensory areas were observed in the grafted animal (FIG. 10B, Table 4). In the thalamus (FIG. 9 j, FIG. 10C, Table 4), GFP+ axons were observed in most animals to innervate the visual thalamic (LG and LP), while in only a few cases to the other primary nuclei of the thalamus (VL, VB, and MG). Quantification of the distribution of GFP+ fibres in each main thalamic nucleus (FIG. 10C) revealed a much more dense innervation in visual thalamic nuclei than in any other primary thalamic nucleus, where only a few fibres were detected. Similarly, when examining projections to midbrain and hindbrain, in most cases (>80%) eGFP+ axons projected to the superior colliculus SC (FIG. 9 l, FIG. 10 B), the midbrain target of the visual cortex, while no fibres could be observed in the pyramidal tract or spinal cord corresponding to motor projections, or to the auditory inferior colliculus IC. In addition most grafted animals sent projections to the limbic cortex, medial thalamic nuclei, and midbrain periventricular gray matter, corresponding to structures receiving diffuse projections from the neocortex and limbic cortex (FIG. 10B, FIG. 11, Table 4).

A similar area-specific pattern of projection was found after different days of in vitro differentiation (days 12, 14, 17), suggesting that at least after 12 days in vitro, the cells were committed to these specific areal fates.

The projections of ES-cell derived neurons look strikingly similar to those described with late embryonic occipital cortex grafted into neonatal frontal cortex, that display a mainly visual identity, but quite distinct from the pattern reported for embryonic frontal cortex grafted into frontal cortex, which develop mainly motor-like projections (Gaillard et al. 1998, supra; Pinaudeau et al. 2000. Eur J Neurosci 12: 2486-2496; Ebrahimi-Gaillard et al. 1994. Brain Res Dev Brain Res 77: 271-283). Importantly our results were all obtained with grafts in the frontal cortex, suggesting that the patterns observed were not due to the re-specification of the grafted neurons through the influence of the host (O'Leary et al. 2007, supra; Pinaudeau of al. 2000, supra; Barbe & Levitt 1995. J Neurosci 15: 1819-1834). Our data may thus suggest that progenitors and neurons generated in vitro in the ES cell system undergo an area-specific differentiation process that results in a surprisingly specific identity, corresponding mainly to occipital/visual cortex. In accordance with this hypothesis, we found that a large proportion of Nestin+ progenitors generated at day 14 from ES cells expressed the CoupTFI and CoupTFII transcription factors (81.64+/−2.22% for CoupTFI, 95.1+/−1.23% for CoupTFII), that are preferentially expressed in the embryonic occipital/visual cortex (Armentano et al. 2007. Nat Neurosci 10: 1277-1286; Sansom et al. 2005. Development 132: 3947-3961).

Example 7

Stimulating the SHH Pathway and/or Antagonising the Wnt Pathway During Default Neurogenesis Converts Most Neural Progenitors to an Inhibitory Interneuron Identity To increase the proportion of ventral character of the ES cell-derived neural progenitors, we chose to increase Shh signalling, by adding soluble recombinant Shh to DDM, or to antagonize dorsalizing Wnt-signalling, by adding Dickkopf-1 (Dkk), a soluble antagonist of the Wnt pathway.

Addition of Shh at 1 µM, and even more at 10 µM, resulted in an increase in the proportion of Nkx2.1 positive progenitors (from 17.0±1.5% in DDM to 62.8±2.2% with 10 µM Shh, p<0.001; z-test for proportion; FIG. 12A), while the expression of Pax6 was decreased (from 40.1±1.8% in DDM to 20.4±1.4% with 10 µM Shh, p<0.001; FIG. 12A), consistent with a dorsal to ventral respecification of the identity of neural progenitors. Inhibition of canonical Wnt-signalling by addition of DKK largely generated the same results as Shh addition, though at a smaller scale: Nkx2.1 was induced from 17.0±1.5% of all Nestin-positive cells in DDM to 29.0±2.0% with 300 ng/ml Dkk (p<0.001; FIG. 12A); Pax6 decreased from 40.1±1.8% in DDM to 23.7±1.4% with Dkk300 (p<0.001; FIG. 12A). Similar effects were observed for Gsh2, Nkx2.2, Dlx1-2 (data not shown).

To determine effects of Shh and Dkk on the identity if the neurons generated, we looked at the expression of markers that could distinguish ventral from dorsal postmitotic neurons, after 21 days of culture, which corresponds to the peak of neurogenesis in the system. In good correlation with our observations in neural progenitors, increasing doses of Shh caused an overall decrease of dorsal and an increase of ventral neuronal markers (FIG. 12 B,C). The proportion of neurons positive for Reelin, a secreted glycoprotein mainly produced by Cajal-Retzius cells during cortical development, diminished from 28.0±2.7% in DDM to 16.6±1.8% in Shh10 (p<0.001; FIG. 12); neurons expressing Tbr1, a TF present in layers VI and V, fell from 23.8±2.7% in DDM to 0.7±0.5% in Shh10 (p<0.001; FIG. 12); VGluT1, a vesicular glutamate transporter restricted to glutamatergic projection neurons of the cerebral cortex and the cerebellum, decreased in these conditions from 58.2±3.6% to 33.7±2.6% (p<0.001; FIG. 12) while neurons positive for vGAT, a marker of ventral telencephalic neurons (including GABAergic striatal neurons and cortical interneurons), increased from 15.1±2.7% to 37.9±2.6% (p<0.001; FIG. 12); neurons marked by Islet-1, a TF expressed by neurons of the ventral forebrain including striatal interneurons and projection neurons, increased from 9.7±1.8% to 24.3±2.4% (p<0.001; FIG. 12). Again, similar effects were observed upon inhibition of Wnt-signalling by Dkk (FIG. 12C), and even more following combined addition of Shh and DKK (FIG. 12B).

These results indicate that forebrain-like ES cell-derived neural progenitors can be efficiently specified to a ventral character by acting on pathways that are involved in the specification of dorsoventral identity of the forebrain in vivo, including cortical and striatal interneurons and striatal projection neurons. This implies that our in vitro ES cell-based model of forebrain differentiation resembles the in vivo situation in this regard, and can be used to generate, with high efficiency, either GABA-ergic cortical/striatal interneurons or striatal projection neurons, which are neuronal classes of high clinical importance.

What is claimed is:

1. A method for differentiating mammalian embryonic stem (ES) cells into neural progenitors of dorsal forebrain identity comprising the steps of:
   a) plating undifferentiated ES cells onto a substrate which allows adherence of cells thereto; and
   b) culturing the ES cells of a) which have adhered to said substrate in a medium permissive to differentiation of the ES cells comprising exposing the cells to an antagonist of the sonic hedgehog (SHH) signalling pathway during at least part of the culturing step, whereby neural progenitors of dorsal forebrain activity are obtained.

2. The method for differentiating mammalian embryonic stem (ES) cells according to claim 1, wherein the neural progenitors of dorsal forebrain identity are positive at least for nestin and for any or all of orthodenticle homeobox 1 (OTX1), paired box protein PAX6, empty spiracles homolog 1 (Emx1), empty spiracles homolog 2 (Emx2) and Forkhead box protein G1 (FoxG1).

3. A method for differentiating ES cells into neural progenitors of ventral forebrain identity comprising the steps of:
   a) plating undifferentiated ES cells onto a substrate which allows adherence of cells thereto; and
   b) culturing the ES cells of a) which have adhered to said substrate in a medium permissive to differentiation of the ES cells comprising exposing the cells to an agonist of the SHH signalling pathway and to an antagonist of the Wnt signalling pathway during at least part of said culturing step, whereby neural progenitors of ventral forebrain identity are obtained.

4. The method for differentiating ES cells according to claim 3, wherein the neural progenitors of ventral forebrain identity are positive at least for nestin and for any or all of homeobox protein GSH2, homeodomain transcription factors NKX2.1 and NKX2.2, and homeobox proteins Dlx1 and Dlx2.

5. A method for differentiating mammalian embryonic stem (ES) cells into cortical pyramidal neuron like cells comprising the steps of:
   a) plating undifferentiated ES cells onto a substrate which allows adherence of cells thereto; and
   b) culturing the ES cells of a) which have adhered to said substrate in a medium permissive to differentiation of the ES cells comprising exposing the cells to an antagonist of the sonic hedgehog (SHH) signalling pathway during at least part of the culturing step, whereby cortical pyramidal neuron like cells are obtained.

6. The method according to claim 5, wherein the cortical pyramidal neuron like cells are positive at least for β-tubulin III (TUJ1) and/or microtubule associated protein 2 (MAP2), and for any one or both of vesicular glutamate transporter VGluT1 and VGluT2.

7. The method according to claim 5 further comprising enriching or isolating from the obtained cortical pyramidal neuron like cells a subpopulation of cells positive for one or more markers chosen from: reelin; TBR1; CTIP2; OTX1; SATB2; CUX1 or cells comprising the marker combination reelin, TBR1, calretinin and p73; or comprising the marker combination reelin and CTIP2; or comprising the marker combination Tbr1 and CTIP2; or comprising the marker combination Cux1 and SATB2.

8. A method for differentiating ES cells into cortical or striatal inhibitory interneuron or striatal projection neuron like cells comprising the steps of:
   a) plating undifferentiated ES cells onto a substrate which allows adherence of cells thereto; and
   b) culturing the ES cells of a) which have adhered to said substrate in a medium permissive to differentiation of the ES cells comprising exposing the cells to an agonist of the SHH signalling pathway and to an antagonist of the Wnt signalling pathway during at least part of said culturing step, into cortical or striatal inhibitory interneuron or striatal projection neuron like cells are obtained.

9. The method according to claim 8, wherein the cortical/striatal inhibitory interneuron or projection neuron like cells are positive at least for β-tubulin III (TUJ1) and/or MAP2, and for vesicular GABA transporter VGAT.

10. The method according to any one of claims 1-8, wherein the ES cells are non-human.

11. The method according to any one of claims 1-8, wherein the medium comprises insulin.

12. The method according to any one of claims 1-8, wherein the medium lacks external inductive morphogens, in particular lacks components that may otherwise induce caudalisation of neural progenitors, more in particular lacks any or all of serum or plasma; retinoic acid (RA); any members of the fibroblast growth factor (FGF) family of proteins; and any members of the Wnt family of proteins.

13. The method according to any one of claims 1-8, wherein the duration of the culturing step b) is between 10 days and 14 days.

14. The method according to any one of claims 1-8, wherein the duration of the culturing step b) is at least 21 days.

15. The method according to claim 1 or 5, wherein the antagonist of the sonic hedgehog (SHH) signalling pathway is cyclopamine or a functional derivative thereof.

16. The method according to claim 3 or 8, wherein the antagonist of the Wnt signalling pathway is DKK or a functional fragment or derivative thereof.

* * * * *

SEQUENCE LISTING

```
<160> NUMBER OF SEQ ID NOS: 28

<210> SEQ ID NO 1
<211> LENGTH: 21
<212> TYPE: DNA
<213> ORGANISM: artificial sequence
<220> FEATURE:
<223> OTHER INFORMATION: primer emx1

<400> SEQUENCE: 1
cccctcactc tttcttcagc g                                              21

<210> SEQ ID NO 2
<211> LENGTH: 20
<212> TYPE: DNA
<213> ORGANISM: artificial sequence
<220> FEATURE:
<223> OTHER INFORMATION: primer emx2

<400> SEQUENCE: 2
caccttctac ccctggctca                                                20

<210> SEQ ID NO 3
<211> LENGTH: 21
<212> TYPE: DNA
<213> ORGANISM: artificial sequence
<220> FEATURE:
<223> OTHER INFORMATION: primer pax6

<400> SEQUENCE: 3
aacctggcta gcgaaaagca a                                              21

<210> SEQ ID NO 4
<211> LENGTH: 22
<212> TYPE: DNA
<213> ORGANISM: artificial sequence
<220> FEATURE:
<223> OTHER INFORMATION: primer ngn2

<400> SEQUENCE: 4
acgcacgaga acgacaacac ac                                             22

<210> SEQ ID NO 5
<211> LENGTH: 20
<212> TYPE: DNA
<213> ORGANISM: artificial sequence
<220> FEATURE:
<223> OTHER INFORMATION: primer mash1

<400> SEQUENCE: 5
gaagcaggat ggcagcagat                                                20

<210> SEQ ID NO 6
<211> LENGTH: 20
<212> TYPE: DNA
<213> ORGANISM: artificial sequence
```

```
<220> FEATURE:
<223> OTHER INFORMATION: primer dlx1

<400> SEQUENCE: 6
ccaaaaggga agcagaggag                                               20

<210> SEQ ID NO 7
<211> LENGTH: 20
<212> TYPE: DNA
<213> ORGANISM: artificial sequence
<220> FEATURE:
<223> OTHER INFORMATION: primer dlx5

<400> SEQUENCE: 7
caccacccgt ctcaggaatc                                               20

<210> SEQ ID NO 8
<211> LENGTH: 24
<212> TYPE: DNA
<213> ORGANISM: artificial sequence
<220> FEATURE:
<223> OTHER INFORMATION: primer nkx2.1

<400> SEQUENCE: 8
aacctgggca acatgagcga gctg                                          24

<210> SEQ ID NO 9
<211> LENGTH: 21
<212> TYPE: DNA
<213> ORGANISM: artificial sequence
<220> FEATURE:
<223> OTHER INFORMATION: primer lhx6

<400> SEQUENCE: 9
tagagcctcc ccatgtacgc c                                             21

<210> SEQ ID NO 10
<211> LENGTH: 21
<212> TYPE: DNA
<213> ORGANISM: artificial sequence
<220> FEATURE:
<223> OTHER INFORMATION: primer lhx7

<400> SEQUENCE: 10
gaacaagaca cactggtggc a                                             21

<210> SEQ ID NO 11
<211> LENGTH: 21
<212> TYPE: DNA
<213> ORGANISM: artificial sequence
<220> FEATURE:
<223> OTHER INFORMATION: primer shh

<400> SEQUENCE: 11
gccagcggca gatatgaagg g                                             21

<210> SEQ ID NO 12
<211> LENGTH: 20
<212> TYPE: DNA
<213> ORGANISM: artificial sequence
<220> FEATURE:
<223> OTHER INFORMATION: primer ptc1

<400> SEQUENCE: 12
gctgtgcctg tggtcatcct                                               20
```

```
<210> SEQ ID NO 13
<211> LENGTH: 20
<212> TYPE: DNA
<213> ORGANISM: artificial sequence
<220> FEATURE:
<223> OTHER INFORMATION: primer ptc2

<400> SEQUENCE: 13
ctctggcact gggtctccga                                                   20

<210> SEQ ID NO 14
<211> LENGTH: 20
<212> TYPE: DNA
<213> ORGANISM: artificial sequence
<220> FEATURE:
<223> OTHER INFORMATION: primer foxG1

<400> SEQUENCE: 14
tgaagaggag gtggagtgcc                                                   20

<210> SEQ ID NO 15
<211> LENGTH: 21
<212> TYPE: DNA
<213> ORGANISM: artificial sequence
<220> FEATURE:
<223> OTHER INFORMATION: primer emx1

<400> SEQUENCE: 15
cagcccattc tcttgtccct c                                                 21

<210> SEQ ID NO 16
<211> LENGTH: 20
<212> TYPE: DNA
<213> ORGANISM: artificial sequence
<220> FEATURE:
<223> OTHER INFORMATION: primer emx2

<400> SEQUENCE: 16
ttctcggtgg atgtgtgtgc                                                   20

<210> SEQ ID NO 17
<211> LENGTH: 21
<212> TYPE: DNA
<213> ORGANISM: artificial sequence
<220> FEATURE:
<223> OTHER INFORMATION: primer pax6

<400> SEQUENCE: 17
ccatttggcc cttcgattag a                                                 21

<210> SEQ ID NO 18
<211> LENGTH: 22
<212> TYPE: DNA
<213> ORGANISM: artificial sequence
<220> FEATURE:
<223> OTHER INFORMATION: primer ngn2

<400> SEQUENCE: 18
gatcttcgtg agcttggcat cc                                                22

<210> SEQ ID NO 19
<211> LENGTH: 20
<212> TYPE: DNA
<213> ORGANISM: artificial sequence
<220> FEATURE:
<223> OTHER INFORMATION: primer mash1

<400> SEQUENCE: 19
```
acagaagcaa agaccgtggg         20

<210> SEQ ID NO 20
<211> LENGTH: 20
<212> TYPE: DNA
<213> ORGANISM: artificial sequence
<220> FEATURE:
<223> OTHER INFORMATION: primer dlx1

<400> SEQUENCE: 20
cccagatgag gagttcggat         20

<210> SEQ ID NO 21
<211> LENGTH: 20
<212> TYPE: DNA
<213> ORGANISM: artificial sequence
<220> FEATURE:
<223> OTHER INFORMATION: primer dlx5

<400> SEQUENCE: 21
gttacacgcc atagggtcgc         20

<210> SEQ ID NO 22
<211> LENGTH: 24
<212> TYPE: DNA
<213> ORGANISM: artificial sequence
<220> FEATURE:
<223> OTHER INFORMATION: primer nkx2.1

<400> SEQUENCE: 22
atcttgacct gcgtgggtgt cagg         24

<210> SEQ ID NO 23
<211> LENGTH: 19
<212> TYPE: DNA
<213> ORGANISM: artificial sequence
<220> FEATURE:
<223> OTHER INFORMATION: primer lhx6

<400> SEQUENCE: 23
tgctgcggtc tatgcttttt         19

<210> SEQ ID NO 24
<211> LENGTH: 22
<212> TYPE: DNA
<213> ORGANISM: artificial sequence
<220> FEATURE:
<223> OTHER INFORMATION: primer lhx7

<400> SEQUENCE: 24
cccataccgt ctgaagtaat cg         22

<210> SEQ ID NO 25
<211> LENGTH: 18
<212> TYPE: DNA
<213> ORGANISM: artificial sequence
<220> FEATURE:
<223> OTHER INFORMATION: primer shh

<400> SEQUENCE: 25
gtgcacggtg gcggatcc         18

<210> SEQ ID NO 26
<211> LENGTH: 20
<212> TYPE: DNA
<213> ORGANISM: artificial sequence

```
<220> FEATURE:
<223> OTHER INFORMATION: primer ptc1

<400> SEQUENCE: 26
caagggaggc tgatgtctgg                                                    20

<210> SEQ ID NO 27
<211> LENGTH: 21
<212> TYPE: DNA
<213> ORGANISM: artificial sequence
<220> FEATURE:
<223> OTHER INFORMATION: primer ptc2

<400> SEQUENCE: 27
ggggtcatca gggtccagac a                                                  21

<210> SEQ ID NO 28
<211> LENGTH: 20
<212> TYPE: DNA
<213> ORGANISM: artificial sequence
<220> FEATURE:
<223> OTHER INFORMATION: primer foxG1

<400> SEQUENCE: 28
gctgaacgag gacttgggaa                                                    20
```